(12) United States Patent
Gillis et al.

(10) Patent No.: US 9,510,922 B2
(45) Date of Patent: Dec. 6, 2016

(54) SYSTEMS AND METHODS FOR TREATMENT OF SLEEP APNEA

(75) Inventors: Edward M. Gillis, San Jose, CA (US); John H. Shadduck, Menlo Park, CA (US); Csaba Truckai, Saratoga, CA (US); Andrew Poutiatine, Mill Valley, CA (US); Paul J. Buscemi, Medina, MN (US)

(73) Assignee: ReVENT Medical, Inc., Alamo, CA (US)

( * ) Notice: Subject to any disclaimer, the term of this patent is extended or adjusted under 35 U.S.C. 154(b) by 175 days.

(21) Appl. No.: 13/113,946

(22) Filed: May 23, 2011

(65) Prior Publication Data

US 2011/0308530 A1      Dec. 22, 2011

Related U.S. Application Data

(60) Provisional application No. 61/347,348, filed on May 21, 2010, provisional application No. 61/347,356, filed on May 21, 2010, provisional application No. 61/367,707, filed on Jul. 26, 2010, provisional application No. 61/418,238, filed on Nov. 30, 2010, provisional application No. 61/419,690, filed on Dec. 3, 2010.

(51) Int. Cl.
*A61F 2/00* (2006.01)
*A61F 5/56* (2006.01)

(52) U.S. Cl.
CPC ................ *A61F 2/00* (2013.01); *A61F 5/566* (2013.01); *A61F 2210/0004* (2013.01)

(58) Field of Classification Search
CPC .............. A61F 5/56; A61F 5/566; A61F 2/00; A61F 2/0063; A61F 2/02; A61F 2/04; A61F 2002/046; A61B 17/04; A61B 17/0401
USPC .................. 128/848; 623/9, 11, 14; 602/902
See application file for complete search history.

(56) References Cited

U.S. PATENT DOCUMENTS

| | | | |
|---|---|---|---|
| 4,424,208 | A | 1/1984 | Wallace et al. |
| 4,582,640 | A | 4/1986 | Smestad et al. |
| 4,978,323 | A | 12/1990 | Freedman |
| 5,041,138 | A | 8/1991 | Vacanti et al. |
| 5,145,935 | A | 9/1992 | Hayashi |
| 5,326,355 | A | 7/1994 | Landi |

(Continued)

FOREIGN PATENT DOCUMENTS

| | | |
|---|---|---|
| EP | 1216013 B1 | 6/2006 |
| EP | 2561842 A1 | 2/2013 |

(Continued)

OTHER PUBLICATIONS

Gillis, Edward M..; U.S. Appl. No. 13/308,449 entitled "Systems and methods for treatment of sleep apnea," filed Nov. 30, 2011.

(Continued)

*Primary Examiner* — Victoria J Hicks
*Assistant Examiner* — Raymond E Harris
(74) *Attorney, Agent, or Firm* — Shay Glenn LLP

(57) ABSTRACT

An implant for treating an obstructive airway disorder includes an elongate implant body configured for implanting in airway-interface tissue. At least a portion of the elongate body carries a light transmission material for permitting light transmission therein. Systems and methods of treating an airway disorder including implanting an implant in an airway-interface tissue are also provided.

18 Claims, 61 Drawing Sheets

(56) References Cited

U.S. PATENT DOCUMENTS

| | | | |
|---|---|---|---|
| 5,372,600 A | 12/1994 | Beyar et al. | |
| 5,428,024 A | 6/1995 | Chu et al. | |
| 5,506,300 A | 4/1996 | Ward et al. | |
| 5,531,761 A | 7/1996 | Yoon | |
| 5,665,822 A | 9/1997 | Bitler et al. | |
| 5,697,779 A | 12/1997 | Sachdeva et al. | |
| 5,762,599 A | 6/1998 | Sohn | |
| 5,775,322 A | 7/1998 | Silverstein et al. | |
| 5,782,636 A * | 7/1998 | Armstrong et al. | 433/165 |
| 5,972,000 A | 10/1999 | Beyar et al. | |
| 5,972,111 A | 10/1999 | Anderson | |
| 5,979,456 A | 11/1999 | Magovern | |
| 5,988,171 A * | 11/1999 | Sohn et al. | 128/848 |
| 6,019,779 A | 2/2000 | Thorud et al. | |
| 6,161,541 A | 12/2000 | Woodson | |
| 6,165,486 A | 12/2000 | Marra et al. | |
| 6,197,043 B1 | 3/2001 | Davidson | |
| 6,231,605 B1 | 5/2001 | Ku | |
| 6,250,307 B1 | 6/2001 | Conrad et al. | |
| 6,388,043 B1 | 5/2002 | Langer et al. | |
| 6,390,096 B1 | 5/2002 | Conrad et al. | |
| 6,395,017 B1 | 5/2002 | Dwyer et al. | |
| 6,401,717 B1 | 6/2002 | Conrad et al. | |
| 6,415,796 B1 | 7/2002 | Conrad et al. | |
| 6,431,174 B1 | 8/2002 | Knudson et al. | |
| 6,439,238 B1 | 8/2002 | Brenzel et al. | |
| 6,450,169 B1 | 9/2002 | Conrad et al. | |
| 6,453,905 B1 | 9/2002 | Conrad et al. | |
| 6,458,127 B1 | 10/2002 | Truckai et al. | |
| 6,467,485 B1 | 10/2002 | Schmidt | |
| 6,502,574 B2 | 1/2003 | Walter et al. | |
| 6,507,675 B1 | 1/2003 | Lee et al. | |
| 6,513,530 B2 | 2/2003 | Knudson et al. | |
| 6,513,531 B2 | 2/2003 | Knudson et al. | |
| 6,516,806 B2 | 2/2003 | Knudson et al. | |
| 6,523,541 B2 | 2/2003 | Knudson et al. | |
| 6,523,542 B2 | 2/2003 | Knudson et al. | |
| 6,530,896 B1 | 3/2003 | Elliott | |
| 6,546,936 B2 | 4/2003 | Knudson et al. | |
| 6,569,191 B1 | 5/2003 | Hogan | |
| 6,578,763 B1 | 6/2003 | Brown | |
| 6,601,584 B2 * | 8/2003 | Knudson et al. | 128/897 |
| 6,626,181 B2 | 9/2003 | Knudson et al. | |
| 6,626,916 B1 | 9/2003 | Yeung et al. | |
| 6,629,988 B2 | 10/2003 | Weadock | |
| 6,634,362 B2 | 10/2003 | Conrad et al. | |
| 6,636,767 B1 | 10/2003 | Knudson et al. | |
| 6,703,040 B2 | 3/2004 | Katsarava et al. | |
| 6,748,950 B2 | 6/2004 | Clark et al. | |
| 6,748,951 B1 | 6/2004 | Schmidt | |
| 6,772,944 B2 | 8/2004 | Brown | |
| 6,899,105 B2 | 5/2005 | Krueger et al. | |
| 7,017,582 B2 | 3/2006 | Metzger et al. | |
| 7,022,132 B2 | 4/2006 | Kocur | |
| 7,063,089 B2 | 6/2006 | Knudson et al. | |
| 7,090,672 B2 | 8/2006 | Underwood et al. | |
| 7,107,992 B2 | 9/2006 | Brooks et al. | |
| 7,146,981 B2 | 12/2006 | Knudson et al. | |
| D536,792 S | 2/2007 | Krueger et al. | |
| 7,188,627 B2 | 3/2007 | Nelson et al. | |
| 7,192,443 B2 | 3/2007 | Solem et al. | |
| 7,213,599 B2 | 5/2007 | Conrad et al. | |
| 7,237,554 B2 * | 7/2007 | Conrad et al. | 128/897 |
| 7,255,110 B2 | 8/2007 | Knudson et al. | |
| 7,322,356 B2 | 1/2008 | Critzer et al. | |
| 7,337,781 B2 * | 3/2008 | Vassallo | 128/897 |
| 7,793,661 B2 | 9/2010 | Macken | |
| 7,824,704 B2 | 11/2010 | Anderson et al. | |
| 7,909,037 B2 | 3/2011 | Hegde et al. | |
| 7,909,038 B2 | 3/2011 | Hegde et al. | |
| 7,934,506 B2 | 5/2011 | Woodson et al. | |
| 7,947,076 B2 | 5/2011 | Vassallo et al. | |
| 7,992,567 B2 | 8/2011 | Hirotsuka et al. | |
| 7,997,266 B2 | 8/2011 | Frazier et al. | |
| 8,186,355 B2 | 5/2012 | van der Burg et al. | |
| 8,220,466 B2 | 7/2012 | Frazier et al. | |
| 8,381,735 B2 * | 2/2013 | Buscemi et al. | 128/848 |
| 8,409,296 B2 | 4/2013 | Knize et al. | |
| 8,528,564 B2 | 9/2013 | Paraschac et al. | |
| 9,050,176 B2 | 6/2015 | Datta et al. | |
| 2001/0051815 A1 | 12/2001 | Esplin | |
| 2002/0020417 A1 | 2/2002 | Nikolchev et al. | |
| 2002/0116070 A1 | 8/2002 | Amara et al. | |
| 2004/0045556 A1 | 3/2004 | Nelson et al. | |
| 2004/0204734 A1 | 10/2004 | Wagner et al. | |
| 2005/0004417 A1 | 1/2005 | Nelson et al. | |
| 2005/0065615 A1 | 3/2005 | Krueger et al. | |
| 2005/0090861 A1 | 4/2005 | Porter | |
| 2005/0092332 A1 | 5/2005 | Conrad et al. | |
| 2005/0115572 A1 | 6/2005 | Brooks et al. | |
| 2005/0121039 A1 | 6/2005 | Brooks et al. | |
| 2005/0154412 A1 | 7/2005 | Krueger et al. | |
| 2005/0171572 A1 | 8/2005 | Martinez | |
| 2005/0199248 A1 | 9/2005 | Pflueger et al. | |
| 2005/0267321 A1 | 12/2005 | Shadduck | |
| 2005/0274384 A1 | 12/2005 | Tran et al. | |
| 2006/0150986 A1 | 7/2006 | Roue et al. | |
| 2006/0201519 A1 | 9/2006 | Frazier et al. | |
| 2006/0207606 A1 | 9/2006 | Roue et al. | |
| 2006/0229669 A1 | 10/2006 | Mirizzi et al. | |
| 2006/0235380 A1 | 10/2006 | Vassallo | |
| 2006/0260623 A1 | 11/2006 | Brooks et al. | |
| 2006/0289014 A1 | 12/2006 | Purdy et al. | |
| 2006/0289015 A1 | 12/2006 | Boucher et al. | |
| 2007/0010787 A1 | 1/2007 | Hackett et al. | |
| 2007/0108077 A1 | 5/2007 | Lung et al. | |
| 2007/0144534 A1 | 6/2007 | Mery et al. | |
| 2007/0198040 A1 | 8/2007 | Buevich et al. | |
| 2007/0261701 A1 | 11/2007 | Sanders | |
| 2007/0288057 A1 | 12/2007 | Kuhnel | |
| 2007/0295340 A1 | 12/2007 | Buscemi | |
| 2008/0023012 A1 | 1/2008 | Dineen et al. | |
| 2008/0027560 A1 | 1/2008 | Jackson et al. | |
| 2008/0053461 A1 | 3/2008 | Hirotsuka et al. | |
| 2008/0058584 A1 * | 3/2008 | Hirotsuka et al. | 600/37 |
| 2008/0066764 A1 | 3/2008 | Paraschac et al. | |
| 2008/0066765 A1 | 3/2008 | Paraschac et al. | |
| 2008/0066766 A1 | 3/2008 | Paraschac et al. | |
| 2008/0066767 A1 | 3/2008 | Paraschac et al. | |
| 2008/0066769 A1 | 3/2008 | Dineen et al. | |
| 2008/0078411 A1 | 4/2008 | Buscemi et al. | |
| 2008/0078412 A1 | 4/2008 | Buscemi et al. | |
| 2008/0082113 A1 | 4/2008 | Bishop et al. | |
| 2008/0188947 A1 | 8/2008 | Sanders | |
| 2009/0038623 A1 | 2/2009 | Farbarik et al. | |
| 2009/0044814 A1 | 2/2009 | Iancea et al. | |
| 2009/0084388 A1 | 4/2009 | Bagley et al. | |
| 2009/0126742 A1 | 5/2009 | Summer | |
| 2009/0177027 A1 | 7/2009 | Gillis | |
| 2009/0319046 A1 | 12/2009 | Krespi et al. | |
| 2010/0037901 A1 | 2/2010 | Rousseau et al. | |
| 2010/0132719 A1 | 6/2010 | Jacobs et al. | |
| 2010/0137905 A1 * | 6/2010 | Weadock et al. | 606/228 |
| 2010/0158854 A1 | 6/2010 | Puisais | |
| 2010/0163056 A1 | 7/2010 | Tschopp et al. | |
| 2011/0100377 A1 | 5/2011 | Weadock et al. | |
| 2011/0144421 A1 | 6/2011 | Gillis | |
| 2011/0166598 A1 | 7/2011 | Gonazles et al. | |
| 2011/0174315 A1 | 7/2011 | Zhang et al. | |
| 2011/0290258 A1 | 12/2011 | Pflueger et al. | |
| 2012/0143134 A1 | 6/2012 | Hollis et al. | |
| 2012/0180799 A1 | 7/2012 | Pflueger et al. | |
| 2012/0197070 A1 | 8/2012 | Gillis | |
| 2012/0266895 A1 * | 10/2012 | Frazier et al. | 128/848 |
| 2013/0098374 A1 | 4/2013 | Gillis et al. | |
| 2013/0109910 A1 | 5/2013 | Alexander et al. | |
| 2013/0218289 A1 | 8/2013 | Gao et al. | |
| 2013/0233324 A1 | 9/2013 | Witt et al. | |
| 2014/0246027 A1 | 9/2014 | Gillis et al. | |

(56) References Cited

U.S. PATENT DOCUMENTS

| 2014/0251344 | A1 | 9/2014 | Gillis |
| 2014/0261451 | A1 | 9/2014 | Gillis et al. |

FOREIGN PATENT DOCUMENTS

| JP | 05-337126 A | 12/1993 |
| JP | 2604833 | 1/1997 |
| JP | 2001198147 | 7/2001 |
| JP | 2006507038 | 3/2006 |
| JP | 2007-97706 | 4/2007 |
| JP | 2007-512090 | 5/2007 |
| JP | 2007229485 | 9/2007 |
| JP | 2007525277 | 9/2007 |
| WO | WO 97/18854 A1 | 5/1997 |
| WO | WO 99/00058 A1 | 1/1999 |
| WO | WO 00/66050 A1 | 11/2000 |
| WO | WO 01/89426 A1 | 11/2001 |
| WO | WO 02/76341 A2 | 2/2002 |
| WO | WO 02/013738 A1 | 10/2002 |
| WO | WO 02/076352 A1 | 10/2002 |
| WO | WO 02/076353 A1 | 10/2002 |
| WO | WO 02/076354 A1 | 10/2002 |
| WO | WO 03/041612 A2 | 5/2003 |
| WO | WO 03/055417 A1 | 7/2003 |
| WO | WO 03/065947 A1 | 8/2003 |
| WO | WO 2005/044158 A1 | 5/2005 |
| WO | WO 2006/012188 A1 | 2/2006 |
| WO | WO 2006/093533 A1 | 9/2006 |
| WO | WO 2006/101610 A2 | 9/2006 |
| WO | WO 2007/056583 A1 | 5/2007 |
| WO | WO 2007/070024 A2 | 6/2007 |
| WO | WO 2008/042058 A1 | 4/2008 |
| WO | WO 2008/097890 A2 | 8/2008 |
| WO | WO 2009/032625 A1 | 3/2009 |
| WO | WO 2010/028036 A1 | 3/2010 |
| WO | WO 2010/045546 A1 | 4/2010 |
| WO | WO 2010/051195 A1 | 5/2010 |

OTHER PUBLICATIONS

Gillis et al.; U.S. Appl. No. 13/311,460 entitled "Systems and methods for treatment of sleep apnea," filed Dec. 5, 2011.
Gillis et al.; U.S. Appl. No. 13/539,081 entitled "Systems and Methods for Treatment of Sleep Apnea," filed Jun. 29, 2012.
Jeon et al.; Shape memory and nonostructure in poly(norbornyl-POSS) copolymers; Polym Int; vol. 49; pp. 453-457; 2000.
Lui et al.; Thermomechanical characterization of a tailored series of shape memory polymers; J Applied Med Polymers; vol. 6/ No. 2; pp. 47-52; 2002.
Mather et al.; Strain recovery in POSS hybrid thermoplastics; Polymer; vol. 41, No. 1; pp. 528-529; 2000.
Gillis et al.; U.S. Appl. No. 13/053,025 entitled "Systems and methods for treatment of sleep apnea," filed Mar. 21, 2011.
Gillis et al.; U.S. Appl. No. 13/053,059 entitled "Systems and methods for treatment of sleep apnea," filed Mar. 21, 2011.
Gillis et al.; U.S. Appl. No. 13/269,520 entitled "Partially erodable systems for treatment of obstructive sleep apnea," filed Oct. 7, 2011.
Gillis et al.; U.S. Appl. No. 13/113,933 entitled "Systems and methods for treatment of sleep apnea ," filed May 23, 2011.
Gillis, Edward M.; U.S. Appl. No. 13/188,385 entitled "Systems and methods for treatment of sleep apnea ," filed Jul. 21, 2011.
Gillis et al.; U.S. Appl. No. 13/935,052 entitled "Systems and Methods for Treatment of Sleep Apnea," filed Jul. 3, 2013.
Gillis et al.; U.S. Appl. No. 13/939,107 entitled "Systems and Methods for Treatment of Sleep Apnea," filed Jul. 10, 2013.
Gillis; U.S. Appl. No. 13/954,589 entitled "Partially Erodable Systems for Treatment of Obstructive Sleep Apnea" filed Jul. 30, 2013.
DeRowe et al.; A minimally invasive technique for tongue base stabilization in obstructive sleep apnea; Operative Techniques in Otolaryngology—Head and Neck Surgery; 11(1); pp. 41-46; Mar. 2000.
Miller et al.; Role of the tongue base supension suture with the Repose System bone screw in multileval surgical management of obstructive sleep apnea; Otolaryngol Head Neck Surg.; 126(4); pp. 392-398; Apr. 2002.
Walker et al.; Palatal implants for snoring and sleep apnea; Operative Techniques in otolaryngology; 17(4); pp. 238-241; Dec. 2006.
Woodson et al.; Pharyngeal suspension suture with Repose bone screw for obstructive sleep apnea; Otolaryngol Head Neck Surg.; 122(3); pp. 395-401; Mar. 2000.
Rampersaud et al.; U.S. Appl. No. 14/340,324 entitled "Systems and methods for treatment of an airway disorder," filed Jul. 24, 2014.
Collins English Dictionary; "elastomer" (definition); Complete & Unabridged; 10th Edition; HarperCollins Publishers; May 11, 2015; retrieved from the internet (http://dictionary.reference.com/browse/elastomeric>).

* cited by examiner

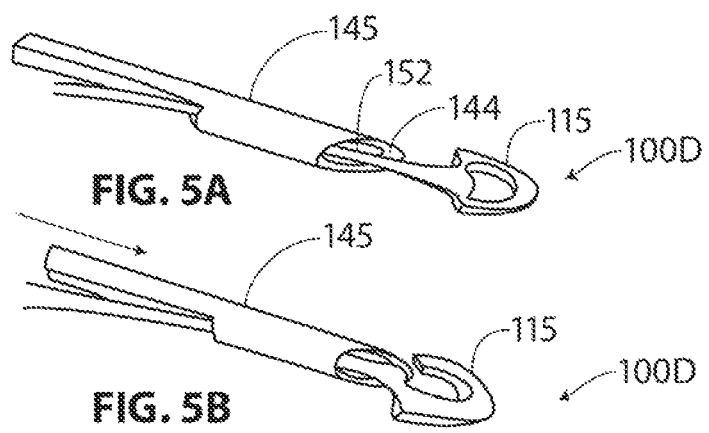
FIG. 5A
FIG. 5B
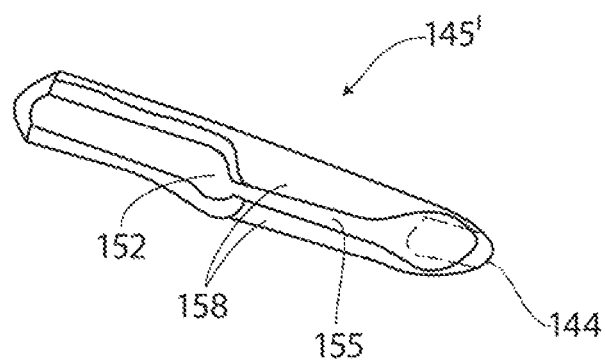
FIG. 6
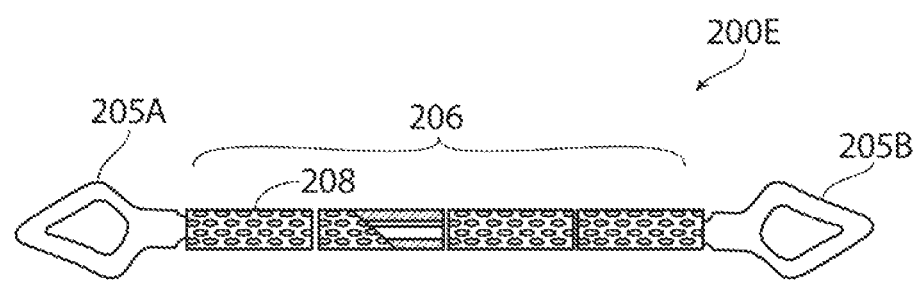
FIG. 7E

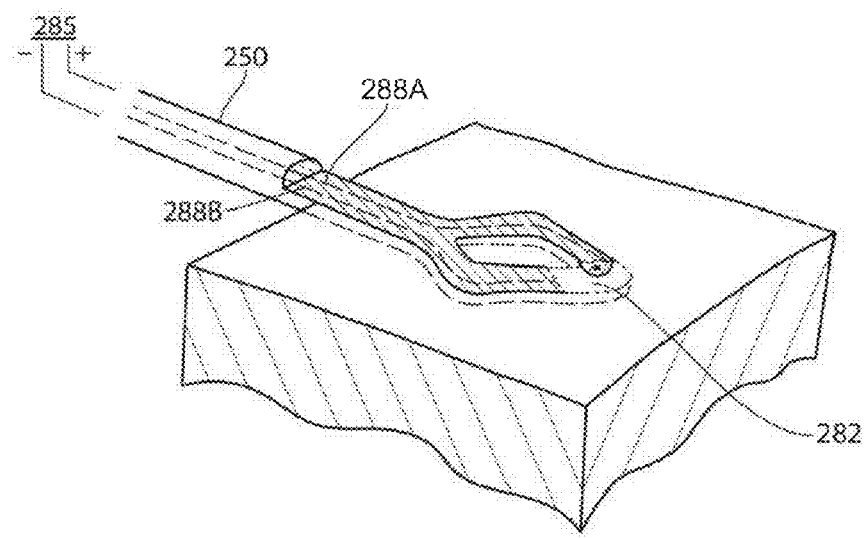
FIG. 12
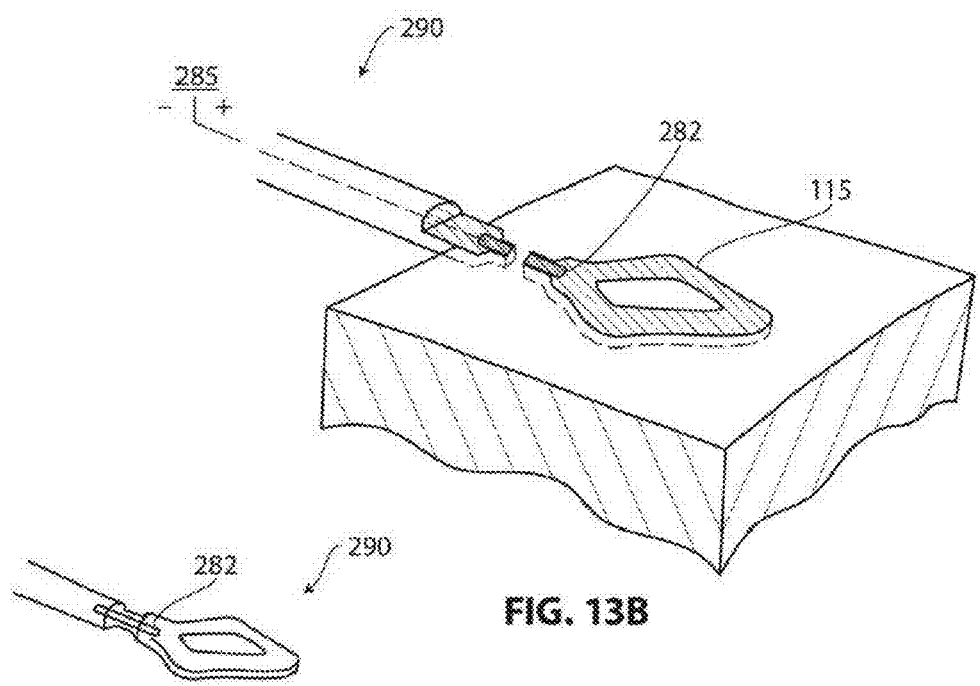
FIG. 13B
FIG. 13A

# SYSTEMS AND METHODS FOR TREATMENT OF SLEEP APNEA

CROSS-REFERENCE TO RELATED APPLICATIONS

This application claims priority to: U.S. Provisional Application No. 61/347,348 filed May 21, 2010; U.S. Provisional Application No. 61/347,356 filed May 21, 2010; U.S. Provisional Application No. 61/367,707 filed Jul. 26, 2010; U.S. Provisional Application No. 61/418,238 filed Nov. 30, 2010; U.S. Provisional Application No. 61/419,690 filed Dec. 3, 2010.

INCORPORATION BY REFERENCE

This application is related to co-pending patent applications: U.S. application Ser. No. 11/969,201 filed Jan. 3, 2008; U.S. application Ser. No. 12/937,564 filed Jan. 3, 2011; U.S. application Ser. No. 13/053,025 filed Mar. 21, 2011; U.S. application Ser. No. 13/053,059 filed Mar. 21, 2011. All publications, patents and patent applications mentioned in this specification are herein incorporated by reference to the same extent as if each individual publication, patent or patent application was specifically and individually indicated to be incorporated by reference.

FIELD OF THE INVENTION

The disclosure relates to the field of methods and devices for the treatment of obstructive sleep apnea, and more particularly to opening the airway of subjects with symptoms of obstructive sleep apnea.

BACKGROUND OF THE INVENTION

Sleep apnea is defined as the cessation of breathing for ten seconds or longer during sleep. During normal sleep, the throat muscles relax and the airway narrows. During the sleep of a subject with obstructive sleep apnea (OSA), the upper airway narrows significantly more than normal, and during an apneic event, undergoes a complete collapse that stops airflow. In response to a lack of airflow, the subject is awakened at least to a degree sufficient to reinitiate breathing. Apneic events and the associated arousals can occur up to hundreds of times per night, and become highly disruptive of sleep. Obstructive sleep apnea is commonly but not exclusively associated with a heavy body type, a consequence of which is a narrowed oropharyngeal airway.

Cyclic oxygen desaturation and fragmented sleeping patterns lead to daytime sleepiness, the hallmark symptom of the disorder. Further consequences of sleep apnea may include chronic headaches and depression, as well as diminished facilities such as vigilance, concentration, memory, executive function, and physical dexterity. Ultimately, sleep apnea is highly correlated with increased mortality and life threatening co-morbidities. Cardiology complications include hypertension, congestive heart failure, coronary artery disease, cardiac arrhythmias, and atrial fibrillation. OSA is a highly prevalent disease condition in the United States. An estimated 18 million Americans suffer from OSA to degrees that range from mild to severe, many of whom are undiagnosed, at least in part because the afflicted subjects are often unaware of their own condition.

Treatment of OSA usually begins with suggested lifestyle changes, including weight loss and attention to sleeping habits (such as sleep position and pillow position), or the use of oral appliances that can be worn at night, and help position the tongue away from the back of the airway. More aggressive physical interventions include the use of breathing assist systems that provide a positive pressure to the airway through a mask that the subject wears, and which is connected to a breathing machine. In some cases, pharmaceutical interventions can be helpful, but they generally are directed toward countering daytime sleepiness, and do not address the root cause. Some surgical interventions are available, such as nasal surgeries, tonsillectomy and/or adenoidectomy, reductions in the soft palate, uvula or the tongue base, or advancing the tongue base by an attachment to the mandible and pulling the base forward. These surgical approaches can be quite invasive and thus have a last-resort aspect to them, and further, simply do not reliably alleviate or cure the condition. There is a need for less invasive procedures that show promise for greater therapeutic reliability. There is additional need for the ability to reverse procedures or otherwise revise the procedure, thus allowing for the ability to reverse or otherwise revise the effects of the procedure due to side effects or other undesirable outcomes which may result from the procedure. Additionally, there is the need to do these procedural reversals or revisions in a manner that does not require excessive tissue cutting or invasiveness which can act as a deterrent for patients or physicians to perform such a revision procedure.

SUMMARY OF THE INVENTION

The invention relates to a method of alleviating obstructive collapse of airway-forming tissues, and for devices with which to implement the method. Typical patients for whom the method and device may provide therapeutic benefit are those who suffer from obstructive sleep apnea. The method includes implanting a device at a site in the tissue and bioeroding the bioerodible portion of the device to change the shape of the device and to remodel the airway-forming tissue. The implanted device is sized and shaped to conform to the airway-forming tissue site in a manner compatible with normal physiological function of the site; and includes a resiliently deformable portion and a bioerodible portion. In typical embodiments of the method, remodeling the airway-forming tissue results in the airway being unobstructed during sleep, and further, typically, the thus-unobstructed airway diminishes the frequency of apneic events. Remodeling may include reshaping or otherwise altering the position or conformation of airway associated tissue so that its tendency to collapse during sleep is diminished.

The airway is formed from various tissues along its length from the mouth to the lungs. Embodiments of the method include implanting a resilient implant, such as an elastomeric device, into any one or more of these tissues, including, for example, the soft palate, the tongue, generally the base of the tongue, and the pharyngeal walls, typically the posterior and lateral portions of the pharyngeal wall.

In some embodiments, the device is in a deformed shape when implanted, and a bioerodable portion erodes to thereby release a tensioned shape of the implant to apply retraction forces to the site.

With regard to the bioeroding of the bioerodible portion of the device, this may occur over a time span that ranges from days to months. In some embodiments, the bioeroding proceeds at a rate that correlates with the ratio of the biologically-exposed surface area of the bioerodible portion to the volume of the bioerodible portion.

In some embodiments of the method, the bioerosion occurs at a rate that is sufficiently slow for the tissue site to recover from the implanting prior to the device substantially changing shape. In some of these embodiments, the recovery of the tissue site includes a forming of fibrotic tissue around the device, which typically stabilizes the device in the site, and provides the device greater leverage with which to reform the shape of the implant site and its surrounding tissue. In some embodiments, after implanting, and as part of the healing response or recovery from the implantation wound, the newly formed fibrotic tissues infiltrates into holes, pores, or interstices in the device. In some embodiments of the method, a bioactive agent, previously incorporated into the bioerodible material, is released or eluted from the bioerodible portion of the device as it is eroding.

In another aspect of the methods described herein, a method of forming a device to alleviate obstructive collapse of an airway during sleep is provided. The method includes forming a resiliently deformable material into an initial shape that corresponds to the preferred shape of the device, the initial shape having a site for accommodating bioerodible material; changing the initial shape of the resiliently deformable material into a non-preferred shape that is sized and configured into an implantable shape that conforms to an airway-forming tissue site and is compatible with normal physiological function after implantation; and stabilizing the implantable shape by incorporating the bioerodible material into the accommodating site. In some of these method embodiments, changing the initial shape of the resiliently deformable material includes absorbing a force sufficient to remodel the airway as the force is transferred from the device into an implant site after implantation of the device. That level of force is further typically insufficient to remodel the airway to an extent that it is unable to move in a manner that allows substantially normal or acceptable physiological function of the airway.

As noted above, some aspects of the disclosure further provide a device for alleviating obstruction in an airway, such obstruction typically occurring during sleep. Embodiments of the device include an implantable device sized and shaped to conform to an airway-forming tissue site in a manner compatible with normal physiological function of the site, the device including a resiliently deformable portion and a bioerodible portion. In these embodiments, the resiliently deformable portion has a preferred shape that is constrained in a deformed shape by the bioerodible portion, and the device is configured to return toward the preferred shape of the resiliently deformable portion upon erosion of the bioerodible portion. In some embodiments, the preferred configuration is adapted to remodel the shape of the airway so as to provide a more open airway during sleep.

In typical embodiments of the device, the resiliently deformable portion may include any one or more of a metal or a polymer. In these embodiments, a resiliently deformable metal may include any one or more of stainless steel, spring steel, or superelastic nickel-titanium alloy, and a resiliently deformable polymer may include any one or more of silicon rubber, polyesters, polyurethanes, or polyolefins. In some embodiments, the bioerodible portion may include any one or more of polycaprolactone, polylactic acid, polyglycolic acid, polylactide coglycolide, polyglactin, poly-L-lactide, polyhydroxalkanoates, starch, cellulose, chitosan, or structural protein.

Some embodiments of the device include a portion adapted to engage the tissue into which it is implanted, and in some of these embodiments, the so-adapted portion includes a site for tissue in-growth, such in-growth serving to keep the device and tissue in close proximity, serving to promote implant site remodeling in a manner that conforms to the changing shape of the device. Finally, in some embodiments, the implantable device is configured with sufficient elasticity to allow normal physiological movement around an airway-forming tissue implant site when the device is implanted in the implant site.

In other embodiments, the adapted portion contains sites for tissue to link through the implant after implantation forming tissue plugs which thus form an attachment between the implant and the adjacent tissue without a corresponding adhesion of tissue to the implant. This type of arrangement can produce an implant that can effectively attach to and move tissue while remaining easily removable from the tissue. The tissue plugs can be formed by linking the implant around an encircled mass of tissue or allowing tissue to heal through the implant thus forming the island of encircled tissue. Implants can contain one or more encircled masses of tissue allowing attachment to the adjacent tissue. In some embodiments, a proximal end of the implant is anchored to the patient's mandible and a distal end or ends of the implant is/are releasably anchored to one or more tissue plugs.

In some embodiments, a method of treating an airway disorder is provided which comprises placing an implant in airway-interface tissue, wherein at the implant has first and second end portions and a medial portion there between. The method also includes coupling the end portions in situ to allow the medial portion to encircle targeted tissue. In some embodiments, the implant applies inwardly-directed forces on the encircled tissue. The implant displaces tissue that is encircled by the implant in some embodiments. The medial portion of the implant may include first and second sections with different elastic properties. In some embodiments, the coupling step is accomplished by coupling means selected from the group of clips, snap-fit features, pins, ratchets, sutures, stakes, clamps, welds, fusible materials and adhesives. The airway-interface tissue may comprise the tongue, the soft palate and/or pharyngeal tissue. In some embodiments, the implant encircles the geniohyoid muscle.

In some embodiments, a method of treating an airway disorder is provided which comprises placing an implant in airway-interface tissue, wherein at the implant has first and second end portions. The first and second end portions are configured to anchor in tissue and have a curved medial portion extending along a curvilinear axis. The medial portion is configured to provide tensile forces along said axis and transverse to the curved portion.

In some embodiments, an implant for treating an airway disorder is provided which comprises an implant body for implanting in airway-interface tissue. The implant body has first and second end portions and a medial portion. The implant body also includes a coupler for coupling the end portions to one another such that the medial portion encircles targeted tissue. The coupler may comprise at least one of clips, snap-fit features, pins, ratchets, sutures, stakes, clamps, welds, fusible materials and adhesives. The implant may further comprise a linear implant linearly coupled to an encircling portion of the implant body. The encircling portion of the implant body may be configured for vertical or horizontal placement in a patient's tongue, and/or for encircling a patient's geniohyoid muscle.

In some embodiments, a method of treating an airway disorder is provided which comprises implanting an implant body in a patient's tongue. The implant applies a minimum threshold force in alignment with muscle fibers of about 0.5 Newtons, about 1.5 Newtons, or about 3.5 Newtons. The minimum threshold force may be applied by a single implant and/or by a plurality of implants.

In some embodiments, a method of treating an airway disorder is provided which comprises implanting an implant body in a patient's soft palate. The implant applies a minimum threshold force in alignment with the surface of the soft palate of about 0.2 Newtons, about 0.5 Newtons, or about 1.0 Newtons.

In some embodiments, a method of treating an airway disorder is provided which comprises implanting an implant body into airway-interface tissue. The implant body is sized and shaped to conform in a manner compatible with normal physiological function of the site and to apply selected forces to the tissue. The implant encircles a region of airway tissue and elongated elastic portions of the implant are aligned with the axes of contractile muscle fibers.

In some embodiments, a system for treating an airway disorder is provided which comprises an elongated introducer assembly including a guide member. The system also includes first and second hollow trocar elements extendable from the guide member in a predetermined angle relative to one another. The system of these embodiments also includes an elongated implant carried within a passageway in a trocar element. The first and second trocar elements may have first and second respective distal sidewall ports that oppose one another. The system may comprise a tissue-tunneling member. The tissue tunneling member may be releasably carried within a passageway in a trocar element. The tissue-tunneling member may be of a flexible material and/or a shape memory alloy. The tissue-tunneling member may be configured for bridging between first and second ports and/or for passing between the passageways of the first and second trocar elements. The system may comprise a push rod in the passageway for deploying the tunneling member. The system may comprise a stylette in a passageway in a trocar for engaging a tunneling member.

In some embodiments, a system for treating an airway disorder is provided which comprises an elongated introducer assembly including a guide housing. The system further comprises first and second trocar elements extendable from the guide housing in a predetermined diverging path relative to one another. An elongated V-shaped implant is carried within passageways of the trocar elements. The trocar elements may each have a resilient curved distal end. The trocar elements may comprise a shape memory alloy. Each of the trocar elements may carry a leg of the V-shaped implant. Each of the trocar elements may have a slot-type passageway for carrying the V-shaped implant. Each of the trocar elements may carry a stylette coupled to end portions of the V-shaped implant for deploying the implant.

BRIEF DESCRIPTION OF THE DRAWINGS

FIG. 5A depicts a second component of a revisable OSA implant system, the second component comprising a cutting tool.

FIG. 5B depicts the cutting tool of FIG. 5A in a method of use.

FIG. 6 depicts an alternative cutting tool similar to that of FIGS. 5A-5B.

FIG. 7E is a partially cut-away view that depicts an OSA implant with an elastomeric portion that is configured for being releaseably maintained in a tensioned or non-repose condition by a magnesium or magnesium alloy biodissolvable material or element.

FIG. 12 is a cut-away view depicting the implant of FIG. 11 in a tissue site after actuation of the sacrificial portion of the implant.

FIG. 13A depicts an alternative implant including an electrolytically sacrificial portion that can be sacrificed in response to a direct current.

FIG. 13B is a cut-away view depicting the implant of FIG. 13A in a tissue site after actuation of electrolytic connection portion of the implant.

FIG. 44G depicts the trocar system proximate the patient with the trocars being withdrawn, leaving the implant in place.

DETAILED DESCRIPTION OF THE INVENTION

A. Anatomy of the Pharynx

Figure 1:
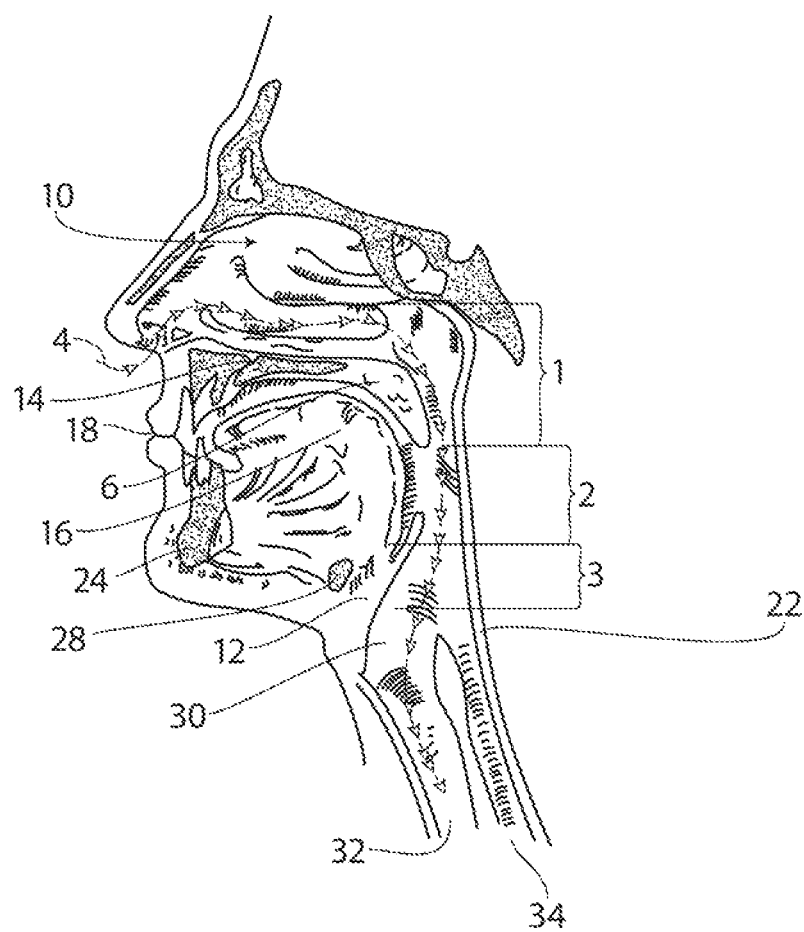
FIG. 1 provides an overview of the healthy human airway anatomy, with particular attention to the nasopharyngeal, oropharangeal, and hypopharyngeal regions.
Figure 2A:
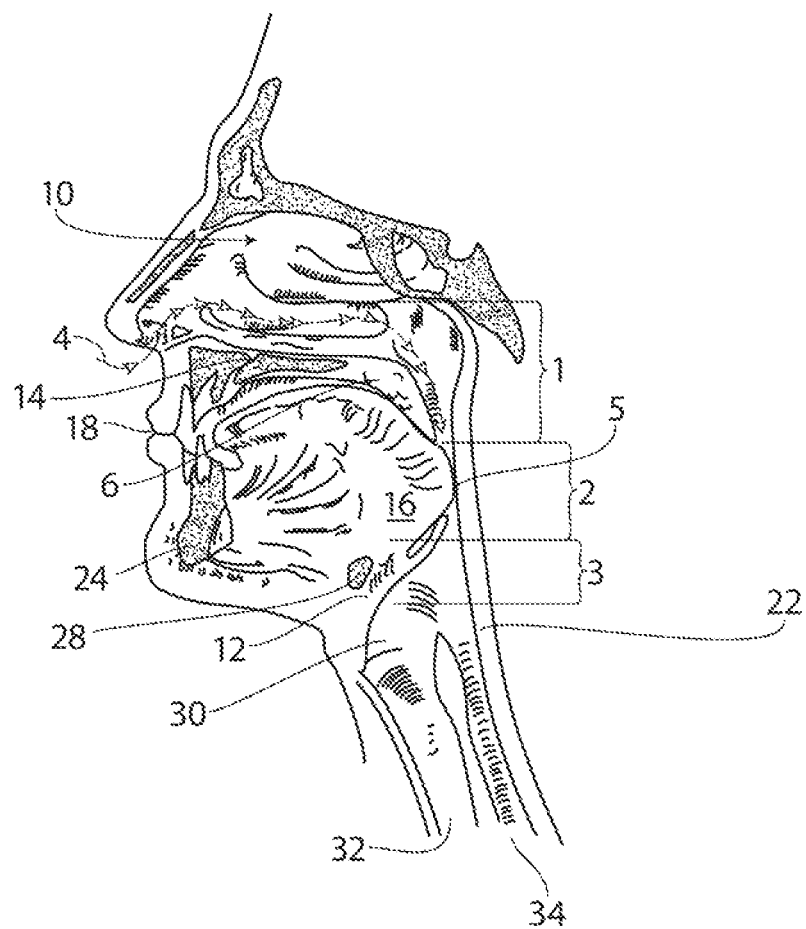
FIG. 2A provides a view of a compromised airway, with an occlusion in the oropharyngeal region due to posterior slippage of the base of the tongue.
Figure 2B:
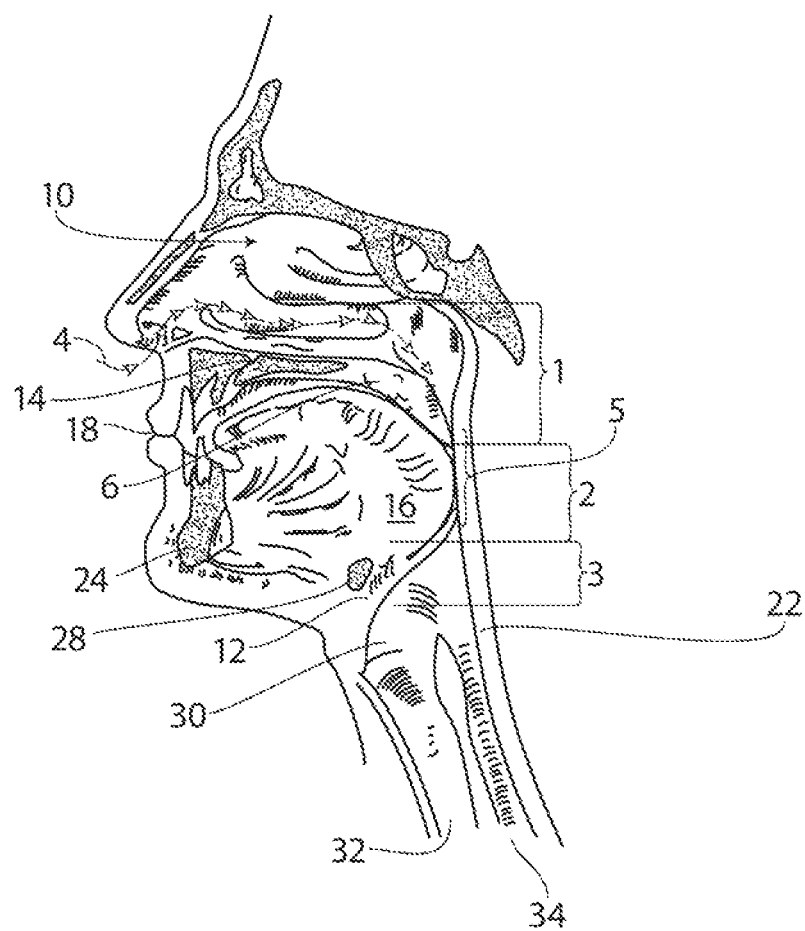
FIG. 2B provides a view of a compromised airway with palate closure.

FIG. 1 is a sagittal view of the structures that form the pharyngeal airway 4; some of these structures can become compromised under various conditions to the extent that they obstruct or occlude passage of air through the airway 4, and thus contribute to obstructive sleep apnea. The pharynx is divided, from superior to inferior, into the nasopharynx 1, the oropharynx 2 and the hypopharynx 3. Variations of FIG. 1 are provided in FIGS. 2A and 2B which depict airway obstruction sites 5 at various levels in the pharyngeal airway. FIG. 2A, for example, shows an occlusion 5 at the level of the oropharynx 2, where the base of the tongue 16 and a thickened posterior pharyngeal wall 22 have collapsed against each other. FIG. 2B provides a view of a compromised airway with palate closure. It is also possible for airway obstruction to occur at the level of the nasopharynx 1, where an elongated and/or floppy soft palate can collapse against a thickened posterior pharyngeal wall. Further, an obstruction can occur at the level of the hypopharynx 3, where both an elongated soft palate and a floppy epiglottis 12 can collapse against the pharyngeal wall 22.

With reference to FIGS. 1-2B, the nasopharynx is the portion of the pharynx at the level or above the soft palate 6. In the nasopharynx, a deviated nasal septum or enlarged nasal turbinates 10 may occasionally contribute to upper airway resistance or blockage. Rarely, a nasal mass, such as a polyp, cyst or tumor may be a source of obstruction. The oropharynx 2 includes structures from the soft palate 6 to the upper border of the epiglottis 12 and includes the inferior surface of the hard palate 14, tongue 16, posterior pharyngeal wall 22 and the mandible 24 as well as the tonsils and palatoglossal arch. The mandible typically has a bone thickness of about 5 mm to about 10 mm anteriorly with similar thicknesses laterally. An obstruction in the oropharynx 2 may result when the tongue 16 is displaced posteriorly during sleep as a consequence of reduced muscle activity during deep or non-REM sleep. The displaced tongue 16 may push the soft palate 6 posteriorly and may seal off the nasopharynx 1 from the oropharynx 2. The tongue 16 may also contact the posterior pharyngeal wall 22, which causes further airway obstruction. Also shown is the mouth 18.

The hypopharynx 3 includes the region from the upper border of the epiglottis 12 to the inferior border of the cricoid cartilage. The hypopharynx 3 further includes the hyoid bone 28, a U-shaped, free-floating bone that does not articulate with any other bone. The hyoid bone 28 is attached to surrounding structures by various muscles and connective tissues. The hyoid bone 28 lies inferior to the tongue 16 and superior to the thyroid cartilage 30. A thyrohyoid membrane and a thyrohyoid muscle attach to the inferior border of the hyoid 28 and the superior border of the thyroid cartilage 30. The epiglottis 12 is infero-posterior to the hyoid bone 28 and attaches to the hyoid bone by a median hyoepiglottic ligament. The hyoid bone attaches anteriorly to the infero-posterior aspect of the mandible 24 by the geniohyoid muscle. Below the hypopharynx 3, the trachea 32 and esophagus 34 are also shown.

B. Revisable OSA Implants

Figure 3A:
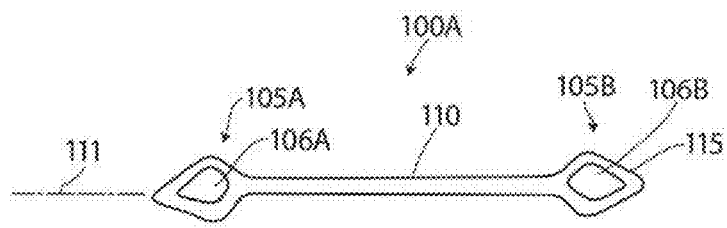
FIG. 3A depicts an elongate implant component of a revisable OSA implant system, the implant having end portions with openings for growth of a tissue plug therethrough to secure the end portions in a treatment site.

FIG. 3A depicts a first component in an exemplary embodiment of a kit or system that provides revisable implants for treating an airway disorders or obstructive sleep apnea (OSA). The second component of the exemplary kit is an introducer for insertion into a treatment site as is known in the art and co-pending applications. In FIG. 3A, an elongate device or implant body 100A has first and second end portions 105A and 105B with through-openings 106A and 106B therein. The medial portion 110 of the implant body 100A extends along axis 111 and comprises a biocompatible elastomeric material such as a silicone. The mean cross-section of the medial body portion 110 can range from 1 to 10 mm$^2$ and can be round, oval, flat, polygonal or other suitable shapes. In some embodiments, the elastic modulus of the medial portion can range from 0.5 to 10 MPA and is configured for implanting in the patient's airway tissue in a releasable, tensioned position, as described in co-pending U.S. patent application Ser. No. 11/969,201 which is incorporated herein by this reference.

Figure 3C:
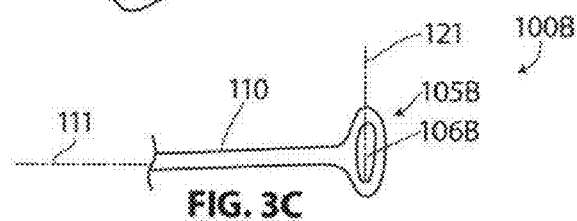
FIG. 3C depicts another elongate implant embodiment similar to that of FIG. 3A.
Figure 3D:
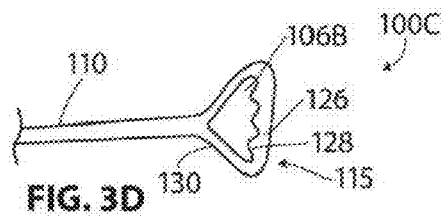
FIG. 3D depicts another elongate implant embodiment.
Figure 3B:
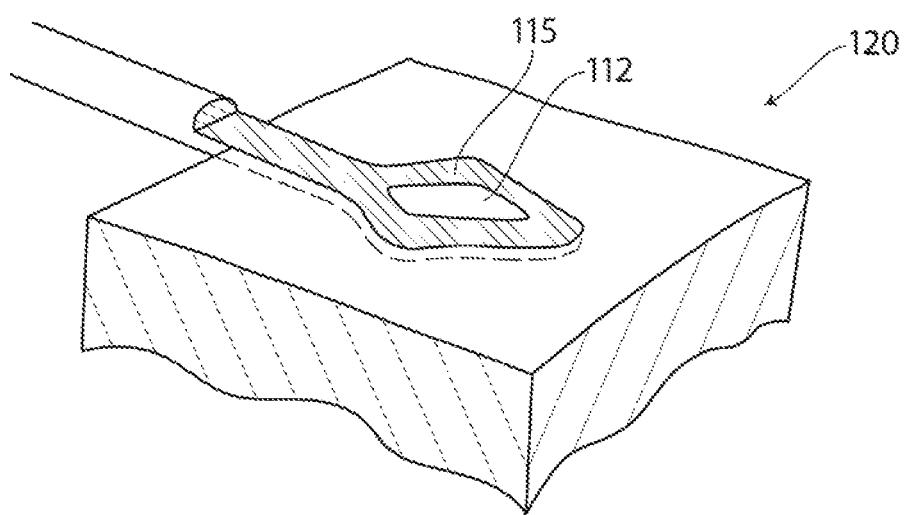
FIG. 3B is a cut-away view of an end portion of the implant of FIG. 3A in a tissue site.

Referring to FIG. 3A and 3B, it can be seen that through-openings 106A and 106B in the implant body 100A are configured for growth of a tissue plug 112 through the opening to thereby secure the first and second end portions 105A and 105B in a selected tissue site. The cut-away view of FIG. 3B schematically illustrates that a tissue plug 112 that grows through the opening is thus surrounded or encircled by an encircling body portion 115 of the implant. The encircling body portion 115 comprises a small cross-section element that can be cut, severed, sacrificed, decoupled, or dissolved to disengage the implant from a tissue site 120 as will be described below. The element can be a polymer or other material. In other embodiments described below, the tissue plug 112 can be cut or severed to disengage the implant from the tissue site 120. In one embodiment, the mean cross-section of the tissue plug 112, and thus the dimension across an opening 106A or 106B, can range from about 0.5 mm to 10 mm or more. The openings 106A or 106B can have a round shape in plan view or any other plan shape. The end portions 105A and 105B can have similar or dissimilar configurations, for example an implant configured for treatment of a patient's tongue may have a substantially larger end portion and opening 106B for the base of the tongue and a smaller end portion near the mandible.

FIG. 3C illustrates another implant body 100B with an end portion 105B having an elongated opening 106B through which tissue will grow to form a tissue plug to secure the end portion in the site. For example, the implant body 100B of FIG. 3C has an opening 106B with a primary axis 121 and larger dimension that extends generally orthogonal to the axis 111 of medial portion 110 of the implant body. In use, the greater dimension of the tissue plug will better resist the retraction forces applied to tissue by the elastomeric medial portion 110 of the implant aligned with axis 111.

FIG. 3D depicts another embodiment 100C of a revisable implant for treating an airway disorder that is similar to that of FIG. 3C except the end portion 105B has a through-opening 106B with a terminal part 126 of encircling portion 115 configured with irregular shaped surface features 128 that can interface with the tissue plug that grows through opening 106B. The surface features can comprise undulations, textures, protrusions, bumps and the like that can assist in maintaining the end portion in a fixed position when under the tensioning or retraction forces applied by the medial portion 110 of the implant body 100C. In the implant body 100C of FIG. 3D, the end portion 105B also can have an encircling element 115 that includes a proximal portion 130 of a lower modulus material similar to the modulus of medial portion 110 and the terminal part 126 having a higher modulus to prevent its deformation under tensioning forces.

Figure 4:
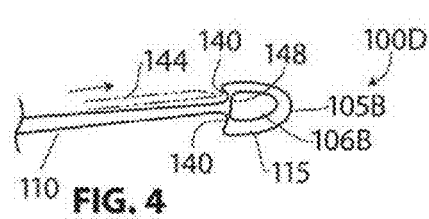
FIG. 4 depicts another elongate implant corresponding to aspects of the invention.

FIG. 4 depicts another embodiment 100D of a revisable implant that is similar to previous embodiments except that at least one end portion 105B includes an indent feature 140 in the proximal-facing aspect of the encircling portion 115 wherein the indent feature 140 is adapted to direct and receive a cutting blade or edge 144 (phantom view) of a cutting tool for cutting the encircling portion of the implant body to allow its removal from the treatment site. As will be described below (with reference to FIG. 5B), a cutting tool 145 can be advanced along the medial portion 110 of the implant to sever the end portion, which then will allow the entire implant to be withdrawn from the implant site. In another aspect of the invention, the indent feature 140 in the encircling portion 115 can direct the cutting edge 144 to a reduced cross section portion 148 that will require limited force to cut the polymer element with the cutting edge 144.

FIGS. 5A and 5B illustrate a second component of an exemplary kit of a revisable OSA implant system wherein the tool 145 comprises an elongate member with a distal cutting edge 144. One tool embodiment has a passageway 152 extending therethrough for receiving the elongate implant body 100D. In using this tool 145, a first end of the implant body would be freed from tissue or cut and then threaded through the passageway 152. Thereafter, as depicted in FIG. 5B, the tool 145 can be advanced distally while holding the proximal end of the implant to cause the cutting edge 144 to cut across the encircling portion 115. In FIG. 5B, it can be understood how the indent feature 140 and reduced cross section portion 148 (see FIG. 4) direct the cutting edge 144 to easily cut the element to thus release the implant from encircling the tissue plug 112 (cf. FIG. 3B). The tool 145 can be a rigid or semi-rigid member such as a hypotube with a sharpened end. The tool also can be a deflectable, articulatable or steerable member as is known in the art. In another embodiment, the tool can be a flexible plastic material with a blade insert to provide the cutting edge 144. Referring to FIGS. 5B and 3B, it can be understood that the cut end is flexible and can be pulled from around the tissue plug to extract the implant from the site 120 (see FIG. 3B).

FIG. 6 illustrates another second tool component of a revisable implant system wherein the tool 145' again comprises an elongate member with a distal cutting edge 144. In one embodiment, the tool end includes a longitudinal gap 155 along a side of passageway 152 to thus allow the tool to be inserted over medial portion 110 of an implant body to then advance and cut the implant as depicted schematically in FIGS. 5A-5B. The tool end as shown in FIG. 6 can comprise a polymer member with flexible elements 158 on either side of gap 155 to allow gap 155 to flex open when the device is being inserted over the implant. As depicted, distal cutting edge 144 may comprise a metal blade insert 160 molded into a polymer member.

Figure 7A:
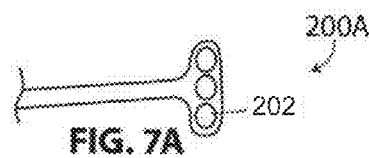
FIG. 7A depicts another elongate implant corresponding to aspects of the invention.
Figure 7B:
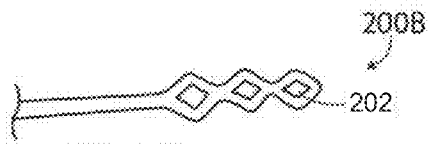
FIG. 7B depicts another elongate implant embodiment.
Figure 7C:
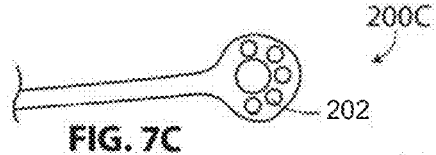
FIG. 7C depicts another elongate implant embodiment.

FIGS. 7A-7C illustrate other embodiments of implants 200A, 200B and 200C that each has a plurality of through-openings 202 in various configurations. In these embodiments, the ends are flat or planar with the openings therein. Thus, in use, there will be a plurality of tissue plugs that grow through the openings to secure the implant ends in the tissue site.

Figure 7D:
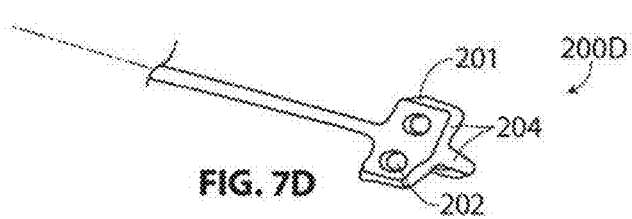
FIG. 7D depicts another elongate implant embodiment with multiple openings in multiple planes.

FIG. 7D illustrates another embodiment of implant 200D that has a non-planar end 201 with a plurality of through-openings 202. In one embodiment, the ends have a plurality of elements 204 that extend in different radial angles relative to the axis 111 of the implant with each such element 204 having one or more openings therein.

FIG. 7E illustrates an implant body 200E with ends 205A and 205B and medial portion 206 that comprises an axially-stretched and tensioned elastomeric material. The medial portion 206 is releasably and temporarily maintained in the axially-stretched non-repose condition by a biodissolvable portion, such as of magnesium or magnesium alloy, indicated at 208. In this embodiment, the biodissolvable portion can comprise a tubular member with a foil-like wall or thin-wall, a plurality of thin-wall tube segments, or one or more windings or braids of biodissolvable material. The thin-wall material can be perforated as shown in FIG. 7E. The thin-wall biodissolvable material, or the biodissolvable filament of a winding or braid, can be very fine and adapted to dissolve, erode and/or absorb into the body with a selected time interval ranging from about 2 weeks to 52 weeks. In another embodiment, the biodissolvable portion can be disposed in an interior portion of the implant body, in a linear or helical configuration.

Figure 8A:
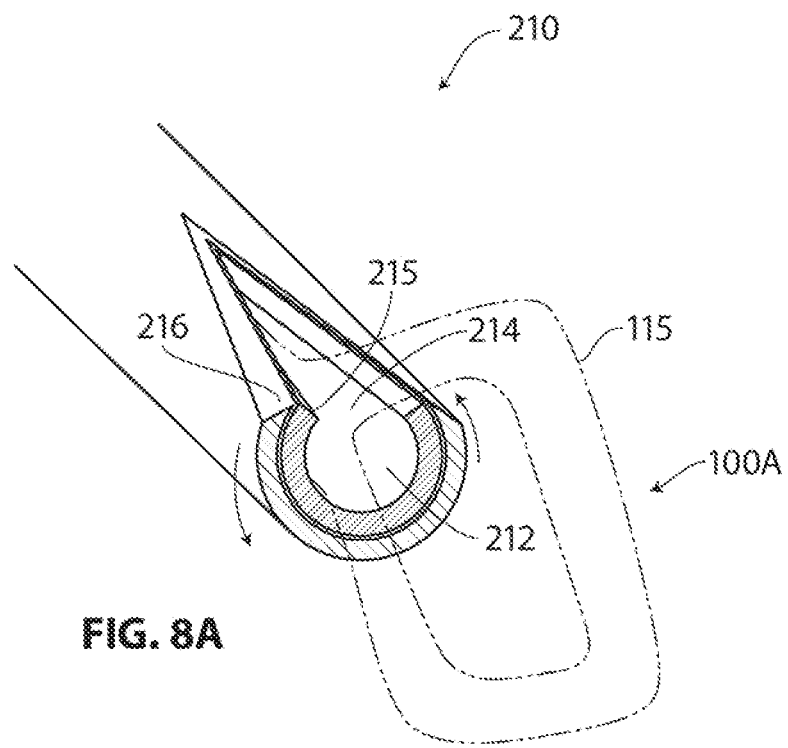
FIG. 8A depicts the working end of another embodiment of a cutting tool for cutting a portion of an implant in situ.
Figure 8B:
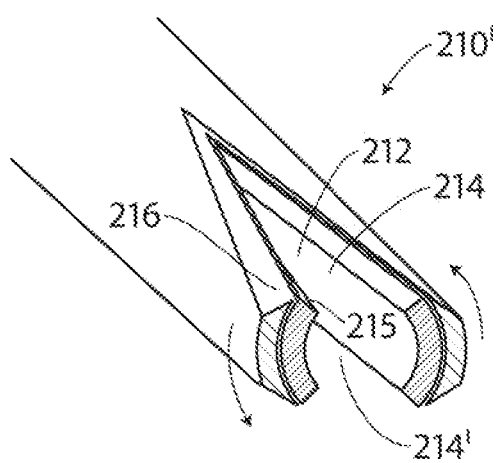
FIG. 8B depicts another embodiment of a cutting tool for cutting an implant in a revision procedure.

FIG. 8A depicts the working end 210 of an elongated tool that is adapted for cutting an end portion of an implant for its removal, for example an implant of FIGS. 3A-3D, 4, or 7A-7D. The tool functions similar to that of FIGS. 5A and 6, wherein the tool has a central bore 212 that receives the elongate medial portion of an implant body. As can be seen in FIG. 8A, the working end 210 includes two concentric hypotubes with a notch 214 therein to push over an end portion 115 of implant 100A of FIG. 3A, for example. The physician can counter-rotate the hypotubes from a proximal handle end wherein blade edges 215 and 216 of the working end function as a scissors mechanism to cut the implant body. Thereafter, the implant can be easily removed from the treatment site. FIG. 8B illustrates another working end 210' of a similar cutting tool that has opposing notches 214 and 214' that can receive a implant body portion and blade edges 215 and 216 can be rotated to cut the implant.

Figure 9:
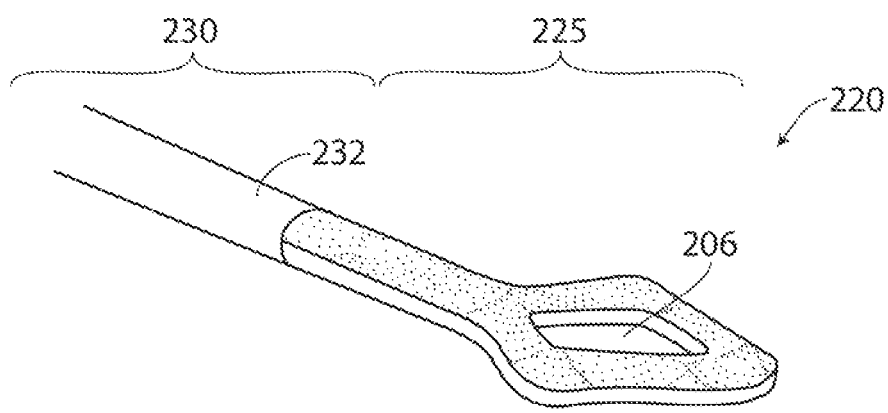
FIG. 9 depicts another implant with a medial portion having a surface configured for low adhesive energy.

FIG. 9 illustrates another embodiment of implant 220 that is similar to any previous embodiment except depicting a difference in surface characteristics of the implant. The end or encircling portion 225 may have smooth or slightly textured surface features and the medial portion 230 may comprise a highly lubricious surface, such as an elastomeric material having an ultra-hydrophobic surface 232 to allow for slippage of the tissue against the implant during use. Thus, a method of the invention comprises implanting a device in airway-interface tissue, securing first and second implant end portions in the tissue by permitting a tissue growth through at least one opening in an end portion, and allowing an elastomeric portion of the implant to apply retraction forces to alleviate tissue obstruction of the airway wherein an ultrahydrophobic surface of the implant prevents tissue adhesion to said surface. Ultrahydrophobic surfaces can be provided in a biocompatible polymer, as is known in the art.

In another aspect of the invention, referring to FIG. 9, the elongate implant body is configured for implanting in an airway-interface and at least a portion of a body surface has a wetting contact angle greater than 70, to prevent tissue adhesion and to allow tissue slippage. In other embodiments, at least a portion of a body surface has a wetting contact angle greater than 85, or greater than 100.

In another aspect of the invention, still referring to FIG. 9, the elongate implant body is configured for implanting in an airway-interface and at least a portion of a body surface has an adhesive energy of less than 100 dynes/cm, less than 75 dynes/cm or less than 50 dynes/cm.

Figure 10:
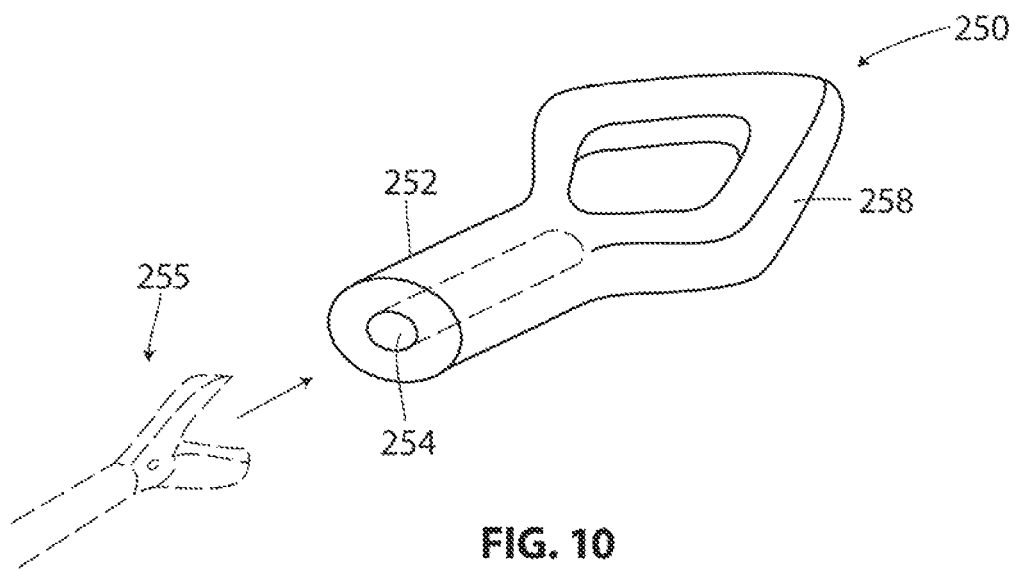
FIG. 10 depicts another elongate implant corresponding to aspects of the invention.

FIG. 10 illustrates another embodiment of revisable OSA implant 250 similar to previous embodiments except the medial portion 252 includes a passageway 254 configured for extending a cutting tool 255 through the passageway for cutting a distal end portion 258 of the implant. The passageway 254 can be accessed by an access opening in the opposing end (not shown) that can be identified by imaging of a marker, visual observation of a marker, by a left-in place guidewire or other suitable means or mechanism. The cutting tool 255 can comprise a scissor member, an extendable blade that is extendable from a blunt-tipped tool, any distal or proximally-facing blade, and/or any type of thermal energy emitter adapted for cutting the implant end 258.

Figure 11:
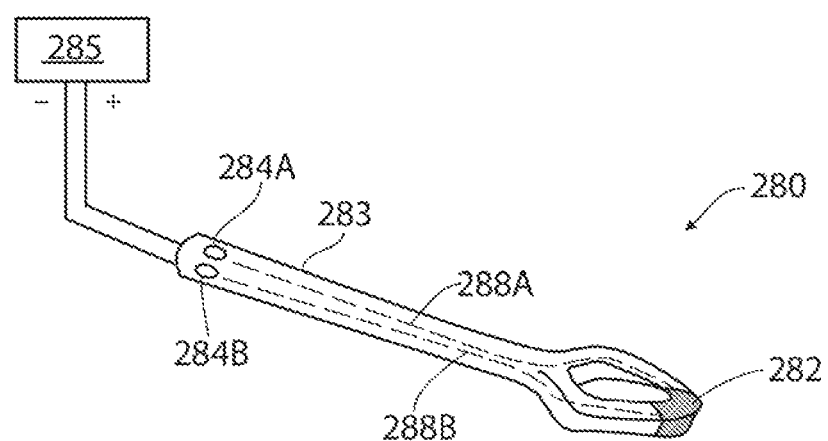
FIG. 11 depicts another implant corresponding to aspects of the invention including a sacrificial portion that can be sacrificed in response to an external stimulus.

FIG. 11 illustrates another embodiment of revisable OSA implant 280 that has a sacrificial portion indicated at 282 that can be severed or sacrificed by an external stimulus. In one embodiment, a medial portion 283 of the implant includes electrical contacts or extending leads 284A and 284B that can be detachably coupled to an electrical source 285. In FIG. 11, the implant body comprises an elastomeric material as described above and the sacrificial portion 282 comprises a conductively doped polymer portion that acts as a fuse when subject to a very short burst of high voltage RF current. Opposing sides or aspects of the sacrificial portion 282 are coupled to electrical leads 288A and 288B that are embedded or molded into the implant. The use of such doped polymers for a fuse-effect for detachment of endovascular medical implants is disclosed in U.S. Pat. No. 6,458,127 to Truckai et al and issued Oct. 1, 2002, which is incorporated herein by reference. Similar doped polymers can be used in the revisable OSA implant of FIG. 11.

FIG. 12 illustrates a method of using the OSA implant 280 of FIG. 11, and more particularly for revising the treatment.

FIG. 12 depicts that an RF current from source 285 has been delivered to melt, sever and sacrifice portion 282 of the implant thus allowing extraction of the implant from around the tissue plug.

FIGS. 13A and 13B illustrate another embodiment of revisable OSA implant 290 that has a sacrificial portion indicated at 282 in a medial portion of the implant that can be actuated and sacrificed by the external stimulus which then leaves the encircling portion 115 of the implant in place. The left-in-place portion of the implant can be used as an anchor for subsequent implants. In one embodiment as in FIGS. 13A-13B, the sacrificial portion 282 can comprise an electrolytic wire that can be sacrificed over a short time interval by direct current as is known in the art. Such electrolytic wire for detachment of embolic coil implants are known in the field of aneurysm implants and treatments.

While FIGS. 11-13B show OSA implants with two forms of sacrificial portions, it should be appreciated that similar implants can have sacrificial portions that are cut, severed or sacrificed by any external stimulus such as RF current, DC current, light energy, inductive heating etc. and may fall within the scope of aspects of the invention.

Figure 14:
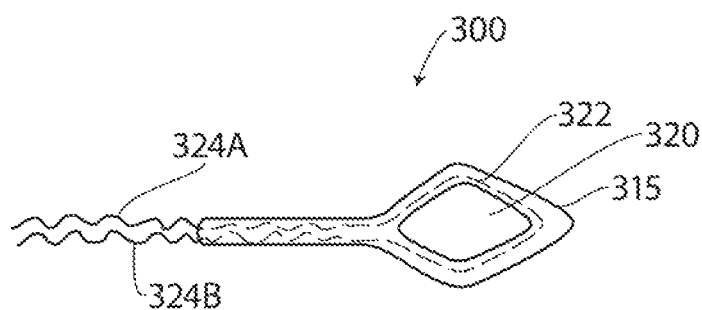
FIG. 14 depicts an end portion of an alternative revisable implant including a cut wire for cutting a tissue plug.
Figure 15:
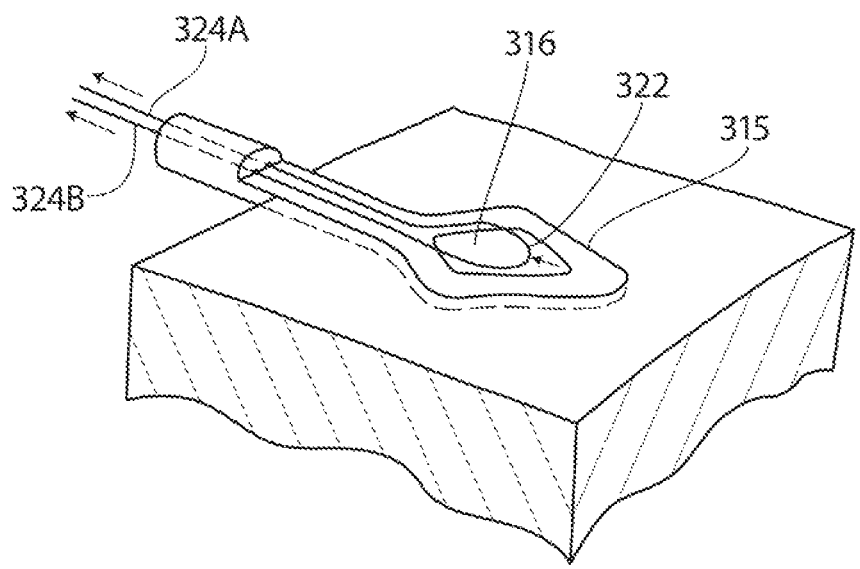
FIG. 15 is a cut-away view depicting the implant of FIG. 14 in a tissue site in the process of actuating the cut wire.

FIGS. 14 and 15 illustrate another embodiment of revisable OSA implant 300 that again includes at least one end with an encircling portion indicated at 315 that encircles a tissue plug 316 that grows through an opening 320. In one embodiment, the implant carries a cut wire 322 that extends in a loop with first and second wire ends 324A and 324B extending through one or more passageways in the implant. The cut wire 322 can be embedded in the surface of the implant surrounding the opening 320. As can be seen in FIG. 15, the looped cut wire 322 can be pulled proximally to cut the tissue plug 316 which then will free the implant from its attachment. In FIG. 14, it can be seen that the cut wire ends 324A and 324B can have a serpentine configuration in the medial portion of the implant so as to not interfere with the tensioning and relaxation of the elastomeric medial implant portion during its use. When the cut wire is accessed and pulled relative to the implant 300, the tissue plug 316 can be cut. It should be appreciated that other tools (not shown) may be used to stabilize the implant when actuating the cut wire as in FIG. 15. The cut wire 322 can be any form of fine wire, or abrasive wire or a resistively heated wire coupled to an electrical source (not shown).

Figure 16:
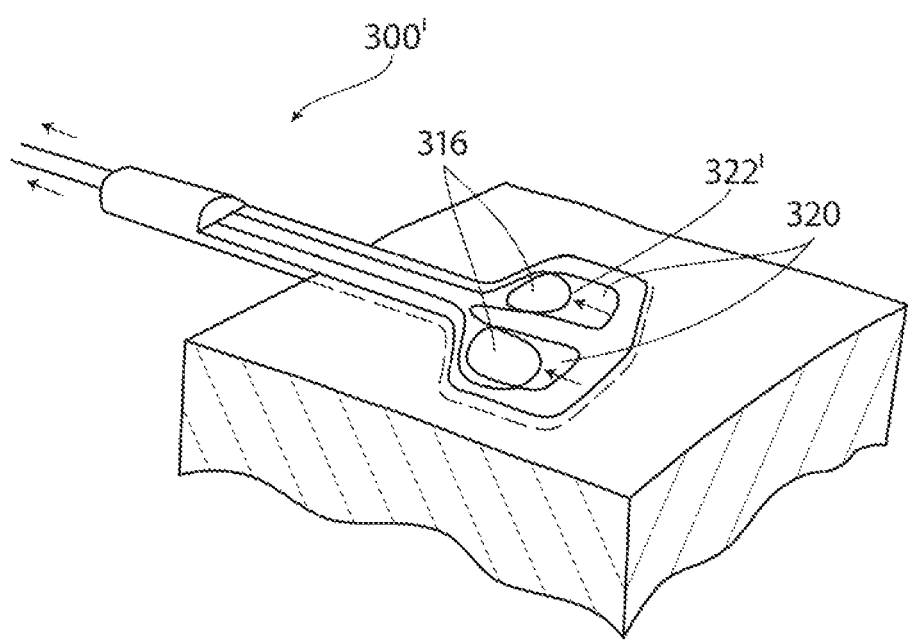
FIG. 16 depicts an end portion of an alternative revisable implant including a cut wire for cutting a plurality of tissue plugs.

FIG. 16 depicts another revisable OSA implant 300' that is similar to that of FIGS. 14-15 with the cut wire 322' configured to cut a plurality of tissue plugs 316 that have grown through openings 320 within an encircling end portion of the implant body.

Figure 17:
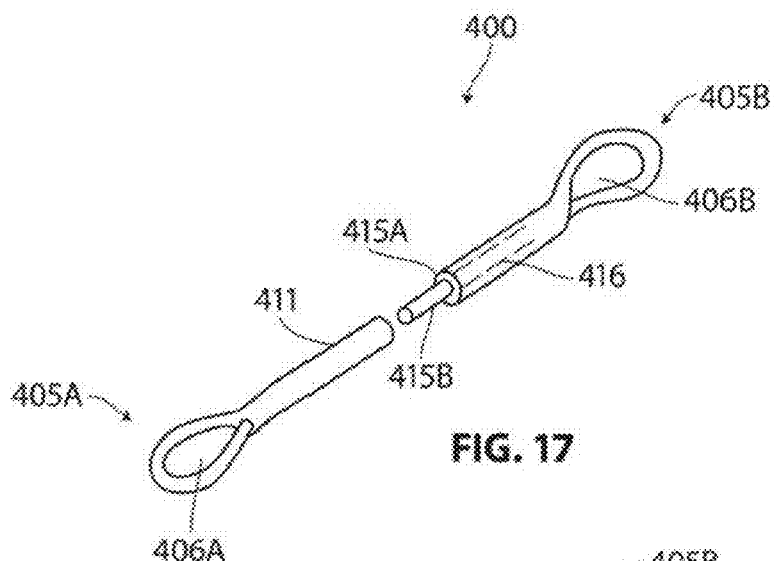
FIG. 17 depicts an alternative revisable OSA implant.

FIG. 17 depicts another OSA implant 400 that is adapted for revision as previous implants and systems wherein the elongate device or implant body has first and second end portions 405A and 405B with through-openings 406A and 406B therein. The medial portion 411 of implant body 400 extends about an axis and comprises a biocompatible elastomeric material such as a silicone. In this embodiment, the medial portion comprises first and second extending portions 415A and 415B wherein one such portion can be nested in a passageway 416 of the other portion and then form proximal and distal loops or encircling end portions that define openings 406A and 406B for receiving tissue plugs therein. As can be understood from FIGS. 17 and 18A, both the extending portions 415A and 415B comprise an elastomeric material and thus combine to provide the desired retraction forces of the OSA implant.

Figure 18A:
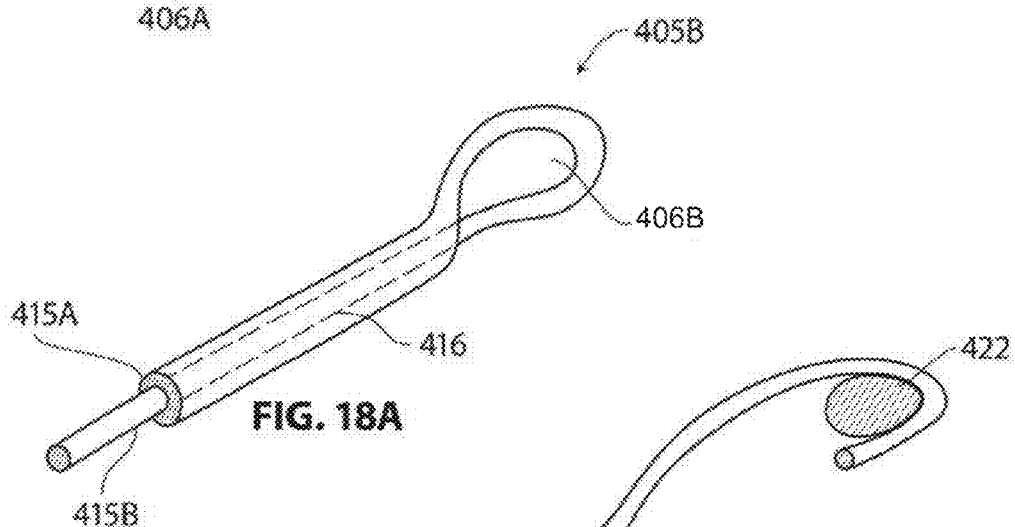
FIGS. 18A and 18B illustrate an end portion of the revisable implant of FIG. 17.
Figure 18B:
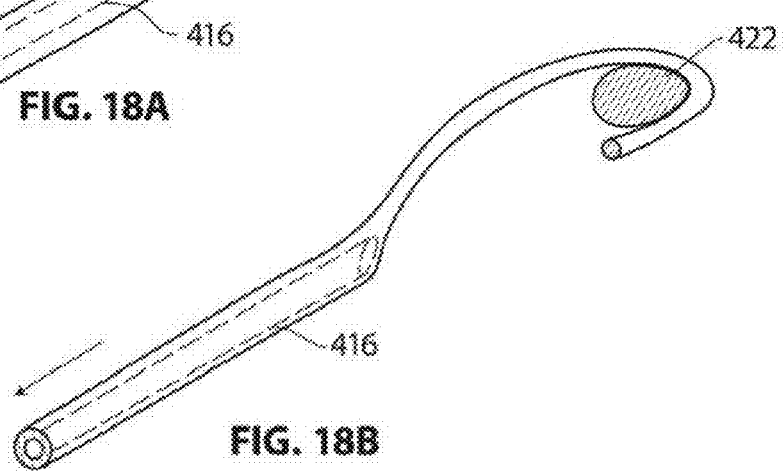

Referring to FIGS. 18A and 18B, it can be seen that if the second extending portion 415B is cut in a medial or proximal aspect of the implant, or if both the first and second extending portions 415A and 415B are cut in a proximal or medial aspect, then a proximal aspect of the first or outer extending portion 415A can be pulled in the proximal direction and the cut second extending portion 415B then will snake out of the path around the tissue plug 422. Thus, the implant can be cut in a proximal or medial aspect and can be withdrawn from the treatment site from a remote access location.

Figure 19:
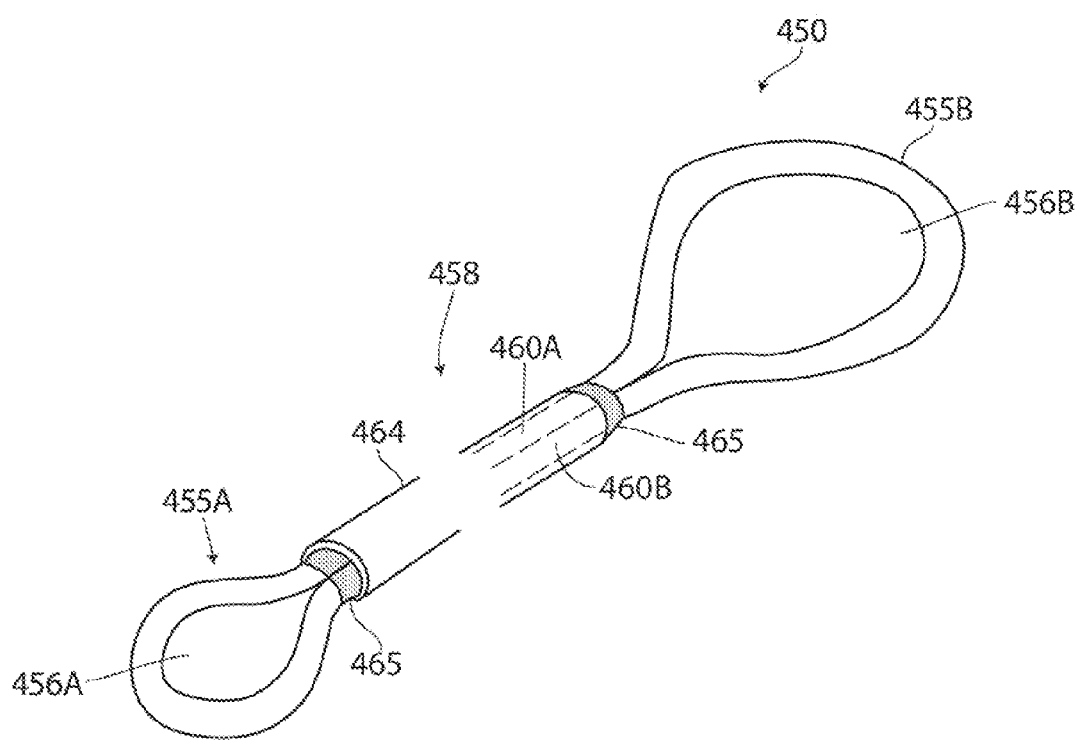
FIG. 19 depicts an alternative revisable OSA implant.

FIG. 19 depicts another OSA implant 450 that is adapted for a revision procedure and comprises an elongate implant body with first and second end portions 455A and 455B with through-openings 456A and 456B therein. This embodiment is similar to that of FIG. 17 in that medial portion 458 includes extending portions 460A and 460B comprising an elastomeric material that combine to provide the desired retraction forces of the OSA implant. The extending portions 460A and 460B are carried in a thin elastomeric sleeve 464 that has tear-away portions 465 about its ends to prevent tissue ingrowth into the passageway in the sleeve. It can be understood that by cutting the medial portion of the implant, and then pulling on an end of an extending portion 460A or 460B will cause the other free end of the implant to snake around the tissue plug similar to the method depicted in FIG. 18B. Both ends of the implant can be removed from the treatment site by this method.

C. In-Situ Adjustable Force OSA Implants

Another type of OSA implant includes means for in-situ adjustment of force applied by the implant after implantation in the treatment site. Such an adjustment can increase or decrease the applied forces applied to the treatment site by the implant. Such adjustment of forces applied by the implant typically may be performed upon specific event, such as periodic evaluations of the treatment. The adjustment also can be done at a pre-determined schedule, based on an algorithm, or can be random. In one example, the patient may gain or lose weight which could result in a need for adjusting the forces applied by the implant. Other influences can be a worsening of the patient's condition, the aging of the patient, local tissue remodeling around the implant, age of the implant or degradation of material properties of the implant. In some embodiments described below, an implant system can be provided that is easily adjustable in-situ between first and second conditions on a repetitive basis, for example, that can be adjusted for sleep interval and for awake intervals on a daily basis. Such an adjustable embodiment can thus deliver tissue-retraction forces only when needed during sleep. One advantage of such an embodiment would be to allow the tissue of the treatment site to be free from implant-generated retraction forces during awake intervals to prevent or greatly limit the potential of tissue remodeling due to a continuous application of such retraction force.

Figure 20:
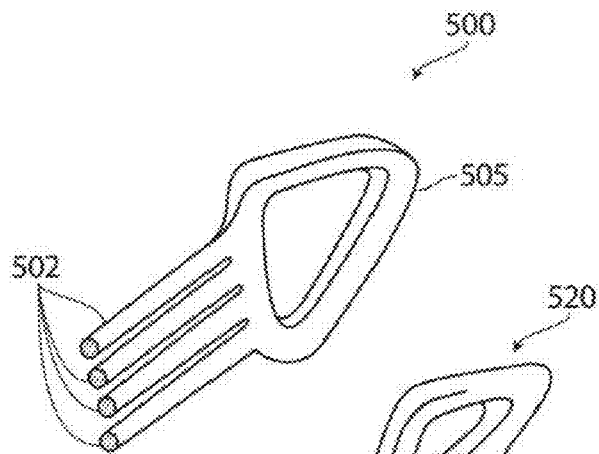
FIG. 20 depicts a revisable OSA implant that allows for in-situ post-implant adjustment of the retraction forces applied to tissue by the implant.

FIG. 20 depicts a revisable OSA implant 500 that is adapted for minimally invasive in-situ post-implant adjustment of retraction forces applied by the implant. In this embodiment, the implant is configured for a downward adjustment of retraction forces applied by the OSA implant. In FIG. 20, it can be seen that the elongate implant body has a plurality of extending elements 502 coupled to end portion 505, wherein the elements 502 can be individually cut to reduce the applied retraction forces of the implant. The number of extending elements 502 can range from 2 to 20 or more.

Figure 21A:
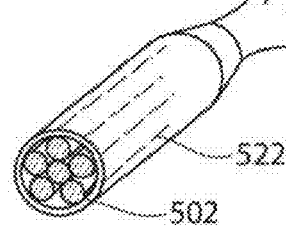
FIGS. 21A and 21B depict an alternative revisable OSA implant that allows for in-situ post-implant adjustment of the retraction forces.
Figure 21B:
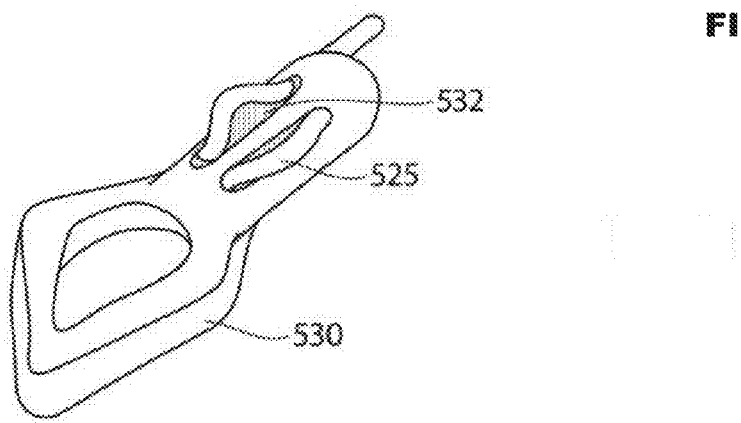

FIG. 21A depicts a revisable OSA implant 520 that functions as the previous embodiment except that the plurality of extending elements 502 are housed in thin-wall elastomeric sleeve 522. Further, an axial portion 525 of some or each extension element 502 protrudes outward from sleeve 522, or an end portion 530 of the implant, shown in FIG. 21B, to allow such a portion to be cut. Soft filler or "tear away" material 532, such as a very low modulus silicone, may be provided around each extension element 502 where it protrudes from sleeve 522 to prevent tissue ingrowth into the interior channels of the device. In use, a physician is able to pick up the elastic element 502 and cut it, and filler material 532 just tears away in the process. Again, any form of cutting tool can be used for minimally invasive access to cut an elastomeric element to titrate retraction forces in a downward direction.

Figure 22:
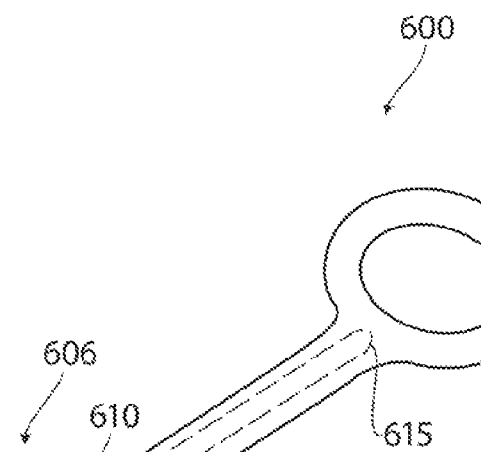
FIGS. 22 and 23 depict another revisable OSA implant that allows for in-situ post-implant adjustment of the retraction forces.
Figure 23:
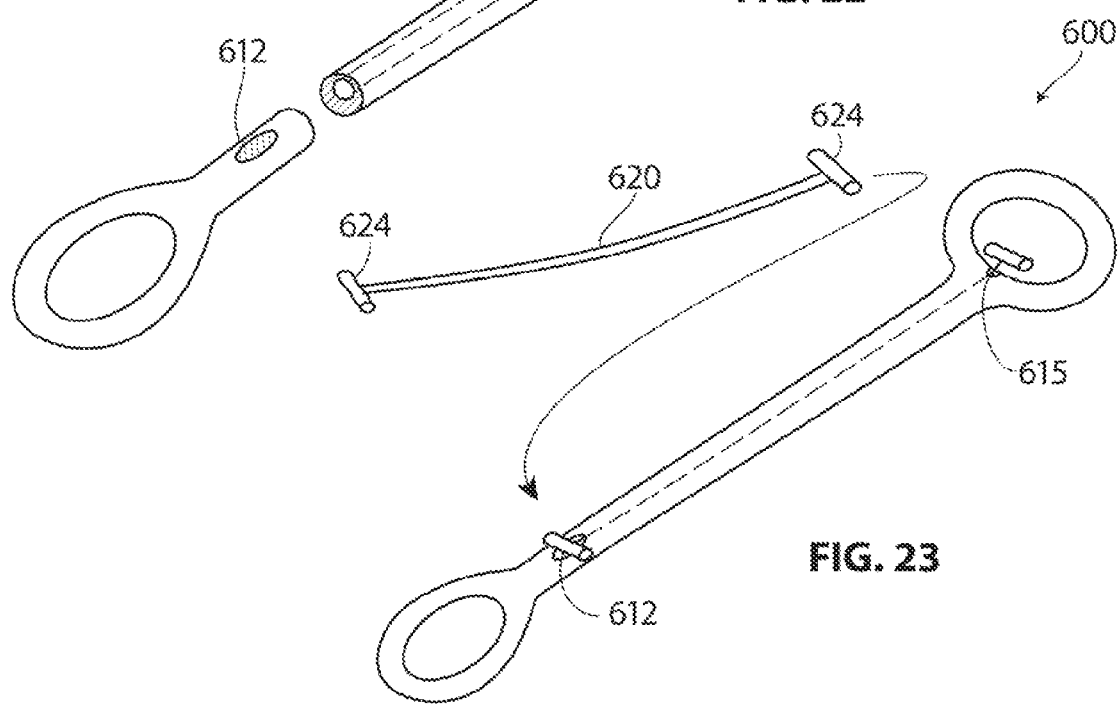

FIG. 22 depicts an OSA implant 600 that is adapted for in-situ post-implant adjustment of retraction forces applied to targeted tissue. In one method, assume that it is desirable to increase the applied retraction forces over time due to tissue remodeling wherein greater retraction forces are desired. In FIG. 22, the elongated implant body has a medial portion 606 that includes an interior channel 610 that extends from an accessible first end 612 to a remote end 615. Each end 612 and 615 can include a silicone membrane to prevent tissue ingrowth but will allow a needle to be inserted therethrough. The channel ends 612 and 615 can be disposed in more rigid end portions of the implant, wherein the medial portion of the implant body comprises an elastomer to provide the desired retraction forces. In one embodiment, the channel 610 is dimensioned to collapse or flatten but can also accommodate the insertion of at least one additional elastomeric element indicated at 620. It can be understood from FIG. 23 that an elastomeric element 620 with end-toggles 624 be inserted in a bore of a flexible needle member (not shown) and inserted through the channel in the implant so that the toggles are released to deploy the element 620 in a tensioned position to thereby add to the retraction forces applied to tissue collectively with the medial portion 606 of the implant 600. In a similar manner, an end of the implant 600 and/or elastomeric element 620 can be clipped to reduce the applied retraction forces as in the system and method depicted in FIGS. 20 and 21.

Thus, in general, the system and implants of FIGS. 20-23 corresponding to aspects of the invention comprise an elongate implant sized and shaped to conform to an airway-interface tissue site in a manner compatible with normal physiological function of the site, a medial portion of the implant comprising an elastomeric material configured to apply retraction forces to the site, and adjustment means for in situ adjustment of retraction forces applied by the implant.

D. OSA Implants for Applying Non-Aligned Displacement Forces

Figure 24:
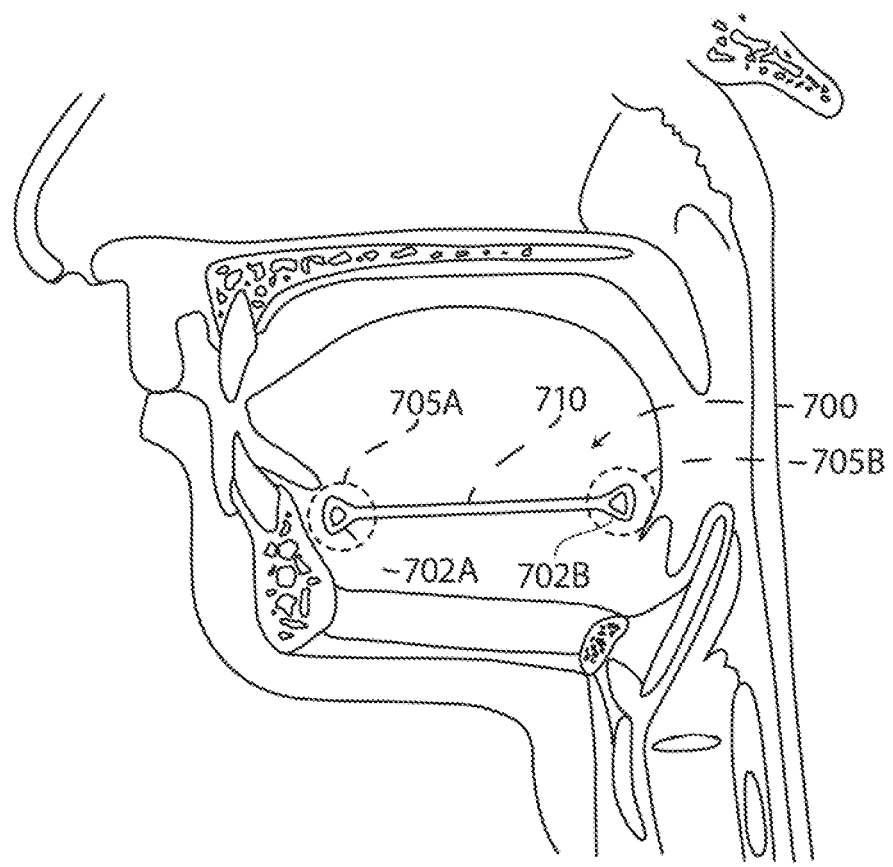
FIG. 24 depicts an OSA implant with first and second anchoring ends implanted in a particular site in a patient's tongue.
Figure 25:
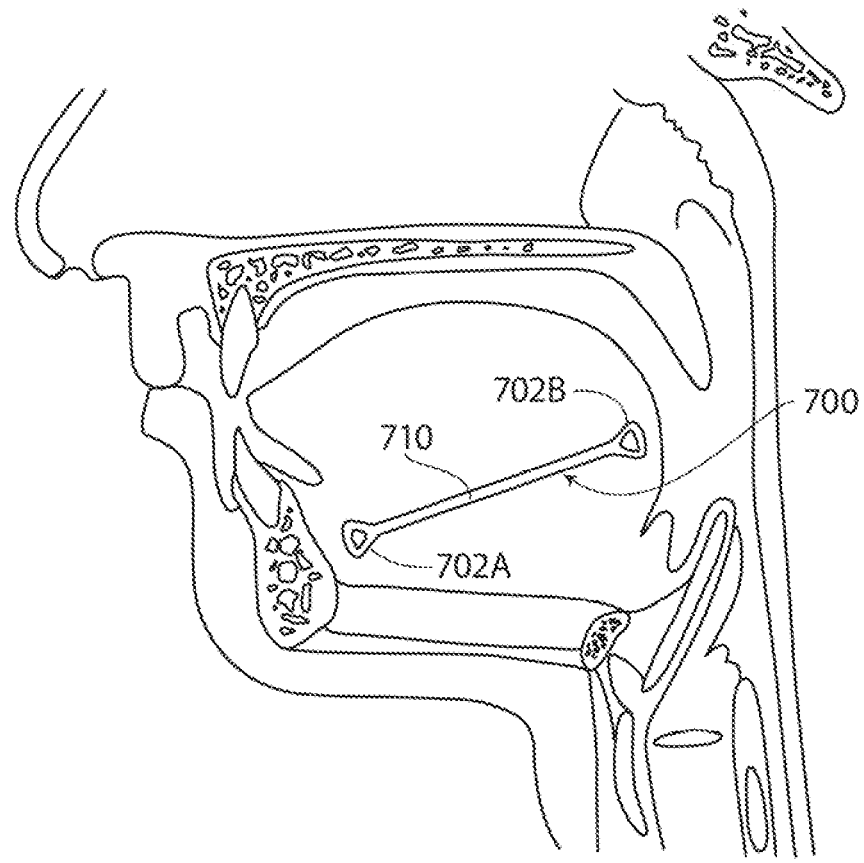
FIG. 25 depicts the OSA implant of FIG. 24 implanted in another particular site in a patient's tongue.

Another aspect of the invention can be described with reference to FIG. 24-27B, wherein a resilient implant (or implants) can be positioned in airway-interface tissue to apply tensile forces or displacement forces in at least two non-aligned or separate directions or vectors. These can be referred to as distinguishable vectors. In a typical embodiment depicted in FIGS. 24-25, an implant 700 corresponding to aspects of the invention can form a linear structure wherein two anchor ends 702a and 702b form anchor points or regions 705a and 705b in the tissue. Such points 705a and 705b are connected by a straight or substantially straight elastic portion 710 or spring element of the implant such that said elastic portion or spring element applies a tensile force and/or a tensile displacement between said anchor points 705a and 705b. In the embodiment of FIG. 24, the implant 700 acts to apply forces and/or displacements between the said anchor points 705a and 705b to displace and/or apply forces to the patient's tongue, but it should be appreciated that an appropriately dimensioned implant can also or instead be introduced into the soft palate or pharyngeal structures adjacent to the patient's airway. FIG. 25 illustrates the implant 700 can have various orientations in the tissue. Now turning to FIGS. 26-27B, it can be seen that a plurality of substantially linear elastic implants 700 similar to that of FIGS. 24-25 can thus provide a plurality of tissue anchor points 715 wherein the elastic or spring portion 710 of the implants function in such a manner to provide tensile or displacement forces to achieve the desired clinical effects. Testing in animal models has indicated that forces applied to the subject's tongue by two implants in two different directions may improve implant performance when compared with unidirectional application of forces from a single implant.

Figure 28A:
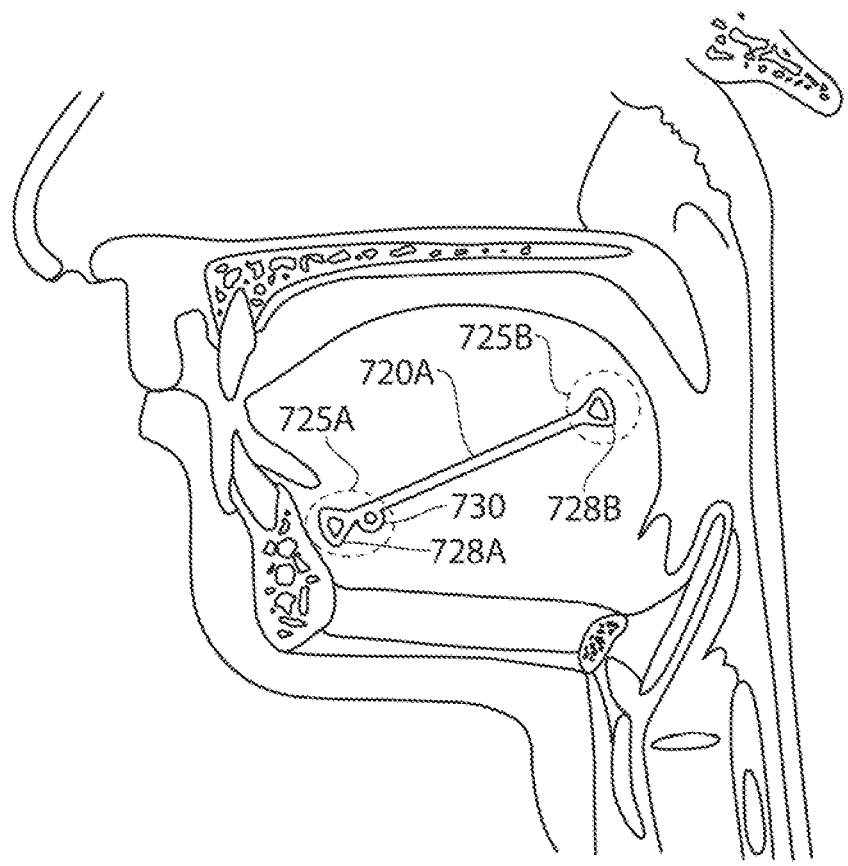
FIGS. 28A, 28B and 28C depict another OSA implant system for applying linear-directed forces in different distinct vectors with individual implant bodies coupled together in-situ with attachment means.
Figure 28B:
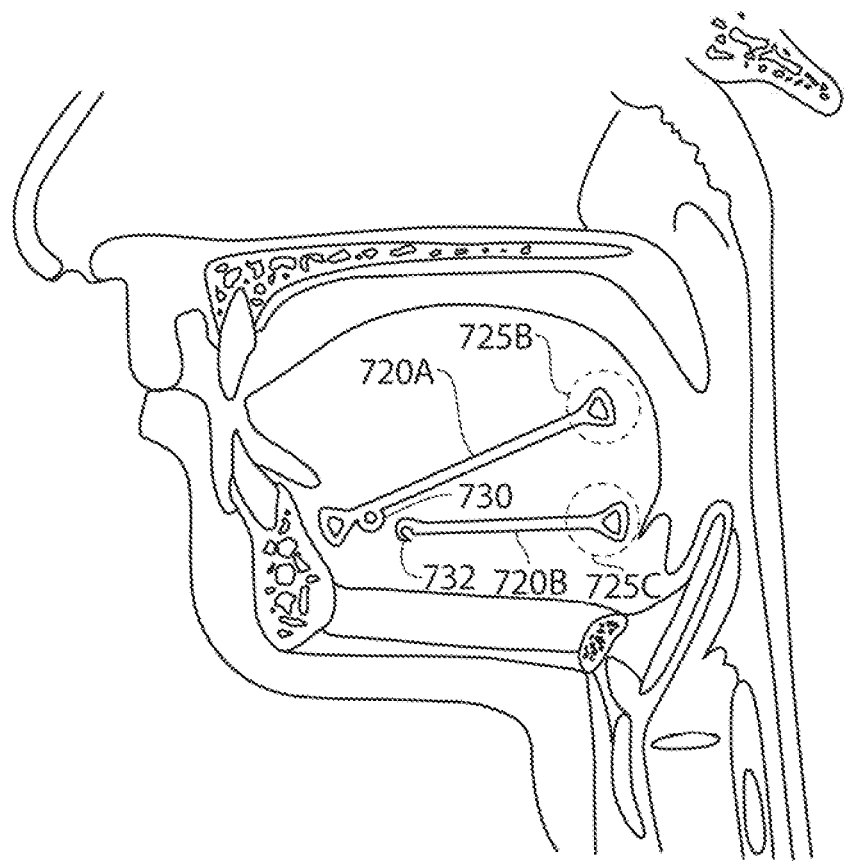
Figure 28C:
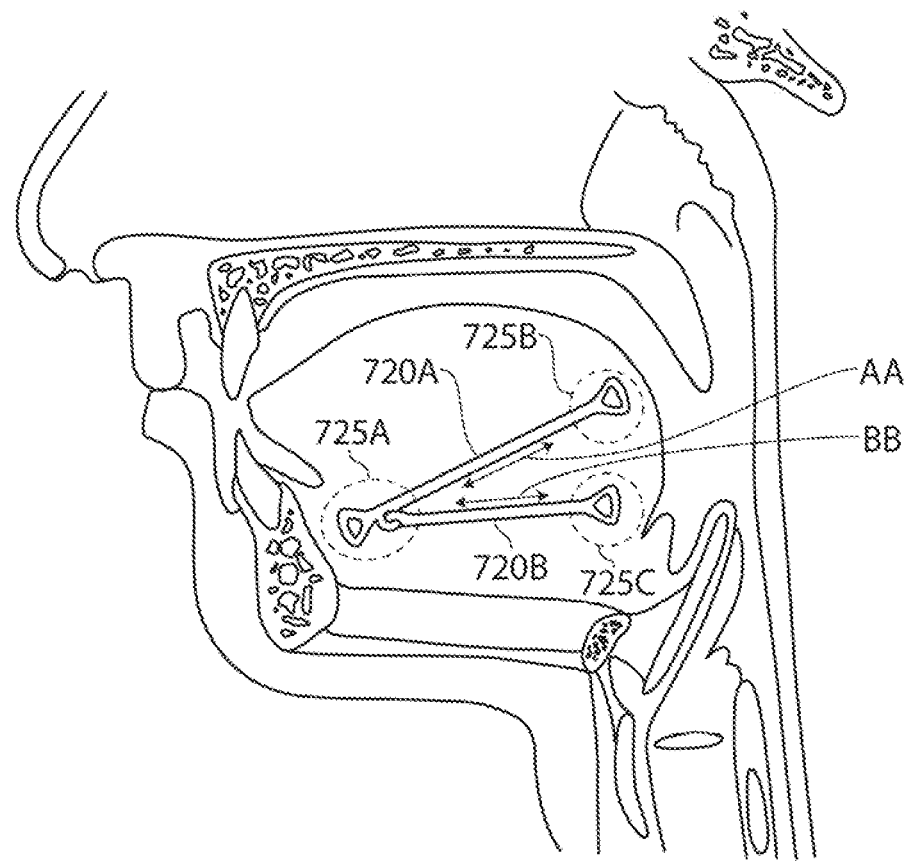

FIGS. 28A-28C schematically illustrate another embodiment of implant system according to aspects of the invention that comprises first and second elastic elements 720A and 720B that provide three anchor points in tissue indicated at 725a, 725b and 725c. FIG. 28A depicts the implantation of the first elastic element 720A which has anchoring ends 728a and 728b as described above, wherein at least one end is configured with an attachment element such as a loop 730 that is connectable with a hook element 732 of a second elastic element 720B. Thus, FIGS. 28A and 28B depict the steps of implanting the elastic elements, wherein elastic element 720A is initially implanted in its desired location as shown in FIG. 28A. Then, FIG. 28B depicts elastic element 720B being positioned in its desired location such that the hook 732 is adjacent to loop 730 of the elastic element 720A. FIG. 28C then depicts the loop 730 and hook 732 be connected in such a manner so as to produce a fixed-link implant structure which thus applies forces in two non-aligned vectors AA and BB. It can be understood that the implants can be implanted in sequence and then coupled in situ to form a V-shaped implant system. It should be appreciated that the implant structure of FIGS. 28A-28C can have components such as elastic or spring elements that can be connected prior to, during, or following implantation by means of adhesives, connectors, snap-fit features, hooks and loops, clamps, ratchets, keyed fittings, etc., or by means of separate attachment, such as sutures, junctions, clamps, or other connection means. In another embodiment, two end portions of separate implant bodies can be disposed proximate to one another, and the body's fibrotic response or wound healing response can cause a connection of the two implant ends.

Figure 29A:
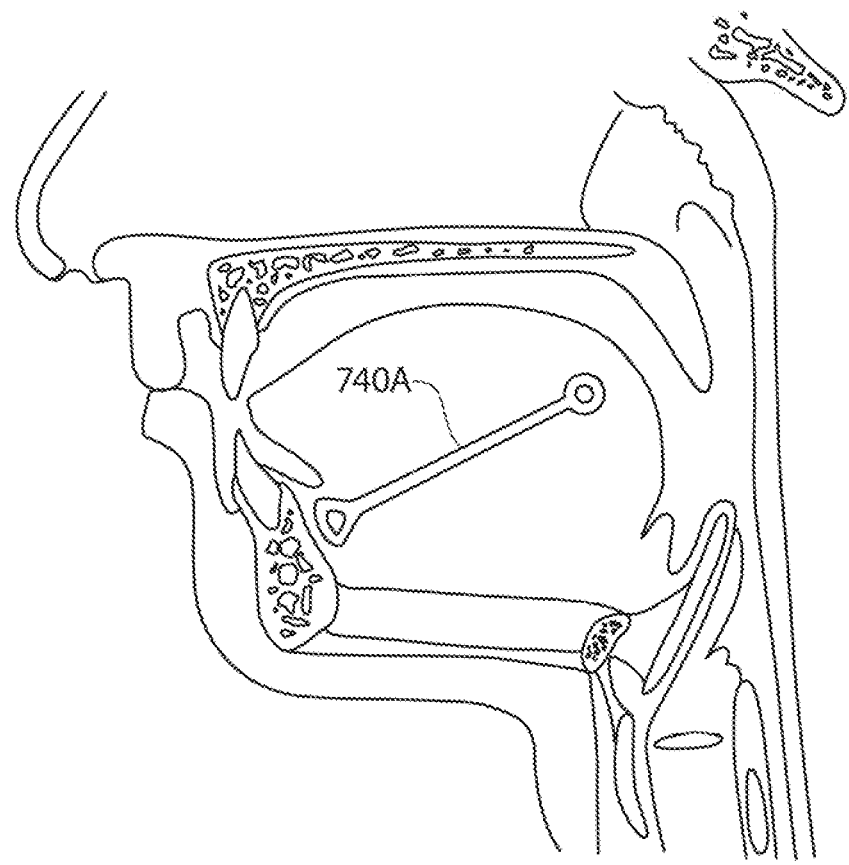
FIGS. 29A-29B depict another OSA implant system similar to that of FIGS. 28A-28C for applying linear-directed forces in different distinct vectors in a different orientation.
Figure 29B:
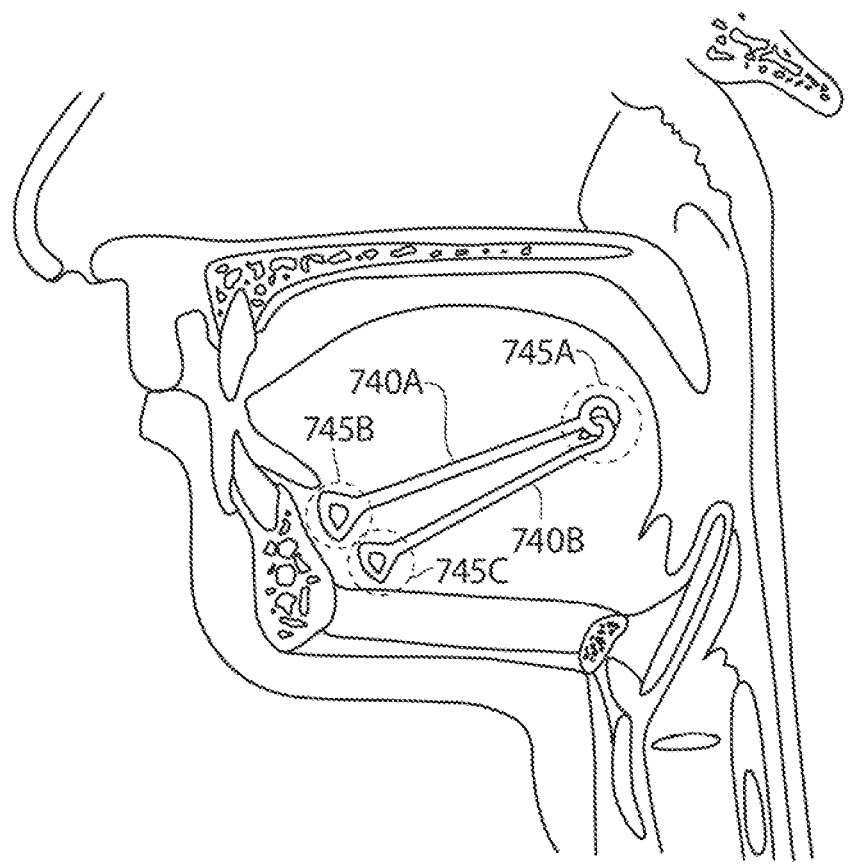

FIGS. 29A-29B schematically illustrate another embodiment of implant system comprising first and second elastic elements 740A and 740B in a different orientation in a patient's tongue. Each implant has an elastic medial section as described above. The implant system again provides three anchor points 745a-745c as shown in FIG. 29B, wherein the first implant can be fixedly attached to the second implant by loop and hook features or other similar means. As described previously, the implants can be implanted in sequence and then coupled in situ to form the V-shaped implant system. In some embodiments, the angle between the legs of the V-shaped implant ranges from about 10° to about 90° depending on the implant site. In other embodiments, the angle between the legs of the V-shaped implant ranges from about 10° to about 170°. The lengths of the legs of the V-shaped implant can vary, as well as the forces applied by each leg of the V-shaped implant.

In general, when the implants of the disclosure as described above are implanted in the tongue and/or the palate of the patient (FIG. 35), the positioning of the implants will affect the location and direction of the applied forces and the displacements of the surrounding tissues. The implants may be placed in various locations to achieve the desired clinical effects, and may be specifically tailored to an individual patient based on the nature and details of each patient's OSA, including their specific anatomy and physiology. For example, if a patient suffers obstructions associated with the lower posterior region of the tongue impinging on the posterior pharyngeal wall, then an implantation location that places one end of a linear implant lower in the tongue may be appropriate (see FIG. 24). In another example, if the patient suffers obstructions associated with the upper posterior region of the tongue impinging on the posterior pharyngeal wall, then an implantation location that places one end of a linear implant higher in the tongue may be more appropriate (see FIG. 25). In a similar manner, the implants of the disclosure may be placed in various locations within the tongue and soft palate, utilizing one or more implants, to address the specific needs of the patient and to achieve the desired clinical effects.

In general, a method according to aspects of the invention for treating an airway disorder comprises implanting at least one elastic implant in airway-interface tissue wherein the at least one implant is configured to apply tensile forces to the tissue in at least two non-aligned directions or vectors. The non-aligned vectors thus describe the linearly-directed forces applied to tissue by substantially linear, elongated implants disposed in the tissue, such as vectors AA and BB in FIG. 28C.

In one aspect of the method, the linearly-directed forces can be applied to tissue in the non-aligned vectors by a single implant configured with first and second body portions that extend in-between different anchoring sites (see FIG. 35). In another aspect of the method, at least first and second implants can be implanted to apply such forces in at least first and second non-aligned vectors. In any implant embodiment, the elongated elastic body portions can cooperate with bioreodible materials that temporarily maintain the implant in an extended position as described above. Further, as described previously, the targeted airway-interface tissue which receives the implant can comprise the patient's tongue, soft palate and/or pharyngeal tissue.

Now turning to FIGS. 30-34, various aspects of the invention are described that relate to placement of the implants within the tongue or soft palate of the patient. Implantation may be achieved in a variety of manners, and typically is accomplished by the insertion of a needle-based cannula 760 as shown schematically in FIG. 30. It should be appreciated that an open surgery or other minimally invasive surgical technique can be used. In one embodiment of sharp-tipped cannula 760 shown in FIG. 31, the implant body 770 is carried in bore 772 of the cannula. A thin push rod or stylette member 775 has a distal end 777 that releaseably engages a distal portion 778 of the implant body. The engagement can comprise a hook or other attachment means for coupling with the distal end of the implant body. The stylette 775 can reside in the cannula bore 772 alongside the flexible implant body in such a manner that when said stylette is pushed, the distal end of the stylette functions to pull or deploy the implant 770 through said cannula, avoiding any jamming or bunching of said implant during deployment. Further, the implant can be deployed in the targeted tissue site in a fully elongated (i.e. non-bunched) fashion. In another aspect of the method, the cannula is introduced into the targeted site, and thereafter the physician maintains the stylette 775 in a fixed position and contemporaneously withdraws the cannula 760 to thus deploy the implant body 770 in the targeted site.

Figure 30:
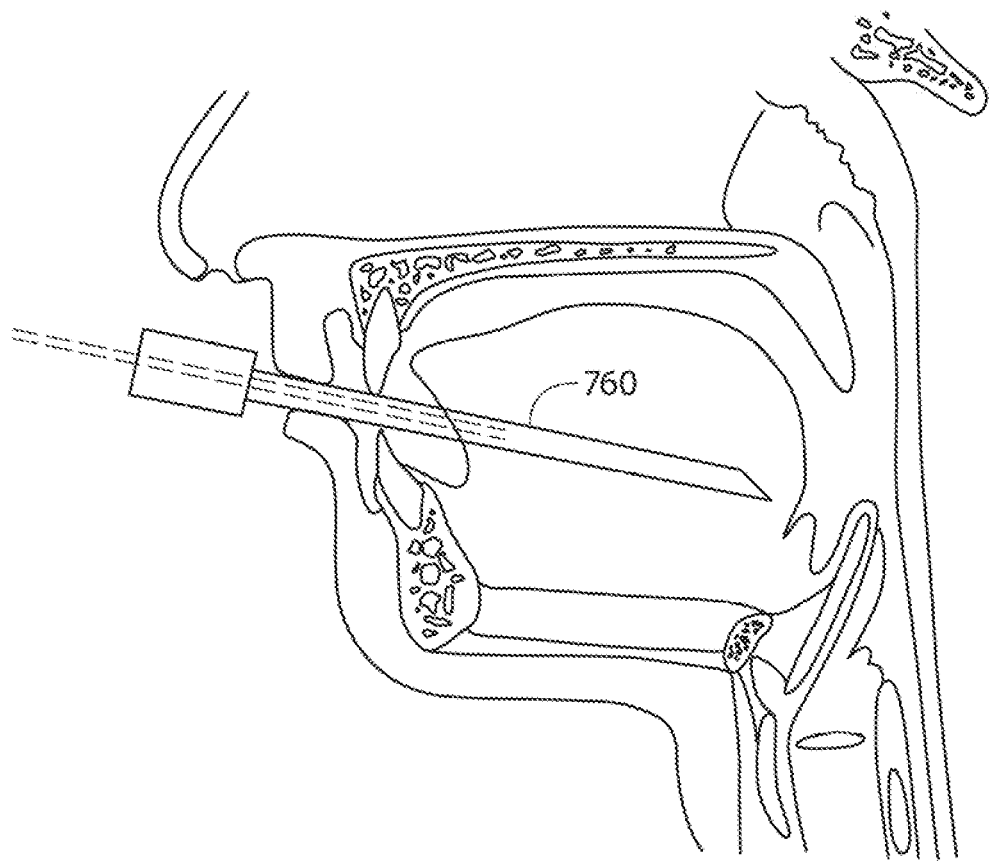
FIG. 30 illustrates a method of utilizing a cannula apparatus for deployment of an OSA implant as in FIG. 24 in a particular site in a patient's tongue.
Figure 31:
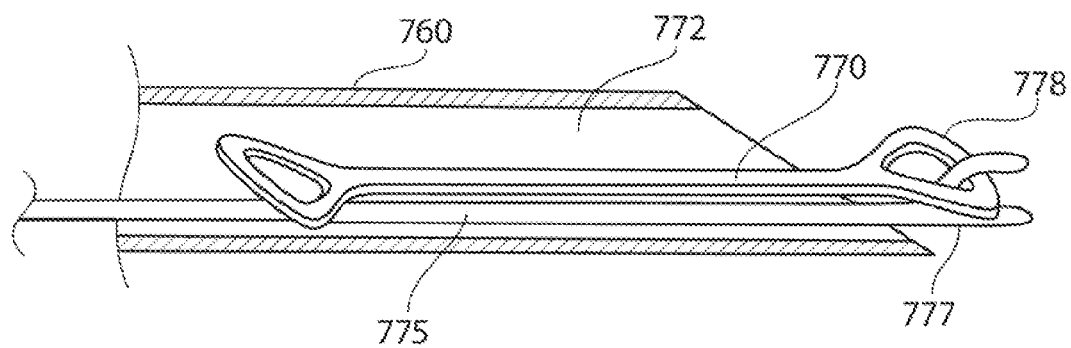
FIG. 31 illustrates a working end of the cannula apparatus of FIG. 30 together with a push rod or stylette mechanism for deployment of the OSA implant of FIG. 24.
Figure 32A:
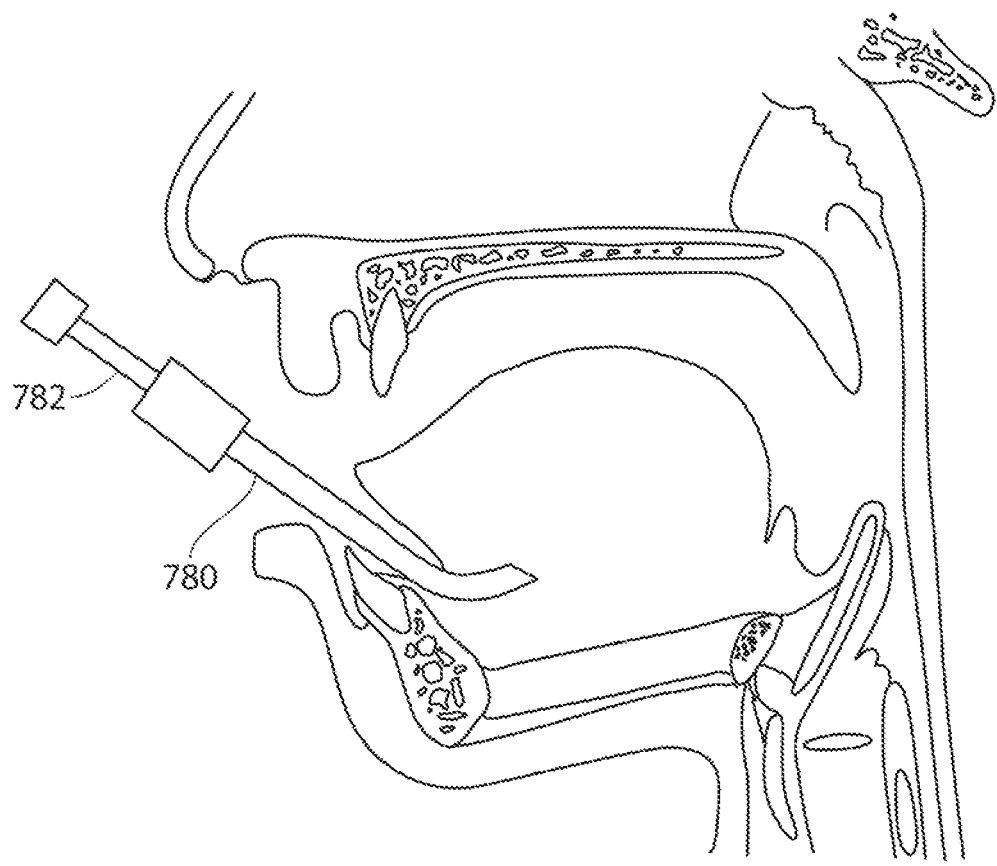
FIGS. 32A-32B illustrates a method of utilizing an alternative telescoping cannula apparatus for deployment of an OSA implant at a selected angle in a patient's tongue.
Figure 32B:
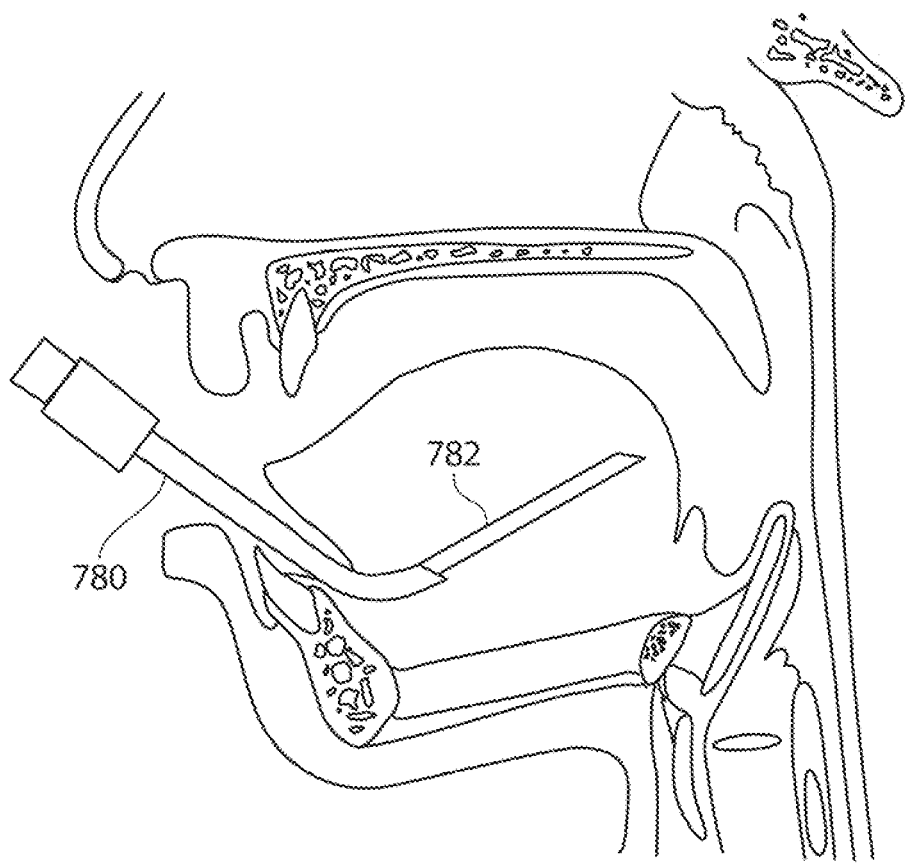
Figure 33:
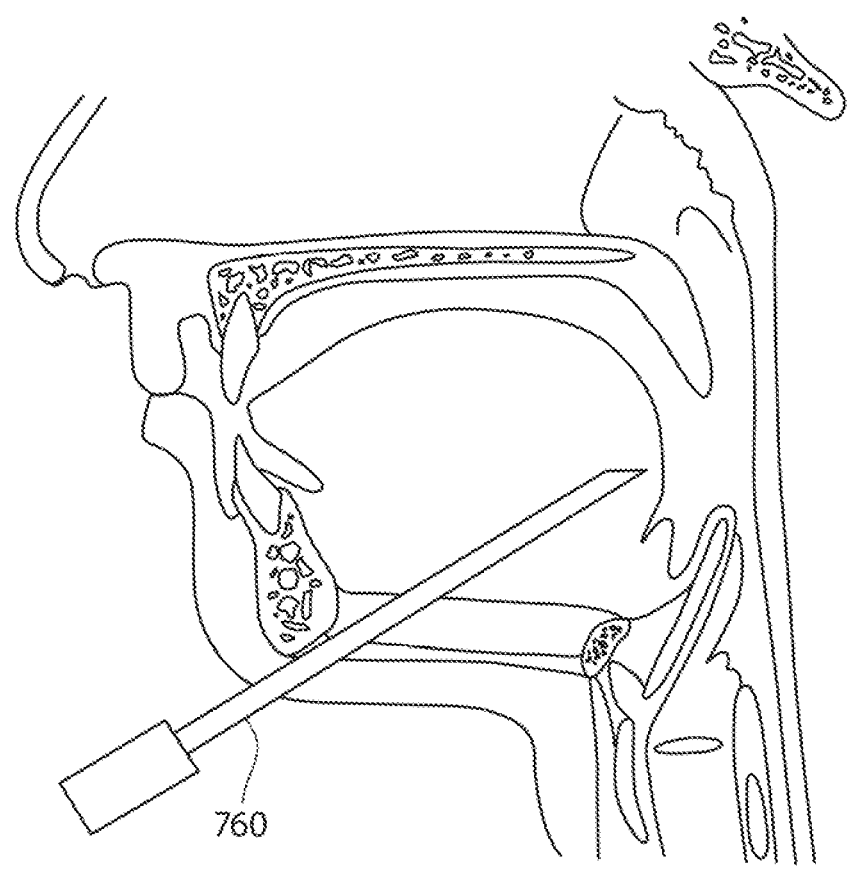
FIG. 33 illustrates another method of utilizing a cannula apparatus to penetrate through a patient's skin for deployment of an OSA implant in a patient's tongue.
Figure 34:
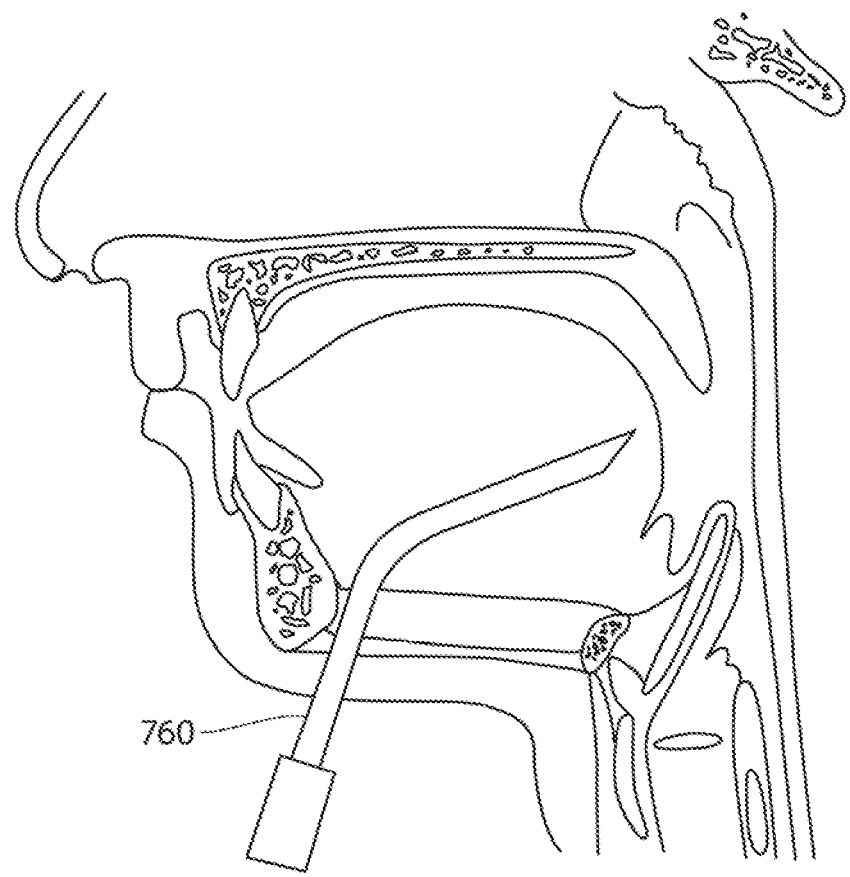
FIG. 34 illustrates another method of utilizing a curved cannula apparatus for deployment of an OSA implant in a patient's tongue.

The disclosed implants may be placed within the tongue by means of straight, curved, articulating, deformable and/or telescoping cannulas 760 as in FIGS. 30-34, which may be introduced through any access points described above. The route of access to the implantation site within the tongue may include access via a sublingual location as depicted in FIGS. 30 and 32A-32B, (within the oral cavity, below the anterior portion of the tongue), access via a submandibular location as depicted in FIGS. 33-34 (below the anterior portion of the mandible), access via a posterior lingual location (on the posterior surface of the tongue) or any other access point that may allow for proper implant positioning.

The route of access to the implantation site within the soft palate may include access via an intra-oral location (within the oral cavity adjacent to the junction of the soft palate and the hard palate) or an intra-nasal location (within the nasal cavity adjacent to the junction of the soft palate and the hard palate), or any other access point along the soft or hard palate that may allow for proper implant positioning.

In one example, FIG. 30 shows a straight cannula inserted in the sublingual location, resulting in a substantially straight placement with the anterior anchor located adjacent to a superior part of the mandible. In another example, FIGS. 32A-32B depict an angled, bendable, or articulating cannula 780 with a telescoping secondary cannula 782 inserted in the sublingual location which would result in a substantially straight implant placed with the anterior anchor portion of the implant located adjacent to a superior part of the mandible.

FIG. 33 depicts a straight cannula 760 inserted in the submandibular location which would result in a substantially straight implant placement with the anterior anchor located adjacent to an inferior part of the mandible. In another example, FIG. 34 shows a curved cannula inserted from a submandibular location which results in a slightly curved placement with the anterior anchor located adjacent to a mid-level position on the mandible.

In another embodiment, the second sleeve may have memory shape (e.g. NiTi) or may be a plastic sleeve.

The disclosed implants as described above are substantially flexible, and are typically fabricated of flexible and/or elastic materials such as silicone, urethane, fluoroelastomer, or other bio-compatible elastomers, polyethylene terephthalate (e.g. Dacron®) or other fibers, bioabsorbable polymers, flexible metals or the like. The flexibility of the implants allows for such implants to be easily deployed and implanted through small cross-section cannulas, which may be straight, curved or articulated, without the implant body jamming within the cannula bore. Longer implants may be delivered through curved or bent cannulas than would be possible with stiff or rigid implant materials or designs.

Because such implants are substantially flexible, pulling the implants, instead of pushing them, through the cannulas may be advantageous for certain applications, such as narrow, straight, curved, deformable or articulated cannulas. The primary advantage of pulling or deploying a flexible implant from such a curved or straight cannula is an increased resistance to bunching, buckling, or otherwise jamming in the cannula bore. This aspect of the deployment method allows such flexible implants to be delivered around tight bends in the cannula, thus enabling implantation in difficult to reach locations such as delivery within the tongue through the sublingual space (see FIGS. 31-32B). Pulling also allows longer implants to be delivered than would otherwise be the case. In another embodiment, only the end portions of the implant are deformable.

Figure 35A:
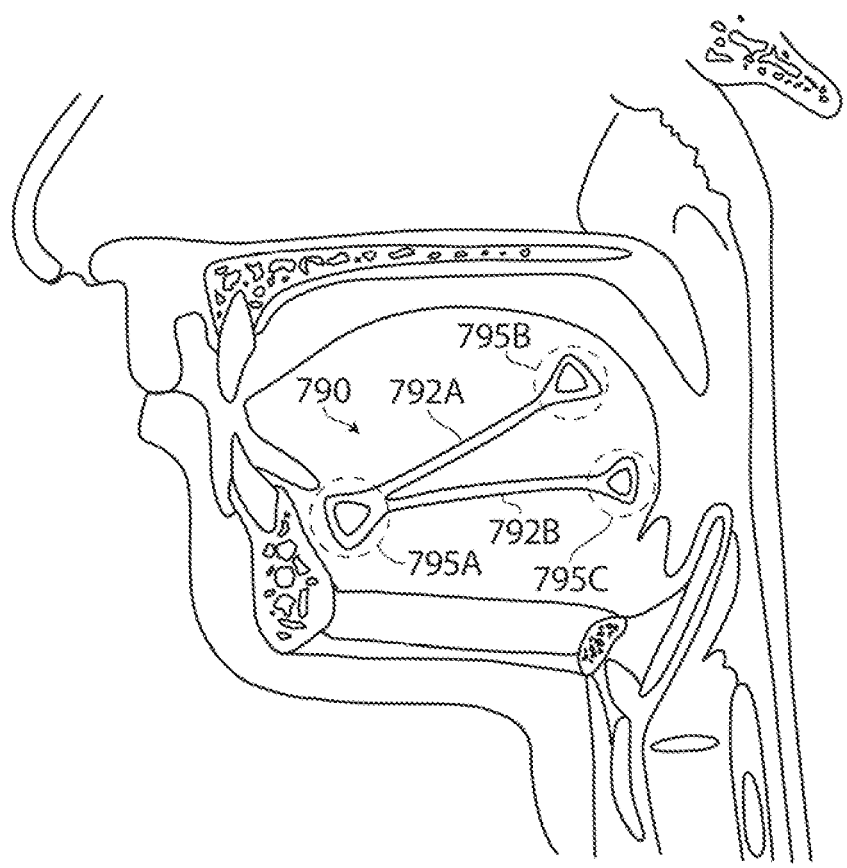
FIG. 35A depicts another OSA implant that comprises a unitary V-shaped implant body with first and second legs and anchoring ends implanted in a patient's tongue for applying linear-directed forces in different distinct vectors.

FIG. 35A schematically illustrates another embodiment of implant 790 that comprises a unitary implant body with first and second elastic elements ("legs") 792A and 792B that can be deployed in different orientations in different patients' tongues. It can be understood that implant 790 of FIG. 35A can be implanted by means of a primary cannula carrying two resilient curved stylettes (or secondary slotted cannulas, not shown) that are deployed from the primary cannula. The implant 790 again provides three anchor points 795*a*-795*c* as shown in FIG. 35. As described above, the V-shaped implant 790 can have any suitable angle between the legs 792A and 792B and any suitable forces can be applied by each leg of the V-shaped implant.

Figure 35B:
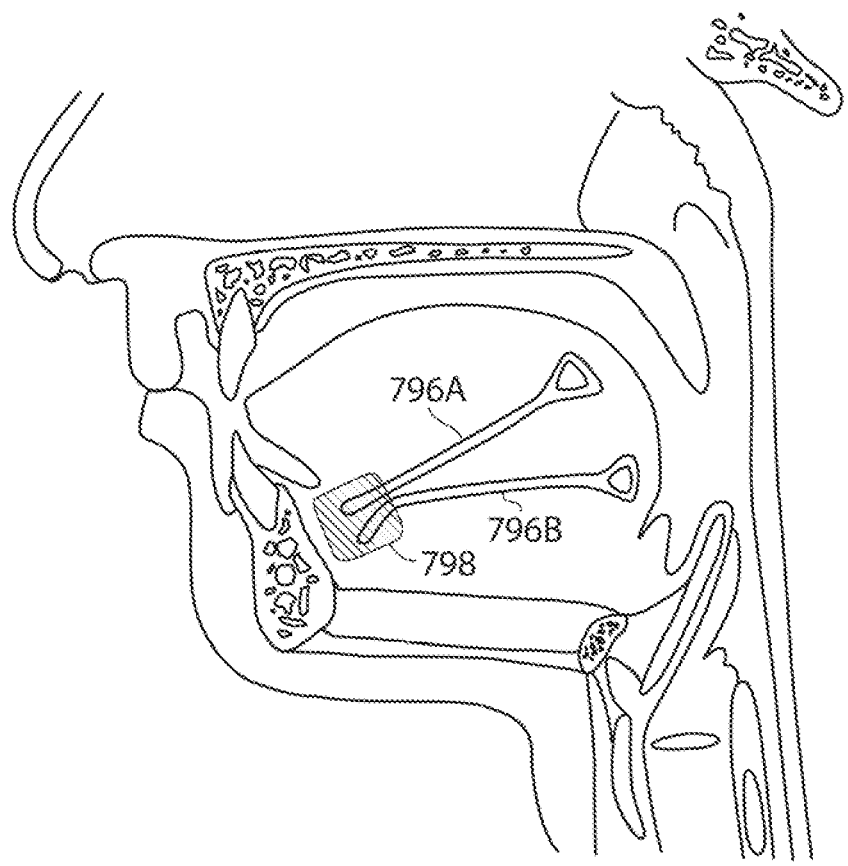
FIG. 35B depicts first and second OSA implants that utilize a fibrotic response to effectively create in-situ a V-type implant with first and second legs for applying linear-directed forces in different vectors.

FIG. 35B depicts first and second OSA implants 796A and 796B that are introduced with at least a portion of the implants in close proximity. Thereafter, a fibrotic response indicated at 798 may be induced that can effectively couple the ends of the implants to again provide a V-type implant wherein the first and second implants apply linear-directed forces in different vectors.

Figure 36:
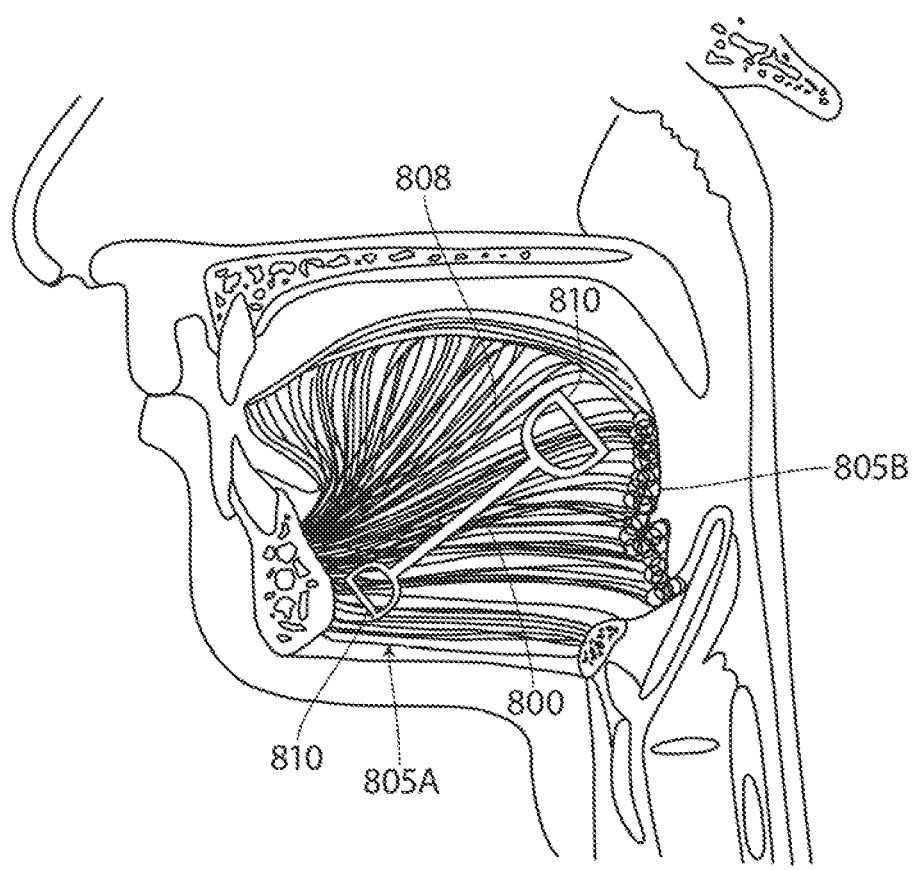
FIG. 36 depicts another OSA implant that is configured with an element of an anchoring end portion configured for extending transverse to the axis of contractile muscle fibers.

Exemplary implants of the disclosure can be configured with anchor portions at various locations along the implants, including the ends, or distributed along the length of the elastic or spring elements of the implant, or adjacent to the elastic or spring elements and serve to attach the implants to tissue. The tissue can comprise soft and hard tissues and structures, including skin, mucosa, muscle, fascia, tendon, ligament, cartilage, or bone so as to allow the elastic or spring elements to apply forces and/or displacements to said soft tissue, hard tissues or structures. When employed within a patient's tongue, the anchor portions of such implants can form attachments directly within tongue muscles, including the geniohyoid, the genioglossus, the vertical, the transverse, and the longitudinal muscles. The geniohyoid, the genioglossus, and the vertical muscles within the tongue substantially run in a direction from their attachments at the central anterior portion of the mandible and fan outward isentropically toward the posterior and superior oral cavity where the transverse and longitudinal muscles reside (FIG. 36). As described above, the anchor portion of the implant can attach by means of tissue plugs through holes in the anchor portions, ingrowth of muscle tissue into channels, passages, pores, or other interstitial spaces in the anchor portion of the implant body.

The implants of the disclosure may be implanted in such a manner and in specific orientations so as to encourage the isentropic muscle tissue to in-grow and attach to said anchors to encourage specific characteristics. These characteristics may include, but are not limited to, accelerated or delayed attachment to said muscle tissues, stronger or weaker attachments, isentropically strengthened attachments, reduced or increased stiffness of the attachments, reduced pain and/or reduced sensitivity of the attachments.

In another aspect of the invention, an implant 800 (FIG. 36) has end portions or anchoring portions 805A and 805B that are configured with elements, surfaces and surface areas that allow for tissue plugs or tissue growth therein that resist unwanted movement of the implant end within tissue planes, such as along the surface of muscle fibers 808. FIG. 36 depicts the orientation of muscle fibers 808 in a patient's tongue. More in particular, referring to FIG. 36, the implant 800 has end portions 805A and 805B each with an element 810 that is configured to extend transverse to a selected dimension of such muscle fibers 808. The length of the feature or element 810 that extends transverse to muscle fibers can be at least 2 mm, 4 mm, 6 mm or 8 mm to thereby provide assurance that the implant will not migrate in an intra-muscle fiber tissue plane.

In another aspect of the invention one or more of the anchoring portion can be a composite structure (e.g. a polyester fiber reinforced silicone rubber or a substantially non-elastic polymer or metal). The composite structure may limit loss of applied force that might otherwise occur due to stretching of the anchoring portion.

In another aspect of a method of the invention, referring to FIG. 36, the implant body 800 is positioned in a targeted site, such as a patient's tongue, such that the forces applied by the elastic portion of the implant are substantially aligned with the direction of contraction (or axis) of contractile muscle fibers 808 and wherein the anchoring portions of the implant body 800 include tissue engaging elements that extend substantially transverse to the axis of such contractile muscle fibers 808.

Figure 37:
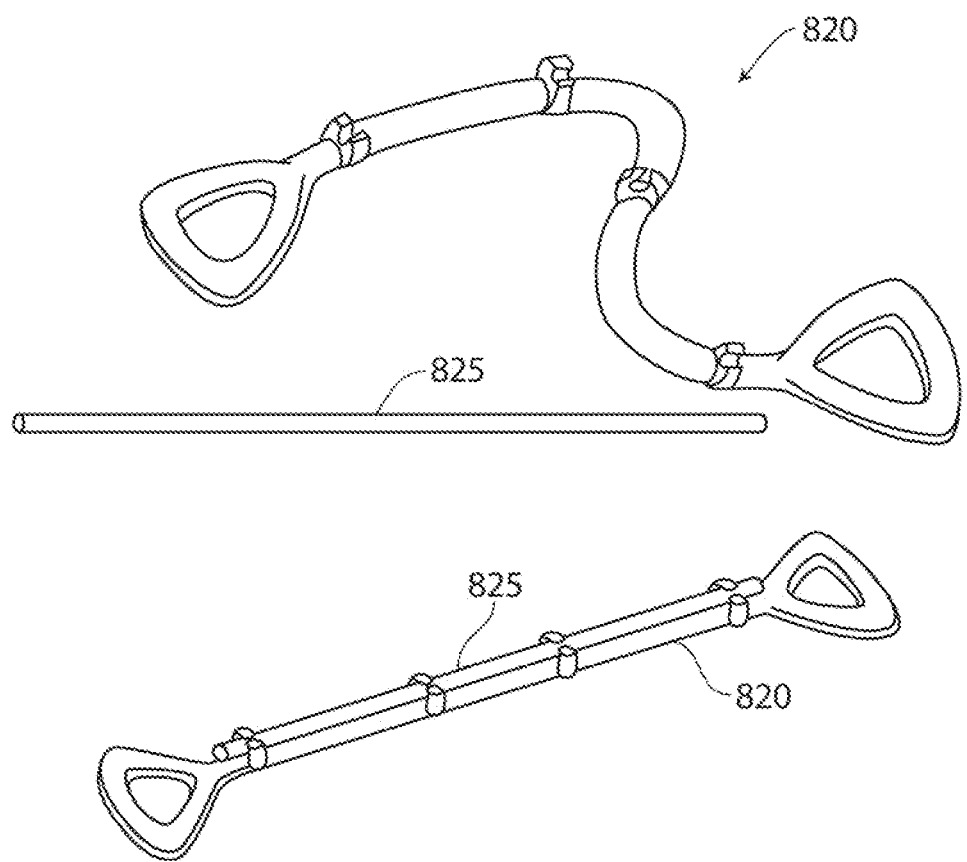
FIG. 37 illustrates another OSA implant that includes an elongated elastic portion and cooperating elongated bioerodible portion for temporarily maintaining the implant in an extended, stressed position.

FIG. 37 illustrates another embodiment of flexible implant 820 which can be temporarily maintained in an elongated position. In this embodiment, the implant 820 carries a semi-rigid rod 825 of a bioabsorbable material (e.g. a bioabsorbable polymer) embedded or locked into features on a surface of the implant body. The implant thus can be configured with sufficient buckling strength so that the implant 820 and bioabsorbable rod 825 can be pushed through a cannula that may be straight, bent, curved, or articulated, without jamming or bunching. This embodiment provides an alternative means for implant deployment rather than the stylette deployment of FIG. 31.

E. Implant Force and/or Movement Parameters

Implant Force Threshold. The implants of the disclosure may apply forces and displacements to anatomical structures within the patient's airway, including the tongue and soft palate, to treat obstructive sleep apnea (OSA) by repositioning and/or applying forces to said anatomical structures in such a manner as to provide an open airway during normal breathing. The forces applied by said implants to said anatomical structures are large enough to sufficiently move, or displace, said structure so as to provide a clear airway when the patient is asleep, but are not so large as to damage the surrounding tissue, damage the implant, prevent proper airway function, or prevent proper tongue function such as in normal speech and swallowing.

When the one or more implants of the disclosure are employed within the patient's tongue to prevent airway occlusion associated with OSA when said patient is asleep and fully relaxed, said implant(s) provide sufficient force to allow the airway to open during normal breathing. The force necessary to open said airway during normal breathing may be a force less than the weight of the tongue itself, as normal breathing provides an internal pressure that acts to help open the airway. The minimum force supplied by said implant(s) to allow the airway to open during normal breathing is referred to as the minimum threshold force for therapeutic benefit. This minimum threshold force for one or more implants within or adjacent to the tongue is about 0.5 Newtons in some embodiments, the minimum threshold force is about 1.5 Newtons in other embodiments, and the minimum threshold force is about 3.5 Newtons in still other embodiments.

When one or more implants of the disclosure are employed within the patient's soft palate to prevent airway occlusion associated with OSA when said patient is asleep and fully relaxed, said implant(s) provide sufficient force to deflect the soft palate away from the back wall of said patient's throat thus providing an open airway. As with the tongue, the force necessary to open said airway during normal breathing may be a force less than the weight of the soft palate itself, as normal breathing provides an internal pressure that acts to help open the airway. The minimum force supplied by said implant(s) to allow the airway to open during normal breathing is referred to as the minimum threshold force for therapeutic benefit. This minimum threshold force for one or a more implants within or adjacent to the soft palate is about 0.2 Newtons in some embodiments, the minimum threshold force is about 0.5 Newtons in other embodiments, and the minimum threshold force is about 1.0 Newtons in still other embodiments.

Implant Motion Threshold. The implants of the disclosure apply forces and displacements to anatomical structures within the patient's airway, including the tongue and soft palate, to prevent obstructive sleep apnea (OSA) by repositioning said anatomical structures. The displacements applied by said implants to said anatomical structures are large enough to sufficiently move, or displace, said structures so as to provide a clear airway when the patient is asleep, but are not so large as to cause adverse side effects. Said side effects may include limited tongue or soft palate function resulting in adverse effects on speech and/or swallowing, difficulty breathing, unwanted remodeling of tissues over time, damage to soft or hard tissues, and causing said soft structures, like the tongue or soft palate, to interfere with other anatomical structures or to cause other unwanted effects.

When implanted within the tongue, the implants of the disclosure provide forces and displacements to the tongue to allow the patient's airway to remain open during normal breathing when the patient is asleep and fully relaxed. The maximum displacement of the tongue that does not result in undesired side effects, as mentioned above, is referred to as the maximum threshold displacement for therapeutic benefit. This maximum threshold displacement for one or more implants within or adjacent to the tongue is between about 0.5 mm and about 20 mm in some embodiments, between about 1.0 mm and about 15 mm in other embodiments, and between about 1.0 mm and about 10.0 mm in still other embodiments.

When implanted within the soft palate, the implants of the disclosure can provide forces and displacements to the soft palate to allow the patient's airway to remain open during normal breathing when the patient is asleep and fully relaxed. The maximum displacement of the soft palate that does not result in undesired side effects, as mentioned above, is referred to as the maximum threshold displacement for therapeutic benefit. This maximum threshold displacement for one or more implants within or adjacent to the soft palate is from 0.5 mm to 5.0 mm in some embodiments.

When implanted in the tongue, the implants of the disclosure may provide an effective therapeutic window of operation bounded by a minimum threshold force required to prevent the tongue from obstructing the airway during normal breathing when the patient is asleep and relaxed, and by a maximum displacement threshold above which the implant(s) adversely affects normal airway and tongue function including speech, swallowing, breathing, etc. This effective therapeutic window is identified based on the forces and displacements described above.

When implanted in the soft palate, the implants of the disclosure may provide an effective therapeutic window of operation bounded by a minimum threshold of force required to prevent the soft palate from obstructing the airway when the patient is asleep and relaxed, and by a maximum displacement threshold above which the implant(s) adversely affects normal airway or mouth function including speech, swallowing, breathing, etc. This effective therapeutic window is identified based on the forces and displacements described above.

Implant Force/Motion Directions within the Tongue. When the one or more implants of the disclosure are employed within the patient's tongue to prevent airway occlusion when said patient is asleep and fully relaxed, said implant(s) provide sufficient force to open the airway during normal breathing. One or more implants may be employed to apply the desired forces and deflections to the patient's tongue. Said implants may be employed in one or more locations within or adjacent to the tongue, they may be anchored in one or more locations within or adjacent to the tongue, and they may apply forces and/or deflections in one or more directions and between two or more locations within or adjacent to the tongue.

Said implants may be employed in such a manner as to relieve obstructions in the airway caused by the tongue resulting in OSA. Generally, this includes displacing the posterior region of the tongue and/or providing forces on the posterior region of the tongue that pull said posterior region in the anterior direction, away from the posterior pharynx wall, resulting in preventing the opening of the airway from closing such that normal breathing can be maintained. Said forces and/or displacements may act to affect the entire posterior region of the tongue, a very specific location in the posterior region of the tongue, a linear area of affect in the posterior region of the tongue (i.e., a linear area that runs cranially and caudally so as to create a channel through which the airway remains patent), or any combination of the above.

In one exemplary embodiment, a single implant is employed to apply a force to the posterior region of the tongue in an approximately horizontal anterior direction as viewed in a patient standing straight up with their head facing forward (FIG. 24). In another exemplary embodiment, a single implant is employed to apply a force to the posterior region of the tongue at an inclined angle to the horizontal, and in the anterior direction as viewed in a patient standing straight up with their head facing forward (FIG. 25).

Figure 26:
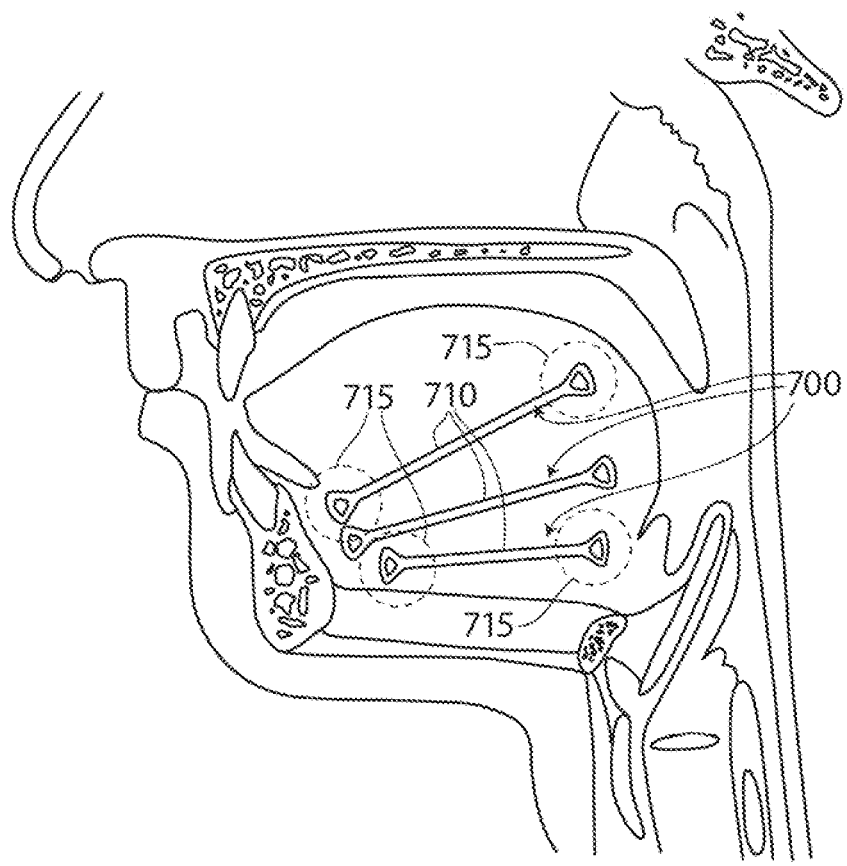
FIGS. 26-27B depict a plurality of OSA implants each with first and second anchoring ends implanted in a patient's tongue for applying linear-directed forces in different distinct vectors.
Figure 27A:
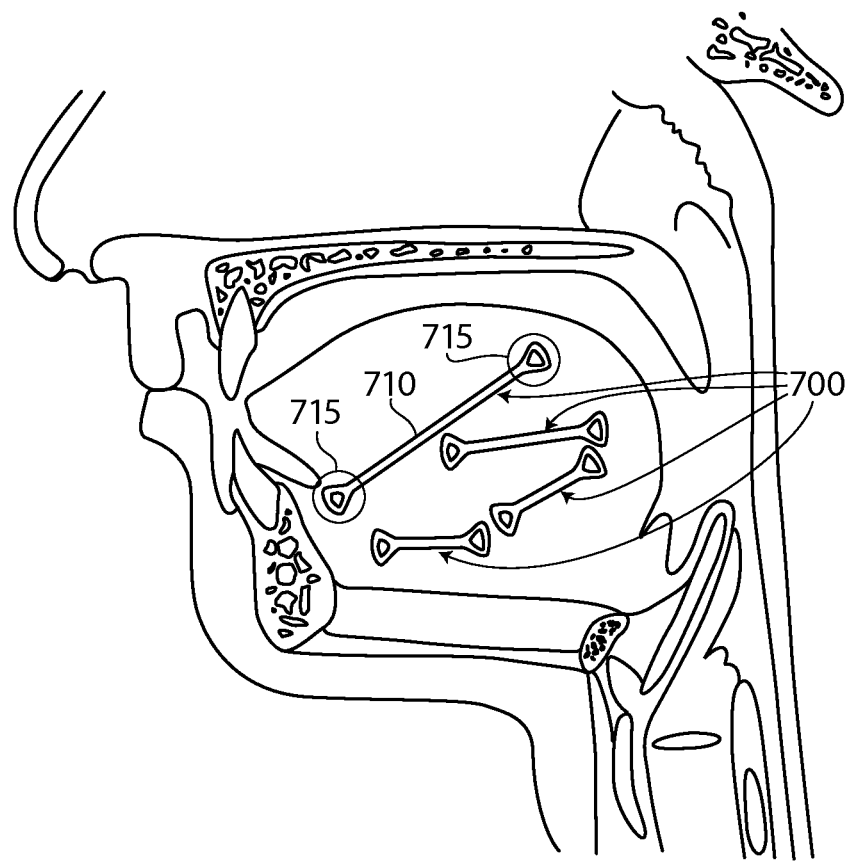
Figure 27B:
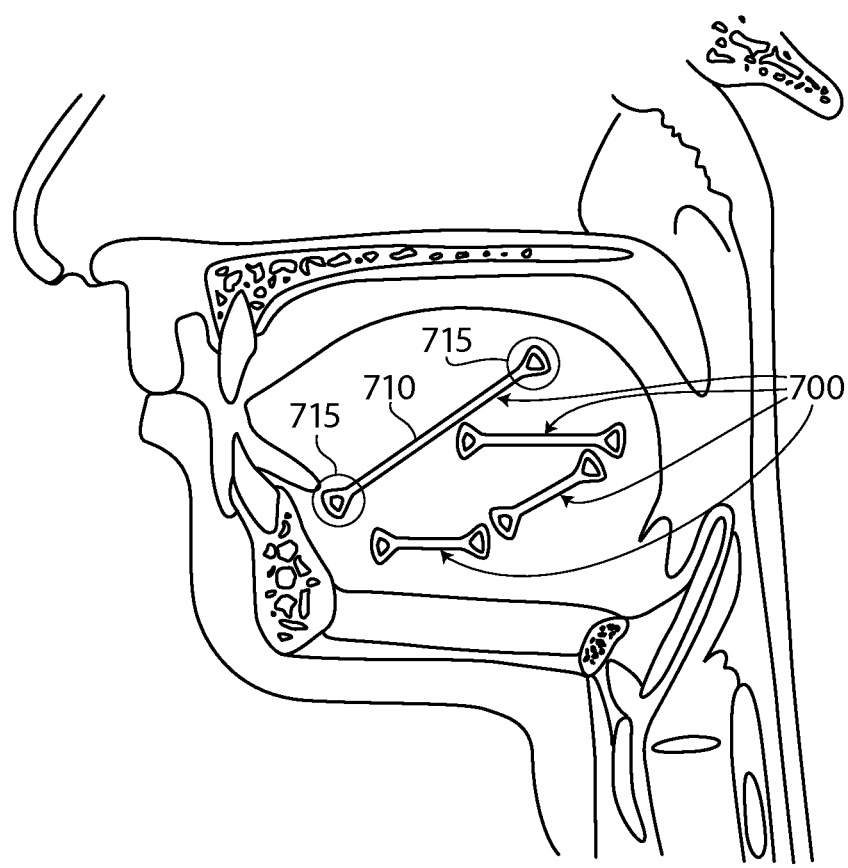

In another embodiment of the invention, three implants are employed within the tongue to apply forces to the posterior region of the tongue in such a manner as to advantageously create a longitudinal open region between said tongue and the posterior pharyngeal wall, running in the direction of air motion during normal breathing. The three implants in this embodiment are acting in different directions to create the desired net distribution of forces and displacements on the tongue (FIG. 26). In another embodiment of the invention, four implants are employed within the tongue to apply forces distributed throughout the tongue, with the implants acting in different directions to create the desired net distribution of forces and displacements on the tongue (FIG. 27).

When more than one implant is used, the set of implants may all lie in any orientation with regard to each other and the surrounding anatomical structures, including in a linear arrangement, a parallel arrangement, a planar array (including but not limited to a triangulated structure), a three-dimensional array, or any combination of these arrangements. The implants may be joined together in any multi-linear, non-linear, or multiply-linearly segmented manner. One example is described above in FIGS. 28A-28C, wherein two linear elastic or spring elements 720A and 720B are connected to provide a common anchor point 725a in tissue at one end of each of the two said linear elements, respectively. The other ends of the first and second linear elements provide additional anchor points 725b and 725c in the tissue. In this manner, anchor points 725b and 725c are pulled in the direction of the common anchor 725a so as to provide a bi-linear implant structure. By extension, and in this manner, complex multi-linear structures or networks of linear elements may be constructed to achieve the desired clinical effects. Similarly, two or more implants comprising multi-linear components may be employed in conjunction to achieve the desired clinical effects. Alternately, the elastic or spring elements may be fabricated in such a fashion as to produce a joined, jointed, or linked structure during the manufacturing process.

Implant Force/Motion Directions within the Soft Palate. When the one or more implants of the disclosure are employed within the patient's soft palate to prevent airway occlusion when said patient is asleep and fully relaxed, said implant(s) provide sufficient force to open the airway during normal breathing. One or more implants may be employed to apply the desired forces and deflections to the patient's soft palate. Said implants may be employed in one or more locations within or adjacent to the soft palate, they may be anchored in one or more locations within or adjacent to the soft palate, and they may apply forces and/or deflections in one or more directions and between two or more locations within or adjacent to the soft palate.

Said implants may be employed in such a manner as to relieve or prevent obstructions in the airway caused by the soft palate resulting in OSA. Generally, this includes displacing the posterior region of the soft palate and/or providing forces on the posterior region of the soft palate that pull said posterior region in the anterior direction away from the posterior wall of the pharynx resulting in the opening of the airway during normal breathing. More specifically, said implants within said soft palate tend to cause a curvature of the soft palate in the downward and anterior direction to affect said opening of said airway. Said forces and/or displacements may act to affect the entire posterior region of the soft palate, a very specific location in the posterior region of the soft palate, a linear area of affect in the posterior region of the soft palate, or any combination of the above.

In one exemplary embodiment, a single implant is employed to apply a force to the posterior region of the soft palate resulting in a curvature of said soft palate that displaces said soft palate away from the pharynx wall. In another embodiment of the invention, two implants are employed within the soft palate at differing angles and in different locations to apply forces and displacements to the soft palate resulting in a curvature of said soft palate that displaces said soft palate away from the pharynx wall.

Figure 38A:
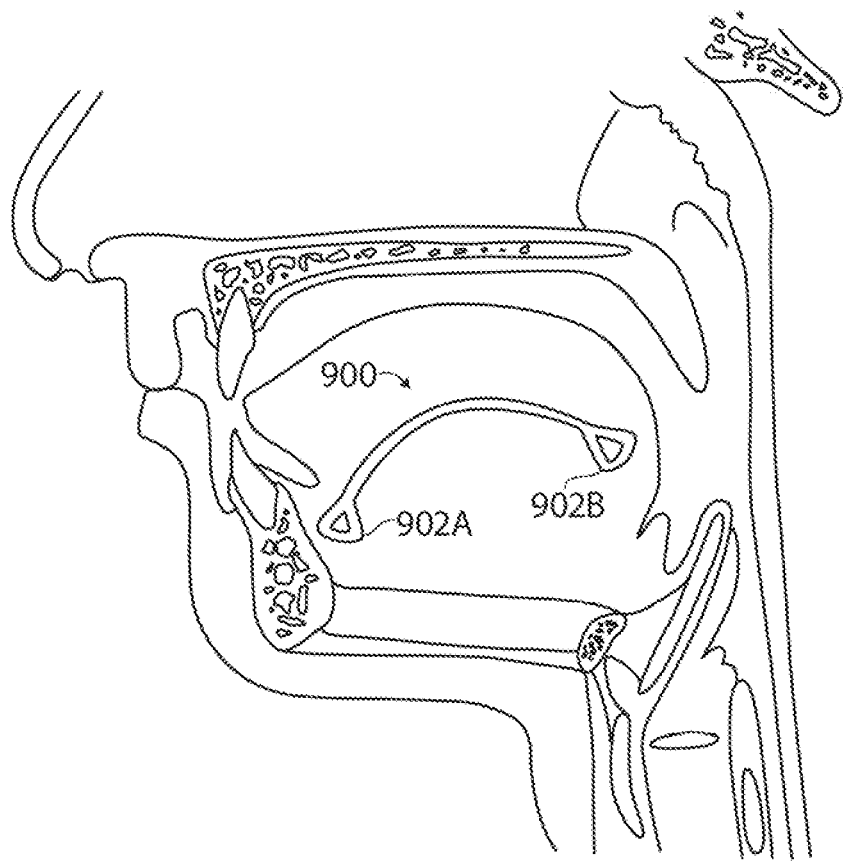
FIG. 38A illustrates an OSA implant that has a curved configuration that can allow the tongue to move by straightening the implant.
Figure 38B:
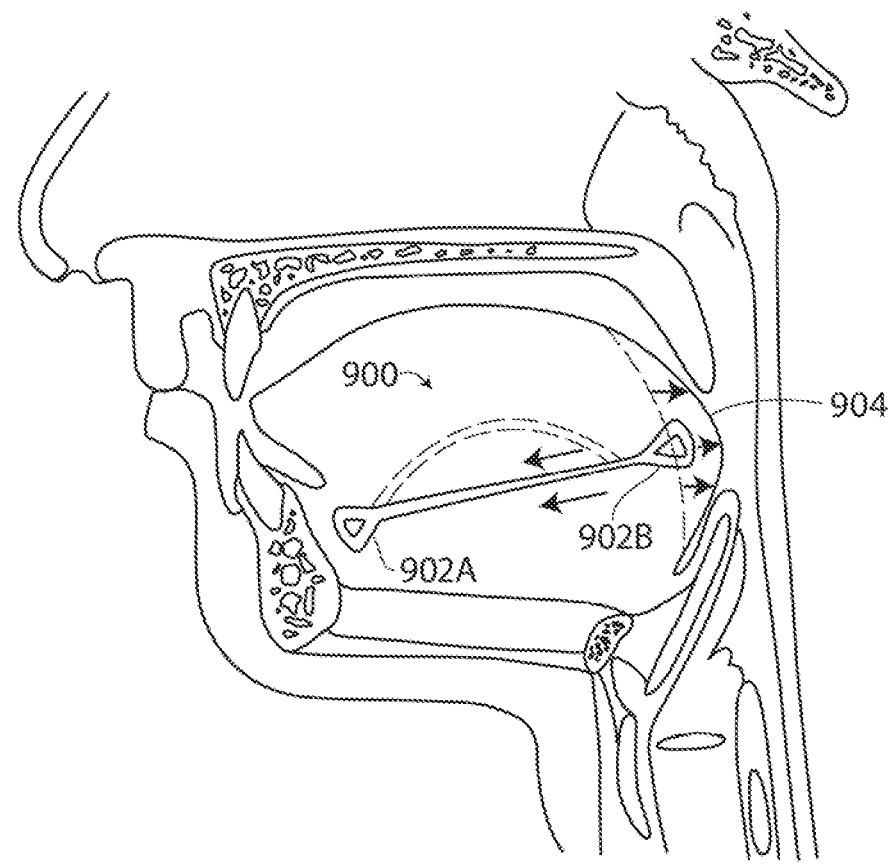
FIG. 38B depicts the curved implant of FIG. 38A in a straightened shape with the tongue displaced posteriorly toward obstructing the airway.

The above-described OSA implants in FIGS. 24-37 generally describe implant bodies and methods that are adapted to apply linearly-directed forces to airway interface tissue. Other embodiments described next relate to implants configured to displace tissue or apply forces in non-linear vectors, which can be used alone or in combination with the linear force-directing implant described previously. In one embodiment, FIGS. 38A-38B depict an elastic OSA implant 900 with anchor ends 902a, 902b that is curved in a repose state and can be implanted in either a curved or linear path, for example, in a vertical orientation in the patient's tongue (FIG. 38A). In FIG. 38B, it can be seen that if tongue base 904 is displaced posteriorly, the implant will be moved toward a straightened configuration wherein the elastic implant will apply forces anteriorly and upward to prevent airway interference. The implant of FIGS. 38A-38B can have any suitable ends for anchoring in tissue, for example, end portions with one or more openings resulting in tissue plugs anchors as described above.

Figure 39:
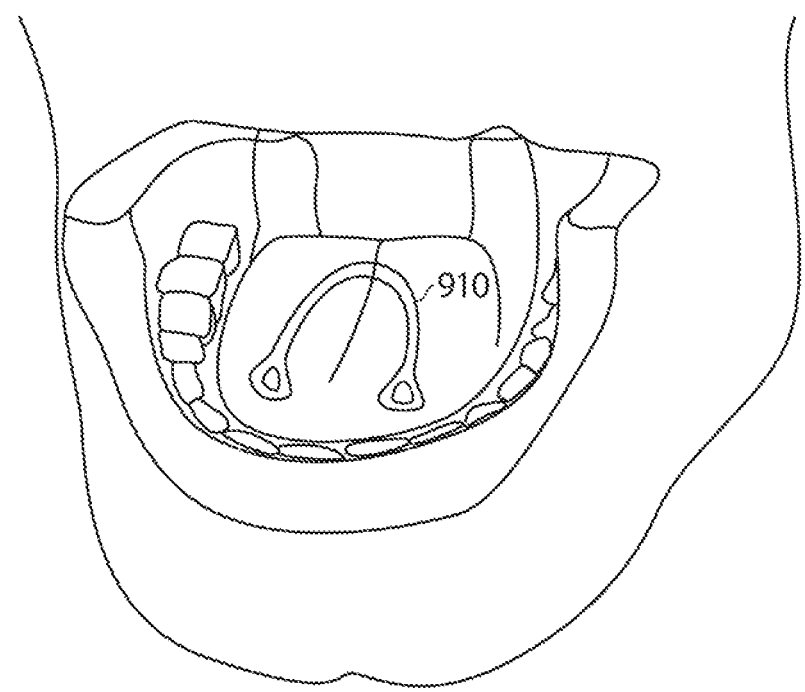
FIG. 39 depicts a curved implant as in FIG. 38A implanted in a horizontal plane in the patient's tongue.

FIG. 39 depicts a curved implant 910 similar to that of FIGS. 38A-38B implanted in a horizontal plane in the patient's tongue. The implant 910 thus partly encircles tissue and applies forces in multiple vectors when stretched to move the tongue forward away from the airway. The implant of FIG. 39 can be implanted using a curved introducer as described previously.

Figure 40A:
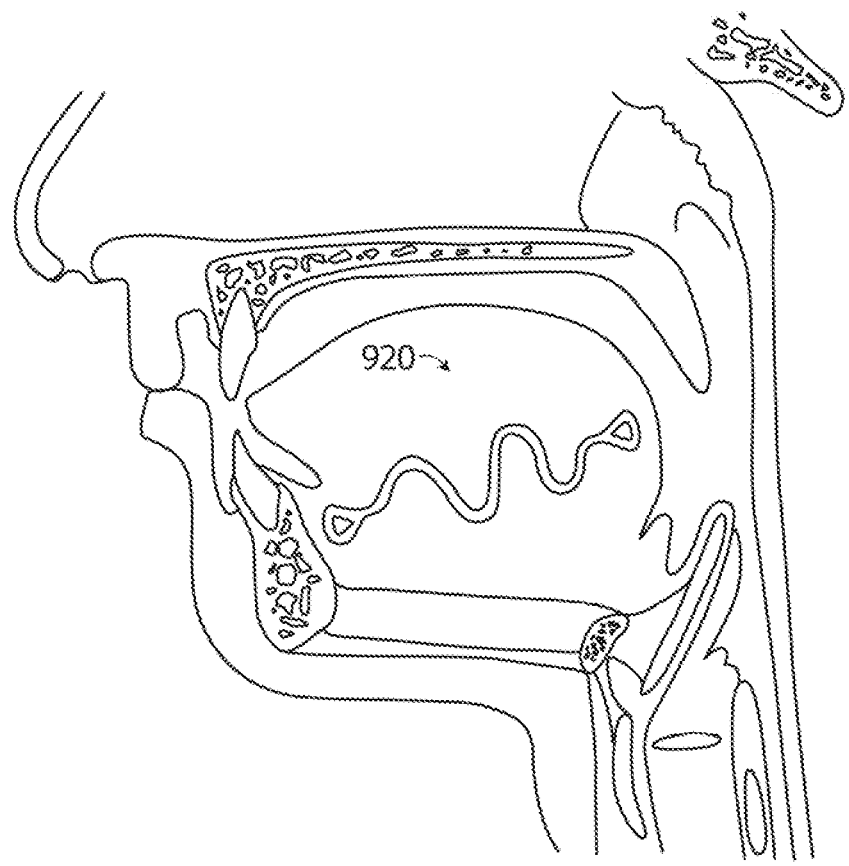
FIG. 40A depicts an S-shaped or serpentine implant in a vertical orientation that may allow the tongue to move by straightening the elastic implant.
Figure 40B:
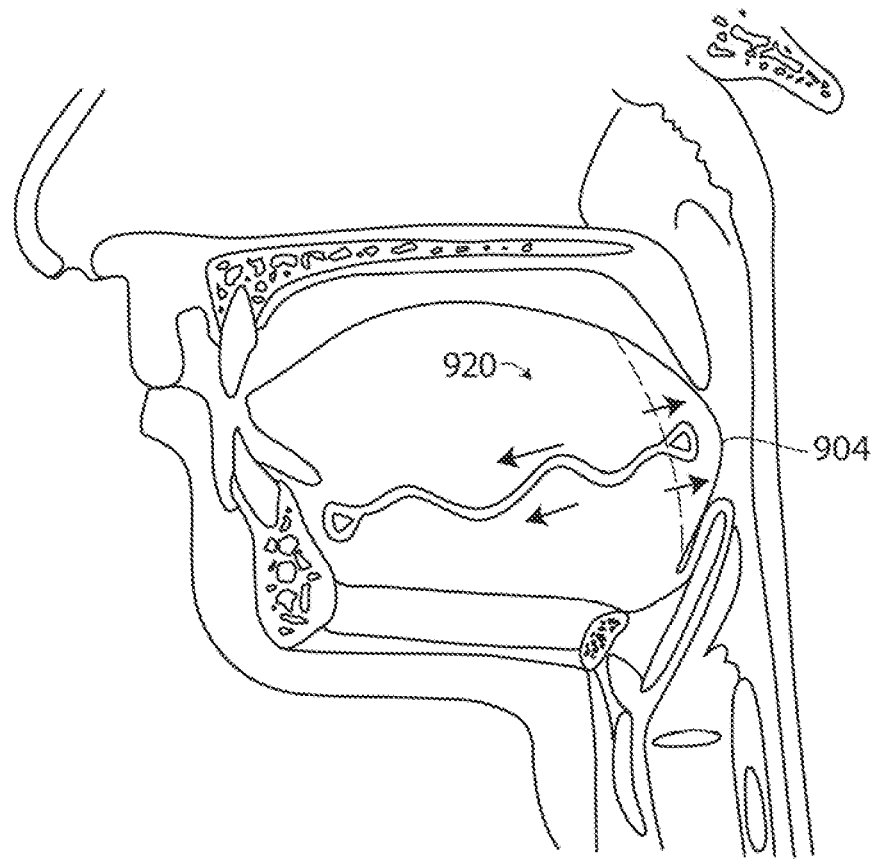
FIG. 40B depicts the serpentine implant of FIG. 40A in a straightened shape with tongue displaced posteriorly.
Figure 41:
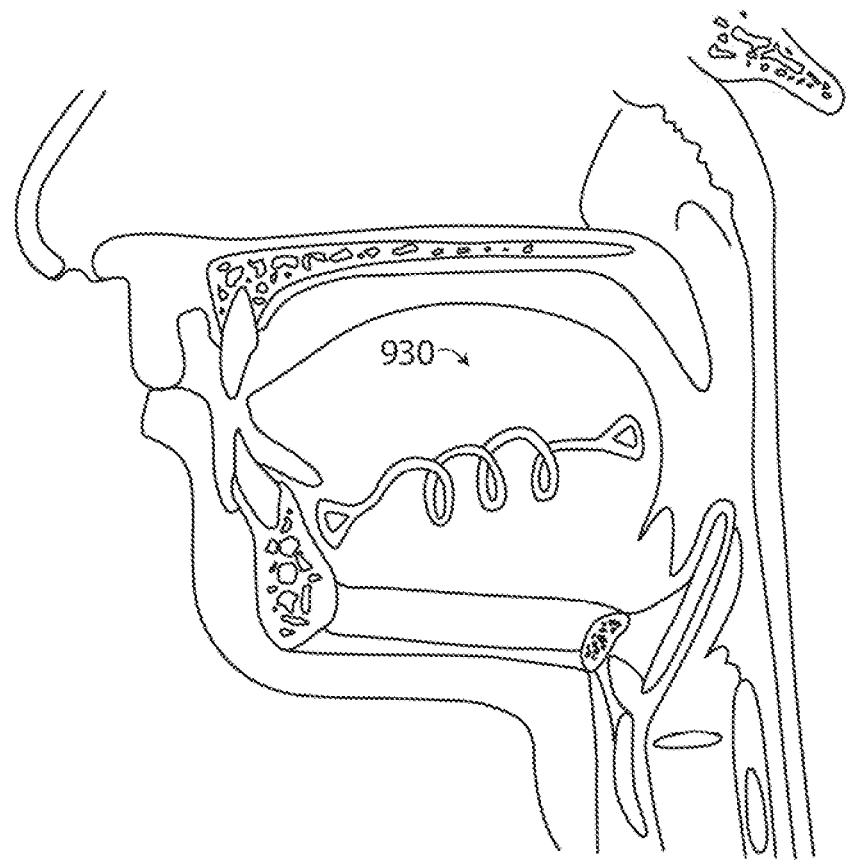
FIG. 41 depicts a helical curved implant that again can allow the tongue to move by straightening the implant.

FIGS. 40A-40B depicts another implant 920 that has a serpentine or S-shape in a repose condition in a patient's tongue. As can be understood from FIG. 40B, if the tongue base 904 is displaced posteriorly, the implant will be stretched and the elastic implant will apply forces anteriorly and toward the serpentine condition to compress tongue tissue to prevent airway interference. FIG. 41 depicts another implant 930 that has a helical shape in its repose condition in a patient's tongue. This implant 930 would function as the serpentine implant of FIGS. 40A-40B to apply compressive and anteriorly directed forces to the patient's tongue.

Figure 42:
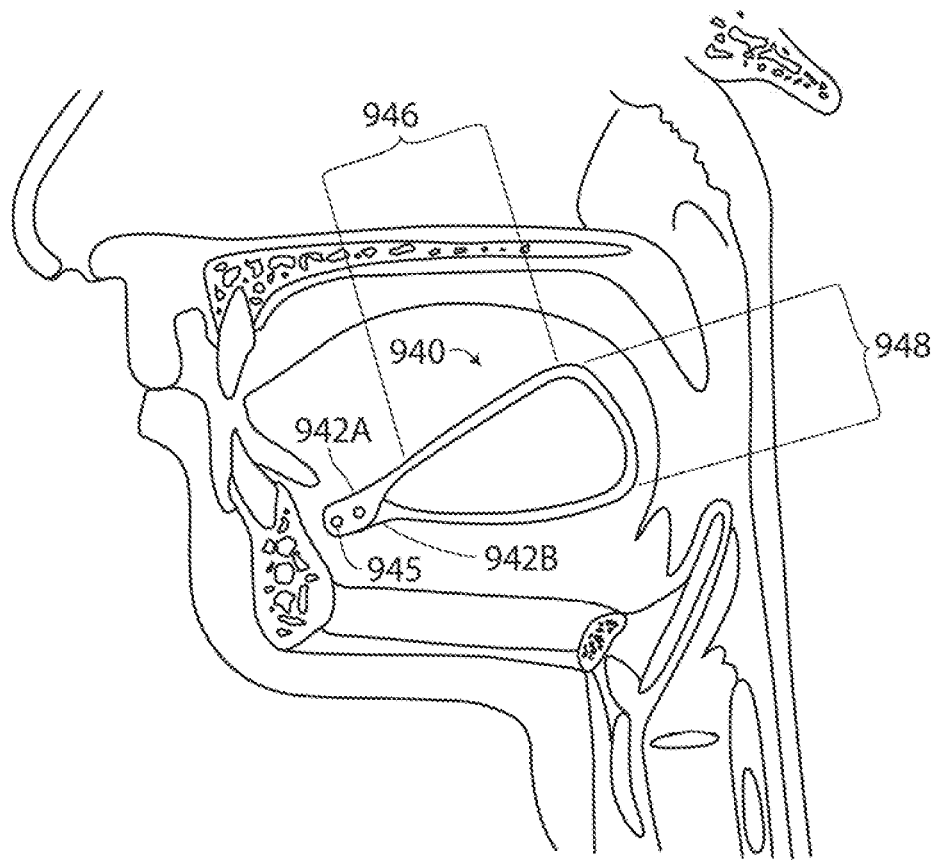
FIG. 42 depicts another type of implant that comprises a loop or encircling OSA implant with a connection means adjacent first and second ends thereof, the implant in a vertical orientation in a patient's tongue.

FIG. 42 depicts another type of OSA implant 940 that comprises a loop or tissue-encircling implant at least partly of an elastic material that encircles tongue tissue or other airway-interface. Such an encircling implant 940 can be implanted using introducer systems described further below, wherein first and second end portions 942a and 942b of the implant are coupled by connection means which can be clips, snap-fit features, pins, ratchets, sutures, stakes, clamps, welds, fusible materials, adhesives and the like indicated at 945. The portion between the ends may have a long curvilinear axis, wherein the medial portion is configured to tensile forces along the axis. Such an encircling implant can apply inwardly-directed, elastic and compressive forces on encircled tissue which may cause tissue to remodel to provide a reduced tissue volume. At the same time, the elastic encircling implant will apply forces in a plurality of vectors to return the implant and engaged tissue that is outside the encircling loop toward the repose shape of the implant and engaged tissue within its path in the targeted site. The implant of FIG. 42 can be configured with the bioerodible elements as described previously to allow the forces to be applied to the tissue slowly over a selected time interval. Still referring to FIG. 42, the encircling implant has anterior portion 946 that extends in first and second legs to the cross-over posterior portion 948, wherein the first (anterior) portion 946 has a first elasticity and the second (posterior) portion has a second elasticity. In one embodiment, the anterior implant portion 946 has greater elasticity than the posterior portion 948, and the posterior portion is adapted to distribute applied forces over a region of the tongue. In another aspect, the posterior region may have more than one elasticity.

Figure 43:
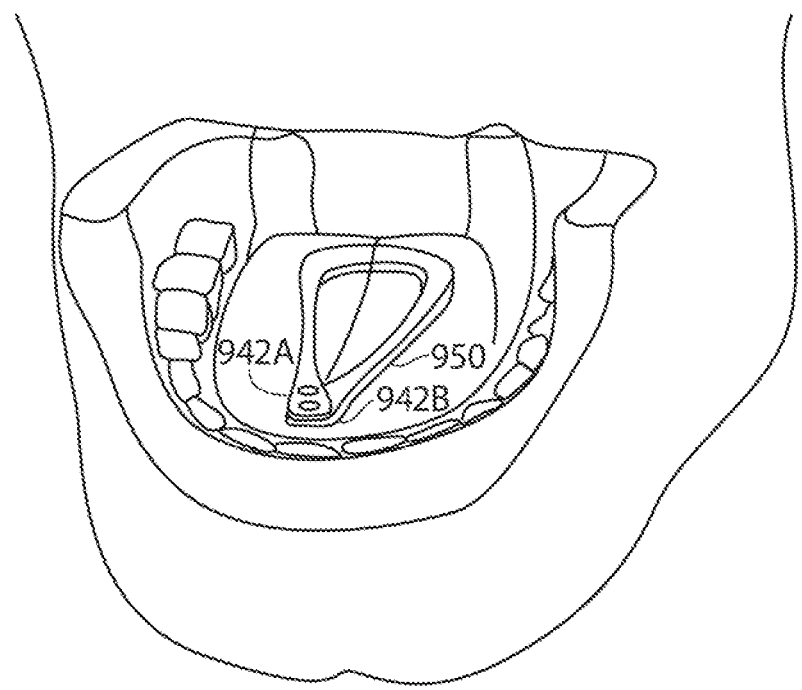
FIG. 43 depicts an encircling implant as in of FIG. 41 in horizontal orientation in a patient's tongue.

FIG. 43 depicts an encircling OSA implant 950 similar to that of FIG. 42 except that the tissue-encircling implant is placed in a horizontal orientation in the patient's tongue. It should be appreciated that a plurality of encircling implants such as those of FIGS. 42 and 43 can be implanted in a patient.

Figure 44A:
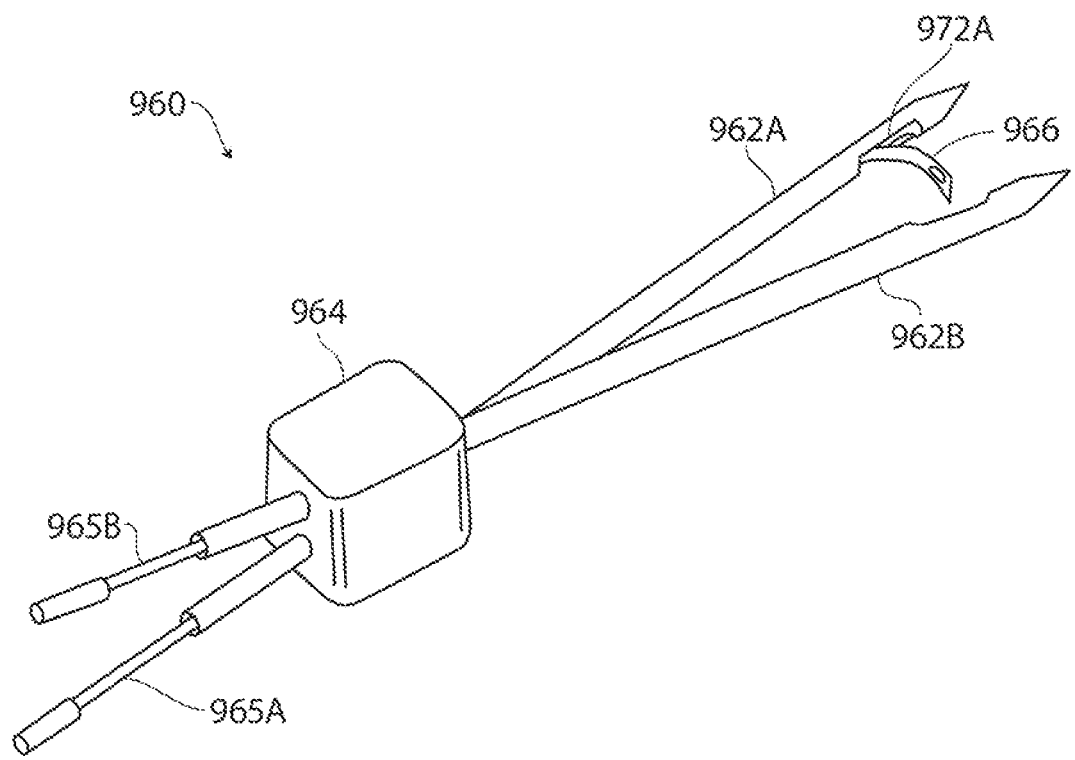
FIG. 44A depicts a device configured for implanting the encircling implant of FIGS. 42-43, with first and second trocar elements and a guide block.
Figure 44B:
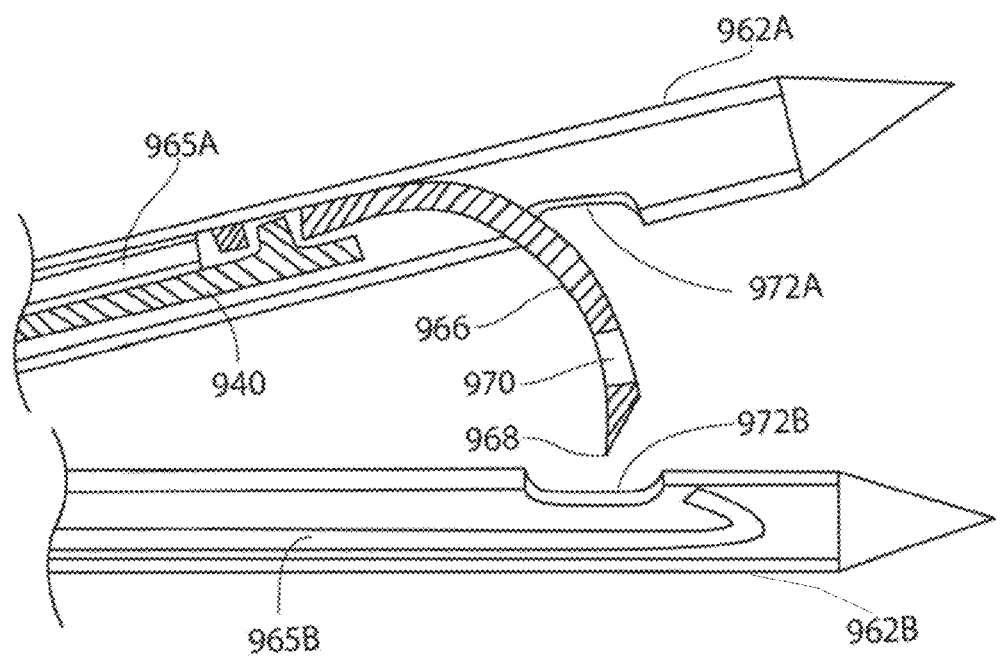
FIGS. 44B-44E depict schematically the steps of using the working end of the device of FIG. 44A to implant and deploy an encircling implant in tissue.

FIG. 44A depicts an introducer system 960 that is adapted for implantation of an encircling-type implant such as the OSA implant of FIG. 42. The introducer system 960 is shown schematically and includes first and second trocar elements, 962A and 962B, a guide block or member 964 which is configured to guide the trocars in a predetermined direction and relative angle when the trocars are extended from the guide block 964 into tissue. Further, the system 960 includes push-pull rods or controlling rods 965A and 965B that are slidably carried in respective bores of the trocar elements, 962A and 962B. In FIGS. 44A and 44B, it can be seen that a releasable, flexible tunneling element 966 that is pre-formed in curve with a sharp tip 968 is releasably coupled to control rod 965A. The distal end of tunneling element 966 is configured with an opening 970 or other grip feature that allows for its coupling to second control rod 965B. The tunneling element 966 has a preformed curvature and can be made of a shape memory alloy (e.g., NiTi) such that when the tunneling element is advanced from the distal port 972A of trocar element 962A, the element tunnels in a curved path to the distal port 972B of the other trocar element 962B.

Figure 44C:
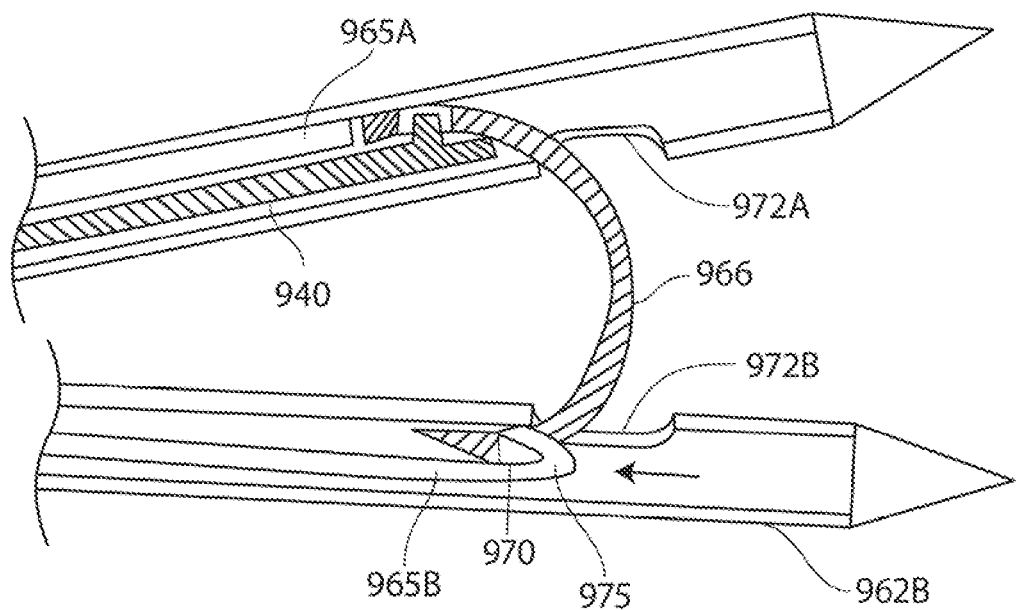

FIG. 44B depicts a cut-away schematic view of the working end of the system of FIG. 44A in a method of use, wherein the distal portions of the trocar elements 962A and 962B are shown as if advanced from the guide block 965 into a targeted tissue site. FIG. 44B shows the tunneling element moved from retracted position (not shown) in a passageway in trocar element 962A to a first extended position outward of port 972A. It can be seen that an encircling implant 940 of the type shown in FIG. 42 is releaseably coupled to tunneling element 966. In some embodiments, coupling is achieved by means of a hook on the tunneling element that holds the implant while the tunneling element and implant advance through tissue. The hook is released upon retraction of the tunneling element. In another embodiment, coupling is achieved by means of a clasp or other means well understood by those of skill in the art. FIG. 44C depicts the next step of the method wherein the curved tunneling element 966 is extended further by advancing rod 965A until the distal end of tunneling element 966 enters port 972B of the opposing trocar element 962B. Thereafter, control rod 965B is moved proximally wherein an engaging hook or other engagement element 975 engages the opening 970 in the tunneling element 966.

Figure 44D:
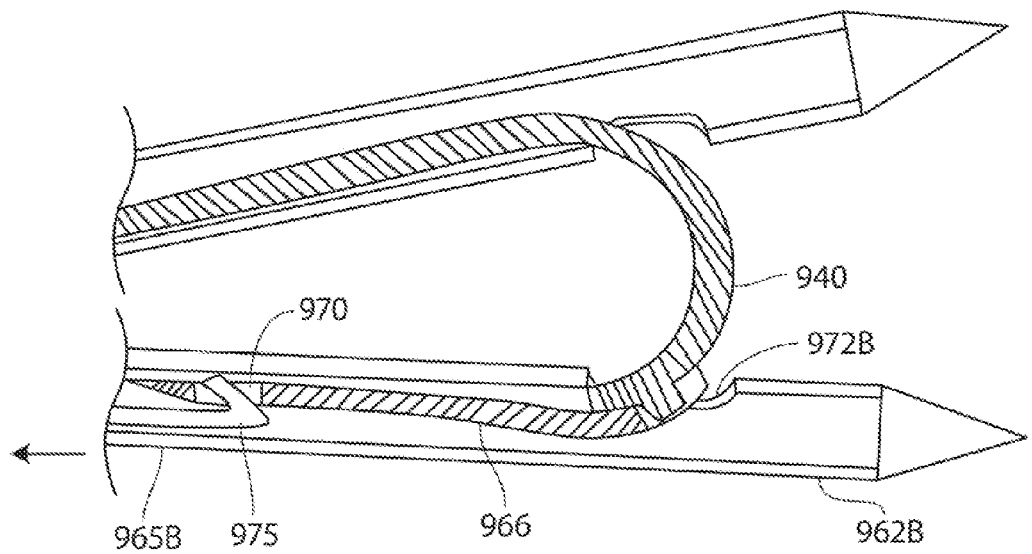
Figure 44E:
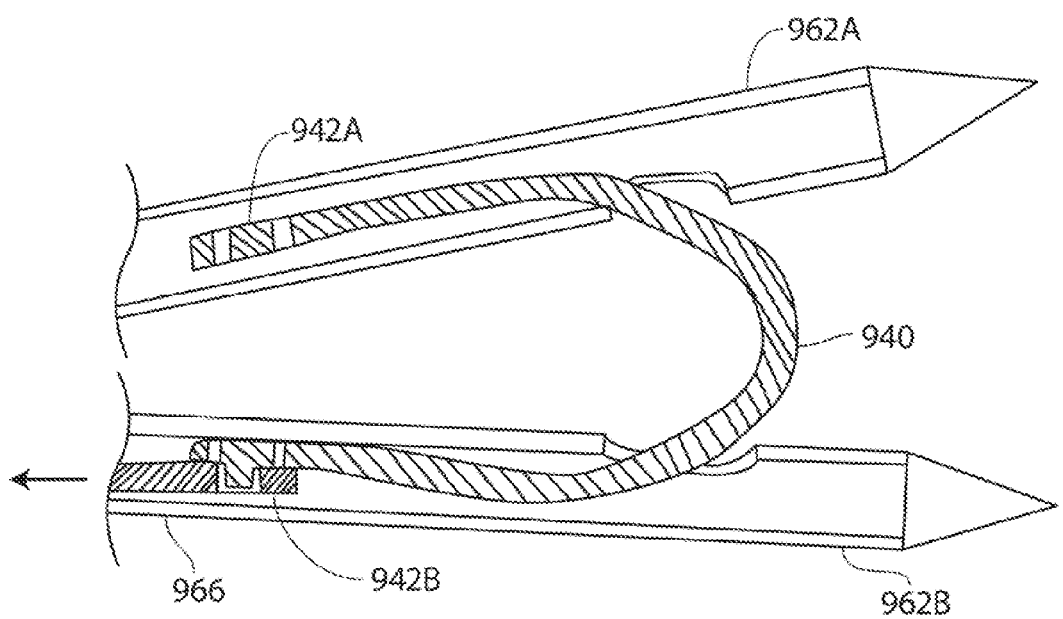

FIG. 44D depicts a subsequent step wherein control rod 965B is moved further in the proximal direction and the OSA implant 940 is pulled through the path in tissue created by the tunneling element 966 and then into port 972B of the trocar element 962B. FIG. 44E depicts another step wherein the implant 940 is disposed with ends 942a and 942b fully bridging between the opposing trocar elements 962A and 962B, such that the physician can prepare to withdraw both trocar elements from the tissue site to thereby release the implant and leave the implant in place in the encircling tissue.

Figure 44F:
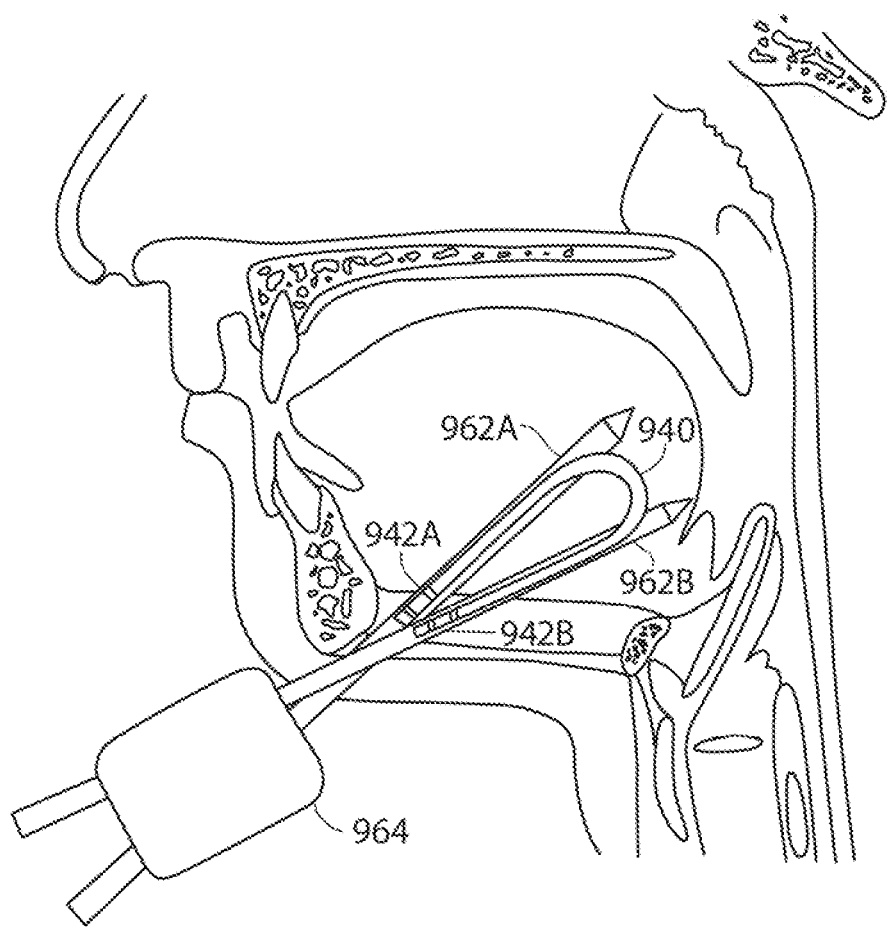
FIGS. 44F-44G depict an encircling implant fully bridged between first and second trocars.
Figure 44G:
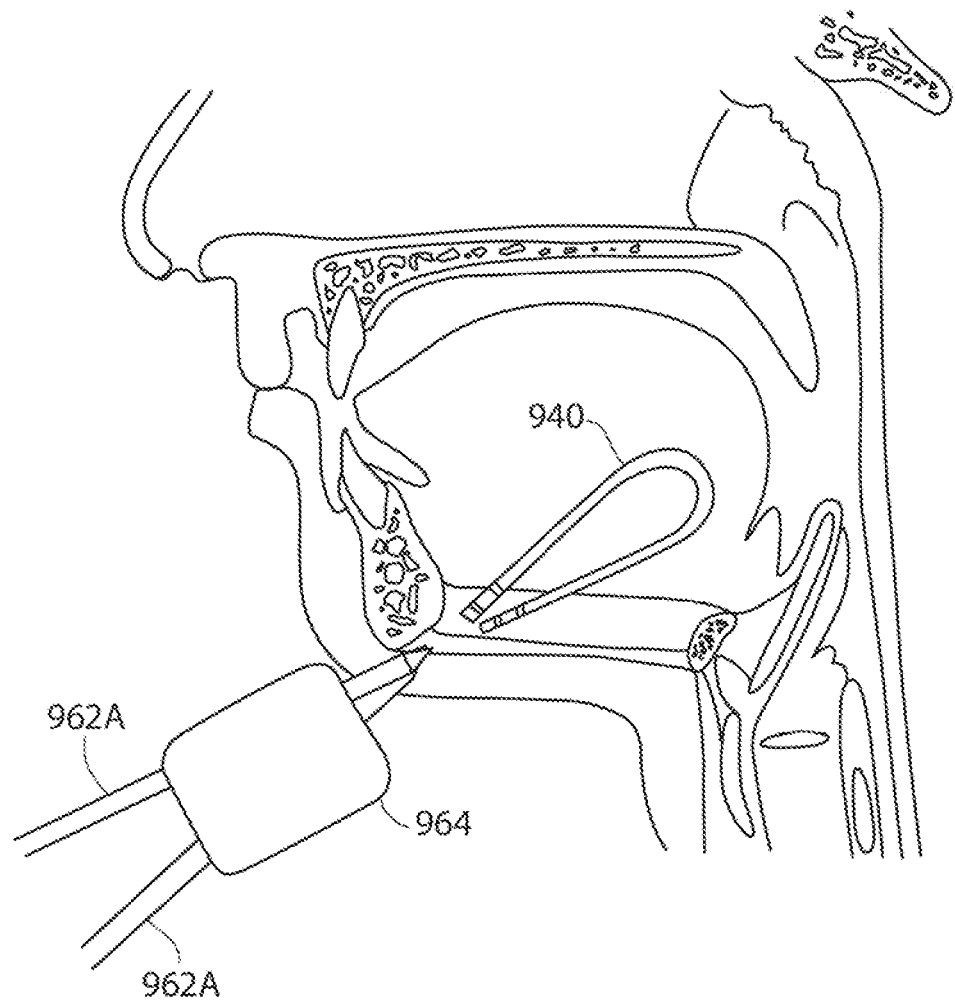
Figure 44H:
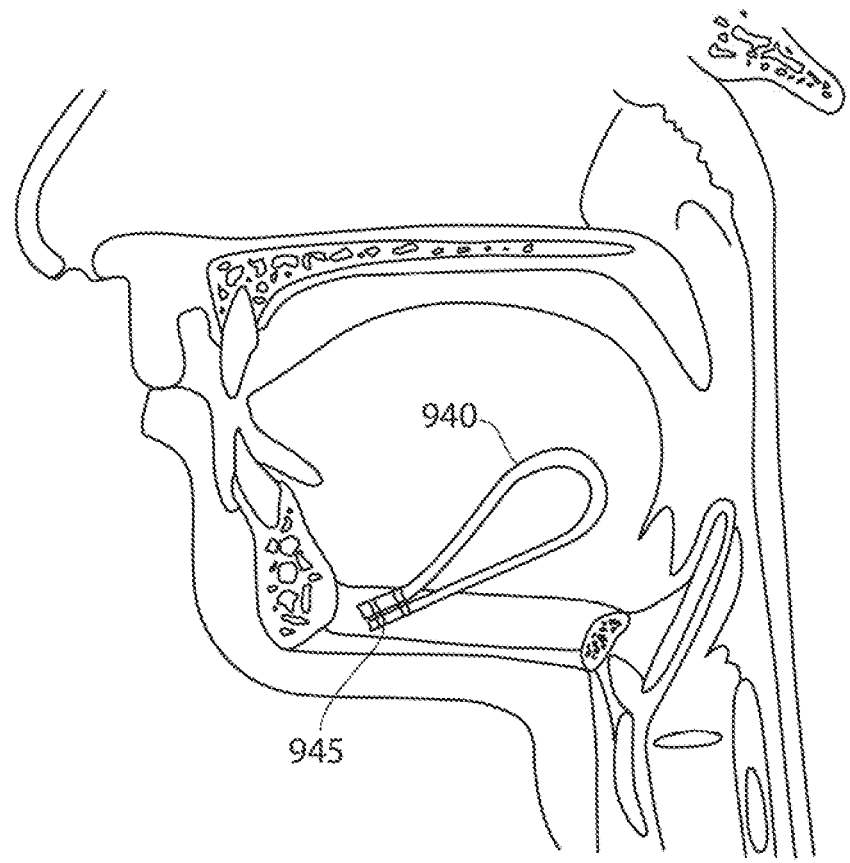
FIG. 44H depicts the final step of the method comprising fixedly connecting the two ends of the implant so as to form a loop or encircling implant.
Figure 45:
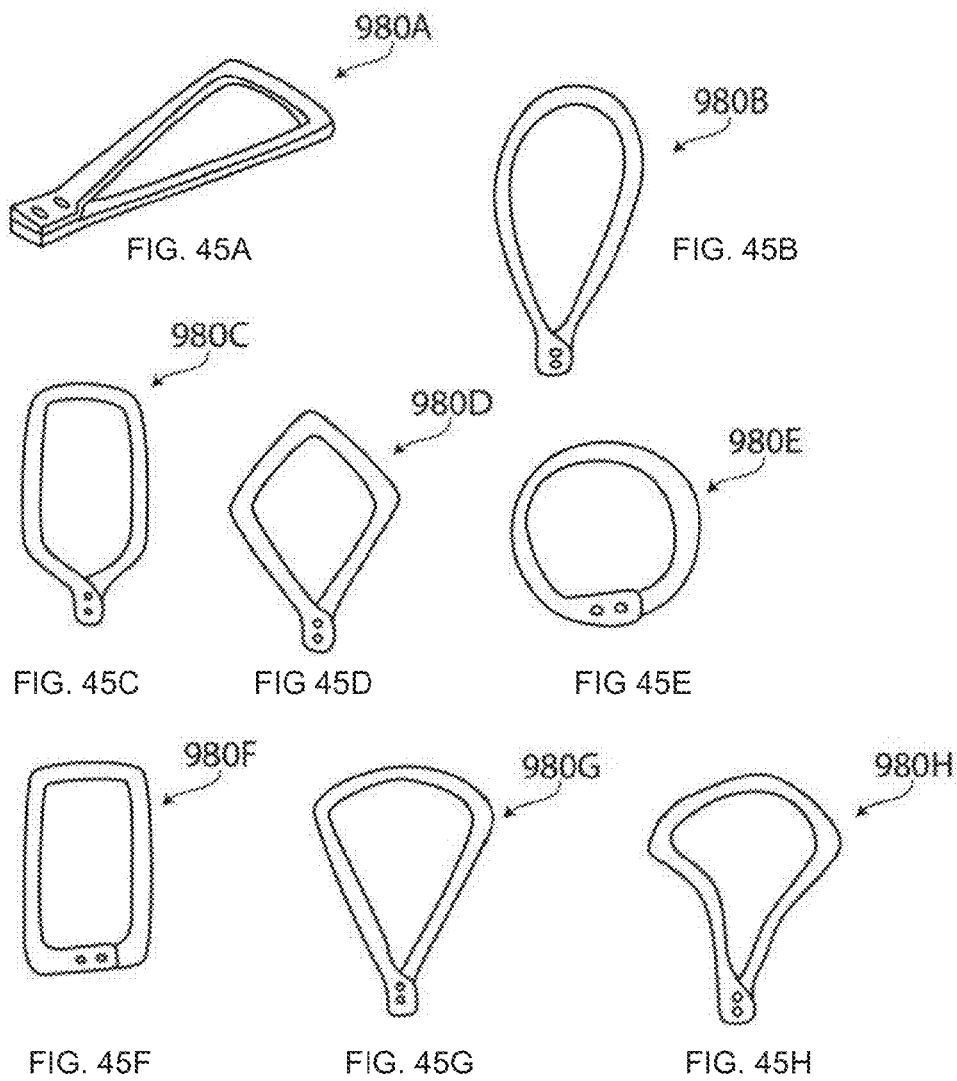
FIG. 45A-H depict various shapes of loop or encircling implants.

Now turning to FIGS. 44F and 44G, the steps relating to FIG. 44E are shown schematically in an optional sub-mandibular access to the patient's tongue. FIG. 44F depicts the implant 940 fully bridged between the trocars 962A and 962B as in FIG. 44E. FIG. 44G shows the trocar elements 962A and 962B withdrawn leaving then implant 940 in place. FIG. 44H then depicts the final step of the method wherein the first and second ends 942a and 942b of the implant 940 are attached to one other by any attachment means 945 as described above of by tissue fibrosis as described above to thereby provide an encircling implant. In one embodiment, implant ends are attached to each another by means of tissue fibrosis. Tissue fibrosis may be induced by having the ends of the implant in sufficiently close proximity to one another such that the fibrotic responses to the implants substantially come in contact with one another. Tissue fibrosis may be induced as a consequence of tunneling (e.g. using trocar or stylet or other means) through the tissue to create a channel through some or all of the gap between the implant ends. The healing response to the channel creates the fibrotic response.

FIG. 45A-H depict various shapes and configurations of loop or encircling implants 980a-980h.

Figure 46:
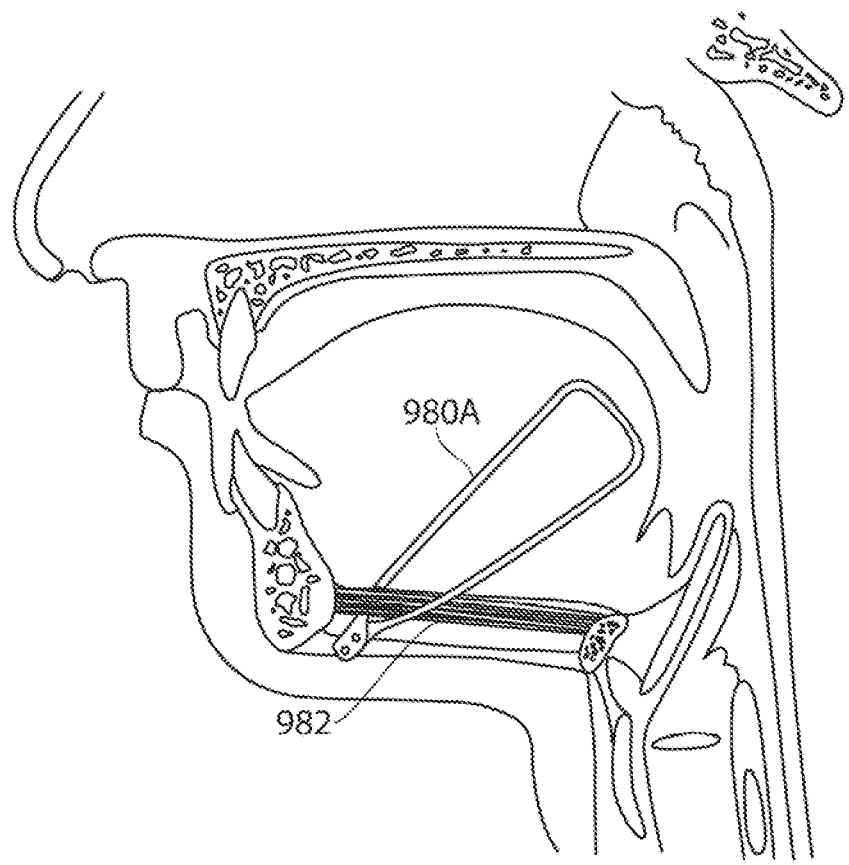
FIG. 46 depicts a loop or encircling implant with its ends fixedly connected around the geniohyoid muscle to serve as an anchor.

FIG. 46 depicts a loop or encircling implant 980a with its ends fixedly connected around the geniohyoid muscle 982 to serve as an anchor.

Figure 47:
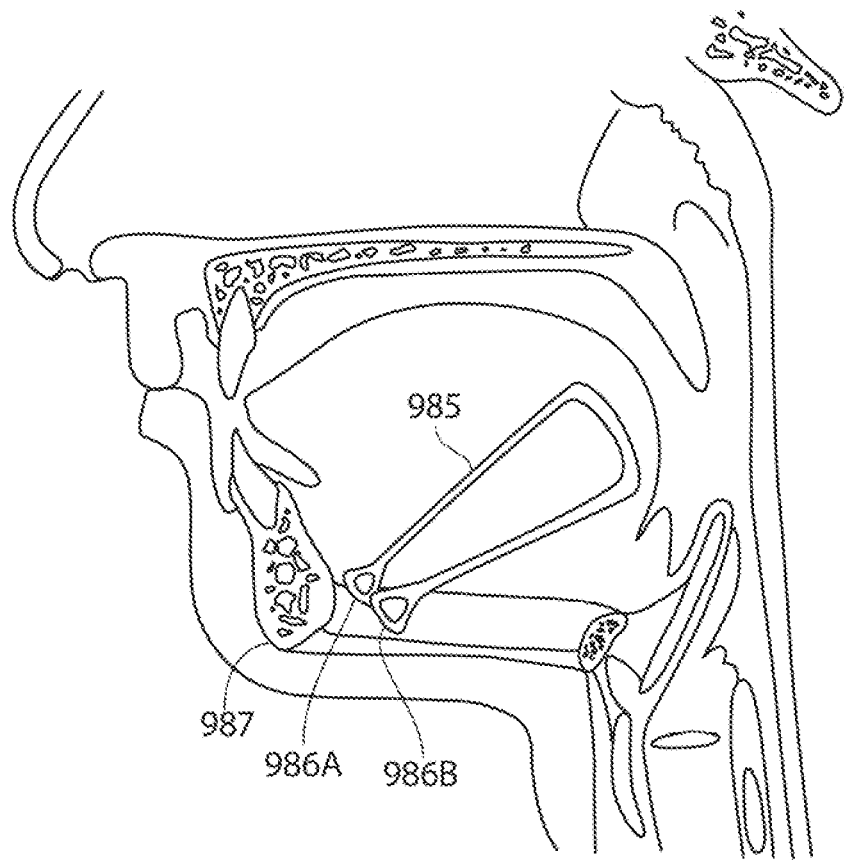
FIG. 47 depicts a U- or V-shaped implant with two anchors in the anterior position, adjacent to the mandible.

FIG. 47 depicts a U- or V-shaped implant 985 with two anchor ends 986a and 986b as described previously in an anterior position adjacent to the mandible 987. This implant can be placed by the same method as in FIGS. 44A-44H above, except that the ends 986 are not connected in a final step of the method.

Figure 48:
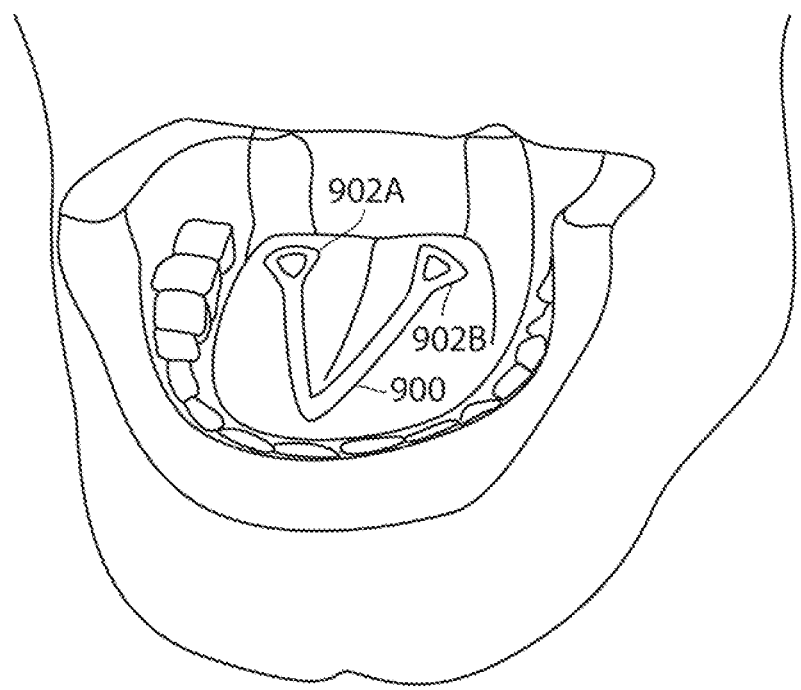
FIG. 48 illustrates a V-shaped implant with two anchors at the distal ends that are the legs of the V-shape in a horizontal orientation in a patient's tongue.
Figure 49:
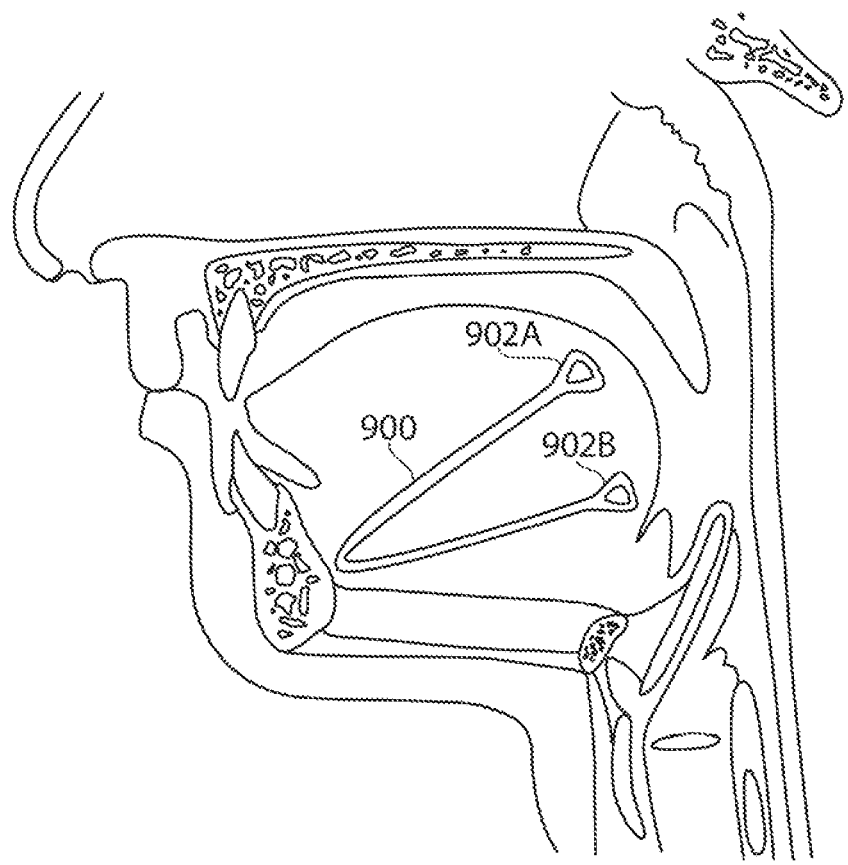
FIG. 49 illustrates a V-shaped implant with two anchors at the distal ends that are the legs of the V-shape in a vertical orientation in a patient's tongue.
Figure 50A:
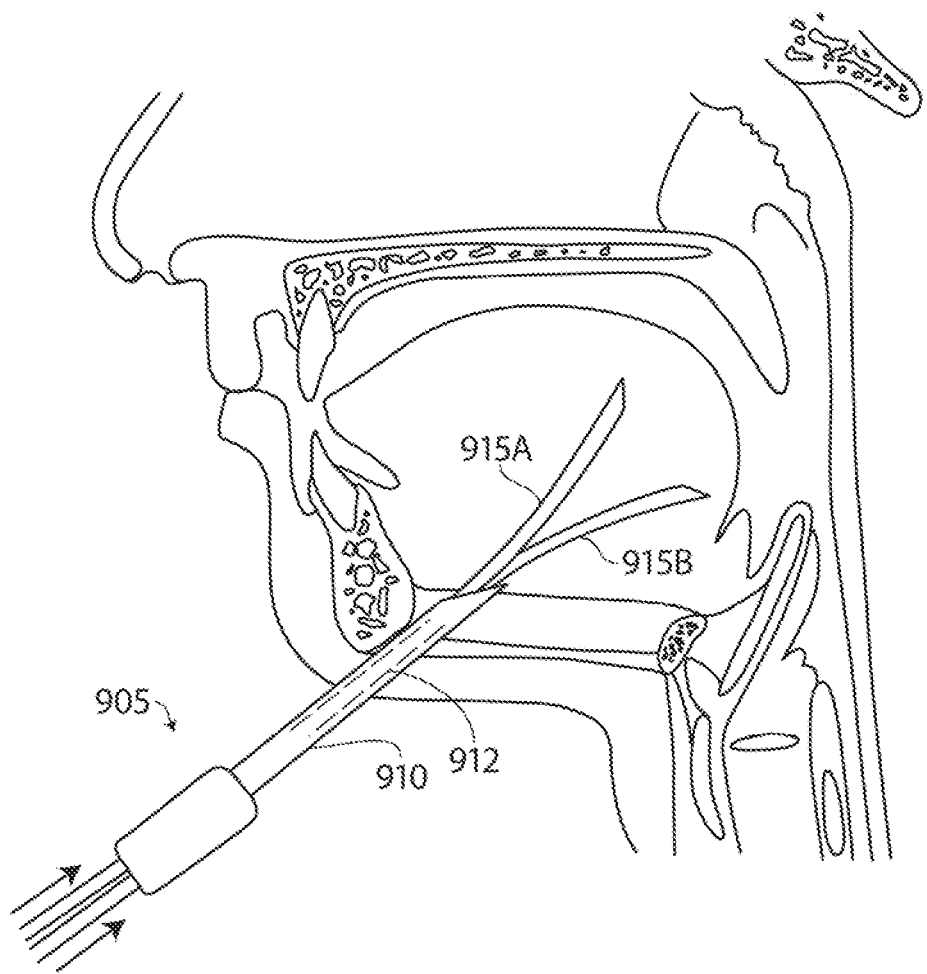
FIG. 50A depicts a device and first step of a method for implanting the V-shaped implant of FIG. 48 in a patient's tongue, wherein two curved tunnelers form pockets for the legs of the V-shaped implant.
Figure 50B:
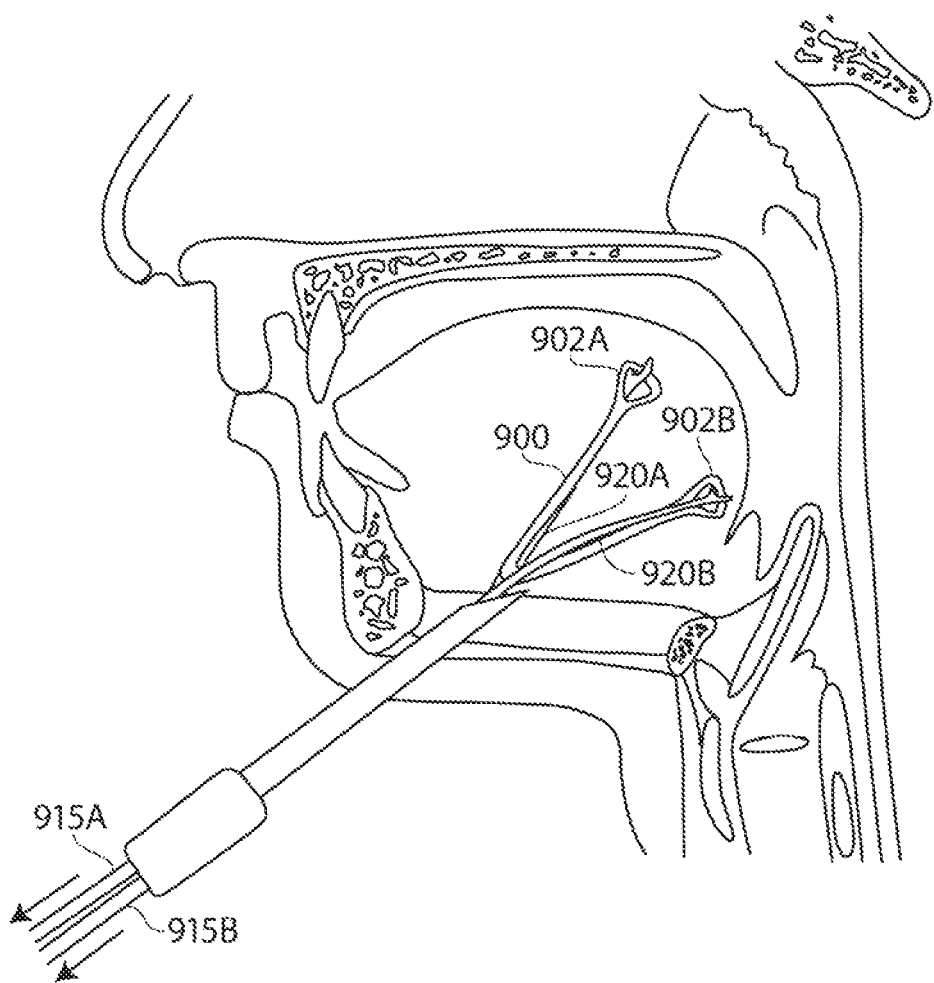
FIG. 50B depicts a subsequent step of the method wherein the tunnelers are removed, and two curved push rods with hooks at the distal ends thereof pushing or maintain the anchor ends of the implant in place.
Figure 50C:
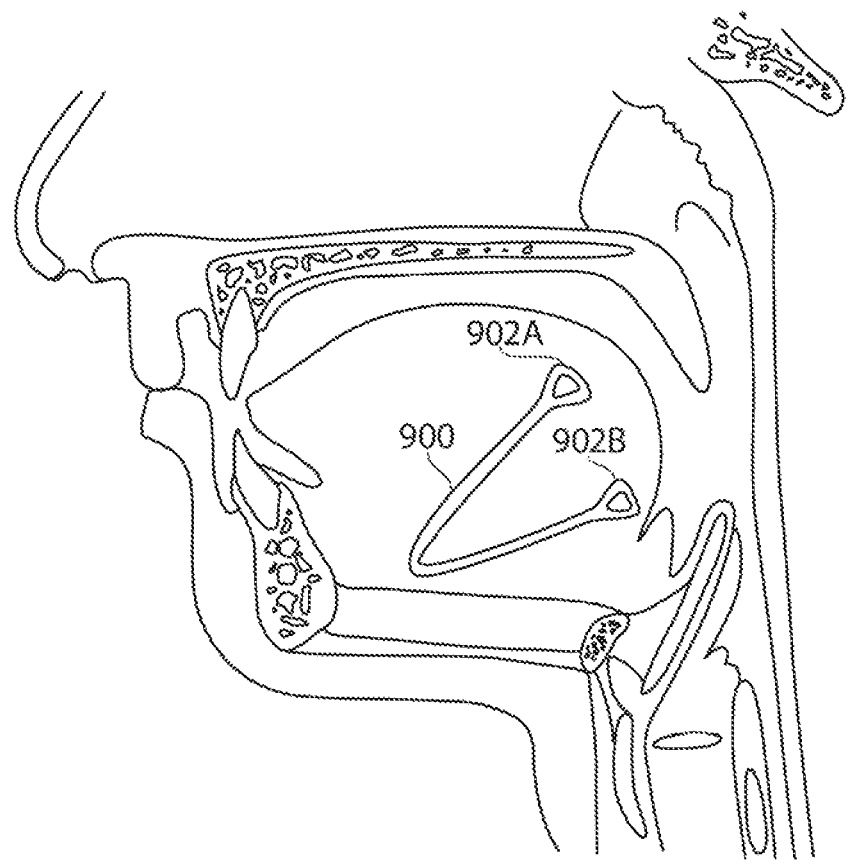
FIG. 50C depicts the patient's tongue after the trocar is withdrawn leaving the V-shaped implant in its final position.

FIGS. 48-49 depict a V-shaped implant 900 with two anchoring portions 902a and 902b at the distal ends of legs of the V-shape. FIG. 48 shows implant 900 in a horizontal orientation, and FIG. 49 shows the implant 900 in a vertical orientation. FIGS. 50A-50C schematically illustrate an apparatus and method for implanting such V-shaped implants through a single entry point. In FIG. 50A, the disclosure provides a trocar 905 with a sharp-tipped trocar sleeve 910 that can be inserted into tissue. A passageway 912 in the trocar sleeve 910 carries first and second curved tunnelers 915A and 915B that can be extended into tissue to form pockets to accept the legs of a V-shaped implant, such as the V-shaped implant 900 that is shown in FIG. 49. A tunneler may have a resilient curved end. A tunneler may be comprised of a shape memory alloy. It can be understood that tunnelers 915A and 915B have a U-shaped transverse sectional shape wherein the longitudinal slot allows for release and deployment of the implant. FIG. 50B depicts the tunnelers 915A and 915B being withdrawn proximally wherein stylets 920A and 920B maintain the implant 900 in the targeted location by grasping implants ends 902a and 902b. FIG. 50C depicts the V-shaped implant 900 in its final deployed location wherein the implant ends 902a, 902b will be anchored in the tissue with tissue plugs as described previously.

Figure 51:
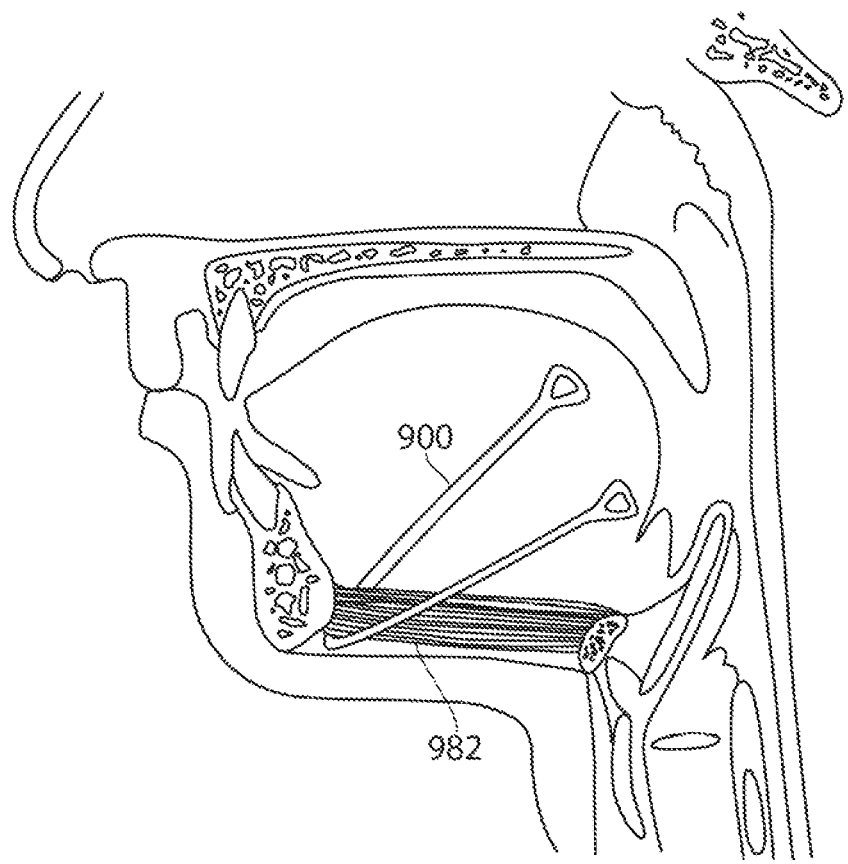
FIG. 51 depicts a V-shaped implant as in FIG. 50C anchored around the geniohyoid muscle.

FIG. 51 illustrates a V-shaped implant 900 as in FIGS. 50A-50C anchored around the geniohyoid muscle 982.

Figure 52:
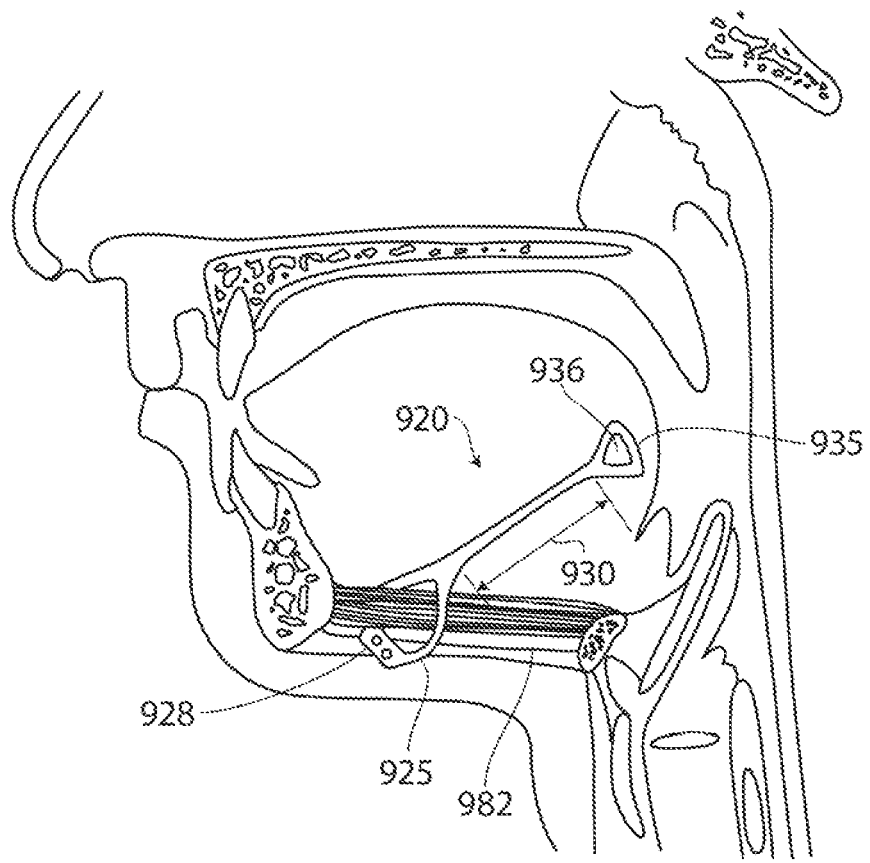
FIG. 52 depicts a combination implant with an encircling portion anchored around the geniohyoid muscle and a linear portion with an anchoring end near the tongue base.

FIG. 52 illustrates an alternative OSA implant 920 that comprises a combination of previously described features wherein the implant includes an encircling portion 925 with attachment means 928 that is coupled to a linear implant portion 930 that extends to an anchoring end 935 that is configured with an opening 936 therein for tissue growth therethrough. The encircling portion 925 encircles the geniohyoid muscle 982.

The embodiments of implants shown in the figures above can be sized and shaped to conform to a treatment site in a patient's tongue, palate or other site in airway-interface tissue and to reside in an orientation and in a manner compatible with normal physiological function of the site. The overall dimensions may vary according to the full extent that human subjects vary in their anatomical dimensions, and thus the dimensions provided here are only an approximation for the purpose of illustration, and are not meant to be limiting. Any embodiment in its elongated state may typically be in the range of about 2 cm to about 10 cm in length in a releasably extended state, and the implant in a contracted state may be in the range of about 1 cm to about 6 cm in length. Testing shows there is an advantage to using these lengths.

Unless defined otherwise, all technical terms used herein have the same meanings as commonly understood by one of ordinary skill in the art to which this invention belongs.

Specific methods, devices, and materials are described in this application, but any methods and materials similar or equivalent to those described herein can be used in the practice of the present invention. While embodiments of the inventive device and method have been described in some detail and by way of exemplary illustrations, such illustration is for purposes of clarity of understanding only, and is not intended to be limiting.

Various terms have been used in the description to convey an understanding of the invention; it will be understood that the meaning of these various terms extends to common linguistic or grammatical variations or forms thereof. It will also be understood that when terminology referring to devices or equipment has used trade names, brand names, or common names, that these names are provided as contemporary examples, and the invention is not limited by such literal scope. Terminology that is introduced at a later date that may be reasonably understood as a derivative of a contemporary term or designating of a subset of objects embraced by a contemporary term will be understood as having been described by the now contemporary terminology.

While some theoretical considerations have been advanced in furtherance of providing an understanding of the invention the claims to the invention are not bound by such theory. Described herein are ways that embodiments of the invention may engage the anatomy and physiology of the airway, generally by opening the airway during sleep; the theoretical consideration being that by such opening of the airway, the implanted device embodiments alleviate the occurrence of apneic events. Moreover, any one or more features of any embodiment of the invention can be combined with any one or more other features of any other embodiment of the invention, without departing from the scope of the invention. Further, it should be understood that while these inventive methods and devices have been described as providing therapeutic benefit to the airway by way of intervention in tissue lining the airway, such devices and embodiments may have therapeutic application in other sites within the body, particularly luminal sites. Still further, it should be understood that the invention is not limited to the embodiments that have been set forth for purposes of exemplification, but is to be defined only by a fair reading of claims that are appended to the patent application, including the full range of equivalency to which each element thereof is entitled.

What is claimed is:

1. A method of treating an airway disorder comprising implanting at least one implant body in a patient's tongue, wherein the at least one implant applies a tensile force in alignment with muscle fibers, and wherein at least one of first and second ends comprise an unbroken loop comprising an elastomeric material and the unbroken loop completely encircling a tissue plug and being subsequently removed by cutting the loop to release the tissue plug from the at least one implant body, the tissue plug being substantially intact after release.

2. The method of claim 1, wherein the loop is adapted to allow tissue plug growth through an opening within the loop to thereby secure the at least one of the first and second ends to the patient's tongue.

3. The method of claim 2, wherein the loop has a disengagement element for disengaging the loop from a surrounded tissue plug.

4. The method of claim 3, further comprising cutting the disengagement element to release a tissue plug from the at least one implant body.

5. The method of claim 2, wherein the opening has a width between about 0.5mm to about 10mm.

6. The method of claim 2, wherein the loop has shaped surface features adapted to interface with tissue plug growth.

7. The method of claim 1, wherein the tensile force is adapted to displace a portion of the patient's tongue at or below a maximum threshold displacement between about 0.5 mm and 20mm.

8. The method of claim 7, wherein the maximum threshold displacement is between 1.0mm and about 15mm.

9. The method of claim 1 wherein the tensile force is applied by a single implant.

10. The method of claim 1 wherein the tensile force is applied collectively by a plurality of implants.

11. The method of claim 1, further comprising implanting another implant body in the patient's tongue in a parallel orientation relative to said at least one implant body.

12. The method of claim 1, further comprising implanting another implant body in a non-parallel orientation relative to said at least one implant body.

13. The method of claim 1, further comprising bioeroding a bioerodible portion on the at least one implant body to thereby transition the at least one implant body from a first configuration to a second configuration, wherein the second configuration displaces the patient's tongue by applying the tensile force.

14. The method of claim 1, further comprising constraining a resiliently deformable portion of the at least one implant body in a deformed shape with a bioerodible portion; and releasing the resiliently deformable portion to a tensioned shape to apply the tensile force to the patient's tongue.

15. The method of claim 1, wherein the at least one implant body comprises a curved configuration and a straight configuration, the at least one implant body biased toward the curved configuration.

16. The method of claim 1, wherein the tensile force is at least about 1.5 Newtons.

17. The method of claim 1, wherein the tensile force is at least about 3.5 Newtons.

18. The method of claim 1, wherein the tensile force is adapted to displace a posterior area of the patient's tongue anteriorly during normal breathing to open the patient's airway.

* * * * *